(12) United States Patent
Tanner et al.

(10) Patent No.: US 7,244,599 B2
(45) Date of Patent: Jul. 17, 2007

(54) GENE AND USES THEREFOR TO MODIFY PASTURE QUALITIES OF CROPS

(75) Inventors: Gregory John Tanner, O'Connor (AU); Anthony Richard Ashton, Cook (AU); Sharon Abrahams, Cook (AU); John McRae Watson, Holder (AU); Philip John Larkin, Weston (AU); Katarzyna Teresa Francki, Amaroo (AU)

(73) Assignees: Commonwealth Scientific and Industrial Research Organisation, Campbell (AU); Meat and Livestock Australia Limited, North Sydney (AU)

( * ) Notice: Subject to any disclaimer, the term of this patent is extended or adjusted under 35 U.S.C. 154(b) by 126 days.

(21) Appl. No.: 10/469,061

(22) PCT Filed: Feb. 21, 2002

(86) PCT No.: PCT/AU02/00179

§ 371 (c)(1),
(2), (4) Date: Mar. 15, 2004

(87) PCT Pub. No.: WO02/066625

PCT Pub. Date: Aug. 29, 2002

(65) Prior Publication Data

US 2004/0191787 A1    Sep. 30, 2004

(51) Int. Cl.
| C12N 9/02 | (2006.01) |
| C12N 5/07 | (2006.01) |
| C12N 15/00 | (2006.01) |
| C12P 23/00 | (2006.01) |
| C12Q 1/40 | (2006.01) |
| C07H 21/04 | (2006.01) |
| A01H 1/00 | (2006.01) |

(52) U.S. Cl. ............ 435/189; 435/6; 435/25; 435/69.1; 435/252.3; 435/320.1; 435/410; 435/468; 435/252.2; 435/419; 536/23.2; 800/278; 800/282; 800/295; 800/298

(58) Field of Classification Search ........... 435/189, 435/320.1, 91.1; 800/278, 282, 284
See application file for complete search history.

(56) References Cited

U.S. PATENT DOCUMENTS

| 6,410,718 B1 * | 6/2002 | Bloksberg et al. ......... 536/23.6 |
| 2004/0034888 A1 * | 2/2004 | Liu et al. .................... 800/289 |
| 2005/0283851 A1 | 12/2005 | Abrahams et al. |

FOREIGN PATENT DOCUMENTS

EP    1033405 A2    9/2000

WO    WO9807836    2/1998

OTHER PUBLICATIONS

Dinkova-Kostova et al., (+)-Pinoresinol/(+)-Lariciresinol reductase from Forsythia intermedia. JBC., 1996 vol. 271 (46): 29473-29482.*
Gang et al., Evolution of plant defense mechanisms. JBC., 1999 vol. 274 (11): 7516-7527.*
Vieths et al., Characterization of a new IgE-binding 35 -kDa protein from Birch pollen with cross-reacting homologues in various plant foods. Scand. J. Immunol., 1998 vol. 47: 263-272.*
Jende-Strid (1991) "Gene-enzyme relations in the pathway of flavonoid biosynthesis in barley" *Theor. Appl. Genet.*, vol. 81, pp. 668-674.
Joseph et al. (1998) "Proanthocyanidin synthesis in the forage legume *Onobrychis viciifolia*. A study of chalcone synthase, dihydroflavonol 4-reductase and leucoanthocyanidin 4-reductase in developing leaves" *Aust. Journal of Plant Physiology*, vol. 25, No. 3, pp. 271-278.
Stafford, Helen A. (1989) Chem. Signif. Condens. Tannis, [Proc. North Am. Tannin Conf.], Eds. Hemingway, Richard W.; Karchesy, Joseph J., Plenum, New York, N.Y., pp. 47-70.
Tanner et al. (1992) "Biosynthesis of Proanthocyanidins (Condensed Tannins) in Barley" *Bulletin de Liason—Groupe Polyphenols*, pp. 170-173.
Guo, et al. (2004) "Protein Tolerance To Random Amino Acid Change," PNAS, 101:9205-9210.
Hass, et al. (2002) GenBank Accession No. AY088019, NCBI, pp. 1-2.
Keskin, et al. (2004) "A New, Structurally Nonredundant, Diverse Data Set of Protein-Protein Interfaces and Its Implications," Protein Science, 13:1043-1055.
Liu, et al. (2002) "Bottlenecks for metabolic engineering of isoflavone glycoconjugates in *Arabidopsis*," PNAS, 99(22):14578-14583.
Thornton, et al. (2000) "From structure to function: Approaches and limitations," Nature Struct. Biol. 7:991-994.

* cited by examiner

*Primary Examiner*—Rebecca E. Prouty
*Assistant Examiner*—Ganapathirama Raghu
(74) *Attorney, Agent, or Firm*—John P. White; Cooper & Dunham LLP

(57) ABSTRACT

The invention relates generally to isolated leucoanthocyanidin reductase LAR polypeptides of the Reductase-Epimerase-Dehydrogenase (RED) protein family, and nucleic acid molecules encoding same and their use in regulating the biosynthesis and accumulation of proanthocyanidins in plants. The invention is further directed to isolated nucleic acid molecules of plants, which encode leucoanthocyanidin reductases of the RED protein family. The isolated polypeptides and nucleic acid molecules of the present invention are useful for modifying the pasture quality of legumes, and, in particular, for producing bloat-safe forage crops, or crops having enhanced nutritional value, enhanced disease resistance or pest resistance, or enhanced malting qualities.

21 Claims, 23 Drawing Sheets

FIGURE 4

DIALIGN 2.1

(Burkhard Morgenstern (1999).
DIALIGN 2: improvement of the segment-to-segment
approach to multiple sequence alignment.
Bioinformatics 15, 211 - 218.)

```
Options:
========

1) protein sequences aligned
    2) 5 "*" characters for regions of maximum similarity Aligned sequences:         length:
==================         =======

1)          Du          382
    2)       MtIFR          318
    3)       LaIFR          312
    4)       PsIFR          318
    5)       GmIFR          307
    6)       CaIFR          318
    7)       StIFR          308
    8)       NtIFR          310
    9)     AtF18014         319
   10)      AtT22F8         308
   11)      PtPCBER         308
   12)       Th2PLR         309
   13)     Tp1PCBER         314
   14)     TH7PCBER         308
   15)     TH6PCBER         307
   16)     TP5PCBER         307
   17)     TH4PCBER         308
   18)     TH3PCBER         308
   19)     TH2PCBER         308
   20)     TH1PCBER         308
   21)      FiPCBER         308
   22)     Fi2PCBER         308
   23)      PbPCBER         308
   24)       U33318         309
   25)       X92075         308
   26)       Y12689         320

Average sequence length: 313.308
```

Figure 4 (cont'd)

The 26 protein sequences in this alignment:

1. DuLAR leucoanthocyanidin reductase *Desmodium uncinatum*
2. MtIFR isoflavone reductase [*Medicago truncatula*] AF277052_1
3. LaIFR probable 2'-hydroxyisoflavone reductase (EC 1.3.1.45) - white lupine. *Lupinus albus* T11035
4. PsIFR 2'-hydroxyisoflavone reductase (EC 1.3.1.45) - garden pea *Pisum sativa*. S48631
5. GmIFR isoflavone reductase homolog 1 [*Glycine max*]. AF202183_1
6. CaIFR *Cicer arietinum* mRNA for NADPH:isoflavone oxidoreductase. X60755
7. StIFR *Solanum tuberosum* mRNA for isoflavone reductase homologue. X92075
8. NtIFR Tobacco mRNA isoflavone reductase-homologue D28505
9. AtF18O14 AC025808 Genomic sequence for *Arabidopsis thaliana* BAC F18O14
10. AtT22F8 *Arabidopsis thaliana* DNA chromosome 4, BAC clone T22F8 AL050351
11. PtPCBER AF242490_1 phenylcoumaran benzylic ether reductase PT1 [*Pinus taeda*].
12. Th2PLR AF242502_1 pinoresinol-lariciresinol reductase TH2 [*Tsuga heterophylla*].
13. Tp1PCBER AF242500 phenylcoumaran benzylic ether reductase homolog Tp1 [*Thuja plicata*].
14. TH7PCBER AF242499_1 phenylcoumaran benzylic ether reductase homolog TH7 [*Tsuga heterophylla*]
15. TH6PCBER AF242498_1 phenylcoumaran benzylic ether reductase homolog TH6 [*Tsuga heterophylla*].
16. TP5PCBER AF242497_1 phenylcoumaran benzylic ether reductase homolog TP5 [*Tsuga heterophylla*].
17. TH4PCBER AF242496_1 phenylcoumaran benzylic ether reductase homolog TH4 [*Tsuga heterophylla*].
18. TH3PCBER AF242495_1 phenylcoumaran benzylic ether reductase homolog TH3 [*Tsuga heterophylla*]
19. TH2PCBER AF242494_1 phenylcoumaran benzylic ether reductase homolog TH2 [*Tsuga heterophylla*].
20. TH1PCBER AF242493_1 phenylcoumaran benzylic ether reductase homolog TH1 [*Tsuga heterophylla*].
21. Fi1PCBER AF242491_1 phenylcoumaran benzylic ether reductase homolog Fi1 [*Forsythia x intermedia*].
22. Fi2PCBER AF242492_1 phenylcoumaran benzylic ether reductase homolog Fi2 [*Forsythia x intermedia*].
23. PbPCBER CAA06706 phenylcoumaran benzylic ether reductase [*Populus balsamifera* subsp. *trichocarpa*].
24. U33318 Zea mays sulfur starvation induced isoflavone reductase-like IRL (IRL) mRNA, complete cds.
25. X92075 S.tuberosum mRNA for isoflavone reductase homologue.
26. Y12689 Grapefruit *C.paradisi* mRNA isoflavone reductase-like protein.

Figure 4 (Cont'd)

Note that only upper-case letters are considered to be aligned.

Alignment (DIALIGN format):
===========================

```
DuLAR     1   mtvsgaipsM TKNRTLVVGG TGFIGQFITK ASLGFGYPTF LLVRPGP---
MtIFR     1   --MA------ TENKILILGP TGAIGRHIVW ASIKAGNPTY ALVRKTPGNV
LaIFR     1   ---------M GKSKVLVVGG TGYVGRRIVK ASLEHGHETF ILQRPEIGL-
PsIFR     1   --MA------ TENKILILGA TGAIGRHIVW ASIKAGNPTY ALVRKTSdNV
GmIFR     1   --MA------ AKSKILVIGG TGYIGKFIVK ASSEAGHPTF ALVREST---
CaIFR     1   --MA------ SQNRILVLGP TGAIGRHVVW ASIKAGNPTY ALIRKTPGDI
StIFR     1   --MA------ GKSKILFIGG TGYIGKFIVE ASAKAGHDTF VLVREST---
NtIFR     1   mvVS------ EKSKILIIGG TGYIGKYLVE TSAKSGHPTF ALIREST---
AtF18014  1   m--------- -TSKILVIGA TGLIGKVLVE ESAKSGHATF ALVREAS---
AtT22F8   1   --MT------ SKSKILFIGG TGYIGKYIVE ASARSGHPTL VLVRNST---
PtPCBER   1   --MG------ SRSRILLIGA TGYIGRHVAK ASLDLGHPTF LLVREST---
Th2PLR    1   m--------- --SRVLIVGG TGYIGRKFVK ASLALGHPTF VLSRPEVGF-
Tp1PCBER  1   --MD------ KKSRVLIVGG TGFIGKRIVK ASLALGHPTY VLFRPEA---
TH7PCBER  1   --MG------ SSSRILIIGA TGYIGRHVAK ASLDLGHPTF LLLRDST---
TH6PCBER  1   --MA------ NSSKILIIGG TGYIGRHISK ASLALGHPTF LLVRESS---
TP5PCBER  1   --MA------ NSSKILIIGG TGYIGRHISK ASLALGHPTF LLVRESS---
TH4PCBER  1   --MG------ SKSRVLIIGG TGYIGRHVAK ASLDLGHPTF LLLREST---
TH3PCBER  1   --MG------ SKSKILIIGA TGYIGRQVAK ASLALSHPTF LLVRDSP---
TH2PCBER  1   --MG------ SKSKILIIGA TGYIGRQVAK ASLALSHPTF LLVRDSP---
TH1PCBER  1   --MG------ SKSRVLIIGG TGYIGRHVAK ASLDLGHPTF LLLREST---
FiPCBER   1   --MA------ EKTKILIIGG TGYIGKFVAE ASAKSGHPTF ALFREST---
Fi2PCBER  1   --MA------ EKTKILIIGG TGYIGKFVAE ASAKSGHPTF ALFREST---
PbPCBER   1   --MA------ DKSKILIIGG TGYIGKFIVE ASAKAGHPTF ALVREST---
U33318    1   ma-S------ EKSKILVVGG TGYLGRHVVA ASARLGHPTS ALVRDTA---
X92075    1   --MA------ GKSKILFIGG TGYIGKFIVE ASAKAGHDTF VLVREST---
Y12689    1   megen----- TKPKILIFGG TGYFGKYMVK ASVSSGHKTF VYARPVT---
              **         * ********* ********** ********** **********
              **           ********* ********** ********** *******
                         ********** ********** ********** *******
                          ********* ********** ********** ******
                           *****  ********** ******* *
```

Figure 4 (Cont'd)

```
Du        48  -------V-S  ---PSK----  -----AVIIK  TFQDKGAKVI  YGVINDKECM
MtIFR     43  NKPKLITA-A  NP-ETK----  -----EELID  NYQSLGVILL  EGDINDHETL
LaIFR     41  ----------  -D-IEK----  -----LQILL  SFKKQGAILV  EASFSDHKSL
PsIFR     43  NKPKLTEA-A  NP-ETK----  -----EELLK  NYQASGVILL  EGDINDHETL
GmIFR     40  -------L-S  -H-PEK----  -----FKLIE  SFKTSGVTLL  YGDLTDHESL
CaIFR     43  NKPSLVAA-A  NP-ESK----  -----EELLQ  SFKAAGVILL  EGDMNDHEAL
StIFR     40  -------L-S  -N-PTK----  -----TKLID  TFKSFGVTFV  HGDLYDHESL
NtIFR     42  -------L-K  -N-PEK----  -----SKLID  TFKSYGVTLL  FGDISNQESL
AtF18014  38  -------L-S  -D-PVKaqlv  erfkdLGVTI  LYVRSNPLLM  LGSLSDKESL
AtT22F8   40  -------L-T  -S-PSR----  -----SSTIE  NFKNLGVQFL  LGDLDDHTSL
PtPCBER   40  -------A-S  -SNSEK----  -----AQLLE  SFKASGANIV  HGSIDDHASL
Th2PLR    39  ----------  -D-IEK----  -----VHMLL  SFKQAGARLL  EGSFEDFQSL
Tp1PCBER  40  -------L-S  -Y-IDK----  -----VQMLI  SFKQLGAKLL  EASLDDHQGL
TH7PCBER  40  -------S-S  -SNSEK----  -----AQLVE  SFKDSSAHIL  HGSIEDHASL
TH6PCBER  40  -------A-S  -N-PEK----  -----AKLLE  SFKASGAIIV  NGSLEDQASL
TP5PCBER  40  -------A-S  -N-PEK----  -----AKLLE  SFKASGAIIV  NGSLEDQVSL
TH4PCBER  40  -------PsS  -N-SEK----  -----AQLVE  SFKASGAKIL  HGSIEDHASL
TH3PCBER  40  -------ASS  -K-PEK----  -----AQLLD  SFKASGANIL  KGSLEDHASL
TH2PCBER  40  -------ASS  -K-PEK----  -----AQLLD  SFKASGANIL  KGSLEDHASL
TH1PCBER  40  -------A-S  SN-SEK----  -----AQLVE  SFKASGANIL  HGSIEDHASL
Fi1PCBER  40  -------I-S  -D-PVK----  -----GKIIE  GFKNSGVTIL  TGDLYDHESL
Fi2PCBER  40  -------I-S  -D-PVK----  -----GKIIE  GFKNSGVTIL  TGDLYDHESL
PbPCBER   40  -------V-S  -D-PVK----  -----RELVE  KFKNLGVTLI  HGDVDGHDNL
U33318    41  -------P-S  -D-PAK----  -----AALLK  SFQDAGVTLL  KGDLYDQASL
X92075    40  -------L-S  -N-PTK----  -----TKLID  TFKSFGVTFV  HGDLYDHESL
Y12689    43  -------Q-N  SR-PSK----  -----LEIHK  EFQGIGVTII  EGELDEHEKI

```
Du       78  EKILKeyEID VVISLVG---  -GAR----LL  DQLTLLEAIK  SVKTIKRFLP
MtIFR    82  VKAIK--QVD IVICAAG---  -RLL----IE  DQVKIIKAIK  EAGNVKKFFP
LaIFR    70  VDAVK--LVD VVICTMSGVH  FRs---HNLL  TQLKLVEAIK  DAGNIKRFLP
PsIFR    82  VNAIK--QVD TVICAAG---  -RLL----IE  DQVKVIKAIK  EAGNVKRFFP
GmIFR    71  VKAIK--QVD VVISALG---  -AEQ----ID  DQVKIIAAIK  EAGNIKRLLP
CaIFR    82  VKAIK--QVD TVICTFG---  -RLL----IL  DQVKIIKAIK  EAGNVKRFFP
StIFR    71  VKAIK--QVD VVISTVG---  -HAL----LA  DQVKLIAAIK  EAGNVKRFFP
NtIFR    73  LKAIK--QVD VVISTVG---  -GQQ----FT  DQVNIIKAIK  EAGNIKRFLP
AtF18014 78  VKAIK--QVD VVISAVGr--  FQTE----IL  NQTNIIDAIK  ESGNVKRFLP
AtT22F8  71  VNSIK--QAD VVISTVG---  -HSL----LG  HQYKIISAIK  EAGNVKRFFP
PtPCBER  72  VEAVK--NVD VVISTVG---  -SLQ----IE  SQVNIIKAIK  EVGTVKRFFP
Th2PLR   68  VAALK--QVD VVISAVAGNH  FRNL----IL  QQLKLVEAIK  EARNIKRFLP
Tp1PCBER 71  VDVVK--QVD VVISAVS---  -GGLvrHHIL  DQLKLVEAIK  EAGNIKRFLP
TH7PCBER 72  VEAVK--QVD VVISTVG---  -TQQ----IE  KQVNIIKGIK  EVRTIKRFLP
TH6PCBER 71  VEAIK--KVD VVISAVK---  -GPQ----LG  DQLNIIKAIK  EIGTIKRFLP
TP5PCBER 71  VEAIK--KVD VVISAVK---  -GPQ----LG  DQLNIIKAIK  EIGTIKRFLP
TH4PCBER 72  VEAVK--QVD VVISTVG---  -SLQ----IE  NQVNIIKAIK  EVGTIKRFLP
TH3PCBER 72  VEAVK--KVD VVISTVG---  -GEQ----IA  NQFNIIKAIK  EVGTIKRFLP
TH2PCBER 72  VEAVK--KVD VVISTVG---  -GEQ----IA  NQFNIIKAIK  EVGTIKRFLP
TH1PCBER 72  VEAVK--QVD VVISTVG---  -SLQ----IE  NQVNIIKAIK  EVGTIKRFLP
FiPCBER  71  VKAIK--QVD VVISTVG---  -SLQ----LA  DQVKIIAAIK  EAGNVKRFFP
Fi2PCBER 71  VKAIK--QVD VVISTVG---  -SLQ----LA  DQVKIIGAIK  EAGNVKRFFP
PbPCBER  71  VKAIK--RVD VVISAIG---  -SMQ----IA  DQTKIIAAIK  EAGNVKRFFP
U33318   72  VSAVK--GAD VVISVLG---  -SMQ----IA  DQSRLVDAIK  EAGNVKRFFP
X92075   71  VKAIK--QVD VVISTVG---  -HAL----LA  DQVKLIAAIK  EAGNVKRFFP
Y12689   75  VSILK--EVD VVISTVT---  -YPQ----CL  DQLKIVHAIK  VAGNIKRFLP

```
Du        120  SEFGHDVDRT -DPVEPGLTM YKEKRLVRRA VEEYGIPFTN ICCNSIASWp
MtIFR     122  SEFGLDVDRH -EAVEPVRQV FEEKASIRRV IEAEGVPYTY LCCHAFTGYF
LaIFR     115  SEFGMDPALM GHALEPGRVT FDEKMTVRKA IEEANIPFTY ISANCFAGYF
PsIFR     122  SEFGLDVDRH -DAVEPVRQV FEEKASIRRV VESEGVPYTY LCCHAFTGYF
GmIFR     111  SEFGHDVDHH -NAVEPVSSF FEKKVKIRRA IEAEGIPYTY ISSNSFAGHF
CaIFR     122  SEFGLDVDRH -DAVDPVRPV FDEKASIRRV VEAEGVPYTY LCCHAFTGYF
StIFR     111  SEFGNDVDRV -HAVEPAKAA FNTKAQIRRV VEAEGIPFTY VATFFFAGYS
NtIFR     113  SEFGFDVDHA -RAIEPAASL FALKVRIRRM IEAEGIPYTY VICNWFADFF
AtF18014  120  SEFGNDVDRT -VAIEPTLSE FITKAQIRRA IEAAKIPYTY VVSGCFAGLF
AtT22F8   111  SEFGNDVDRV -FTVEPAKSA YATKAKIRRT IEAEGIPYTY VSCNFFAGYF
PtPCBER   112  SEFGNDVDNV -HAVEPAKSV FEVKAKVRRA IEABGIPYTY VSSNCFAGYF
Th2PLR    112  SEFGMDPDLM EHALEPGNAV FIDKRKVRRA IEAAGIPYTY VSSNIFAGYL
Tp1PCBER  115  SEFGMDPDVV EDPLEPGNIT FIDKRKVRRA IEAATIPYTY VSSNMFAGFF
TH7PCBER  112  SEFRNDVDNV -HAVEPAKSV FGLKAKVRRA IEAEGIPYTY VSSNCFAGYF
TH6PCBER  111  SEFGNDVDRT -HAVEPAKTM FANKAKIRRA IEAEGIPYTY VSSNCFAGLF
TP5PCBER  111  SEFGNDVDRT -HAVEPAKTM FANKAKIRRA IEAEGIPYTY VSSNCFAGLF
TH4PCBER  112  SEFGNDVDKV -HAVEPAKSV FEVKAKVRRA IEAEGIPYTY ISSNCFAGYF
TH3PCBER  112  SEFGNDVDNV -HAVEPAKSV FELKAQVRRA IEAESIPYTY VSSNCFAGYF
TH2PCBER  112  SEFGNDVDNV -HAVEPAKSV FELKAQVRRA IEAESIPYTY VSSNCFAGYF
TH1PCBER  112  SEFGNDVDKV -HAVEPAKSV FEVKAKVRRA IEAEGIPYTY ISSNCFAGYF
FiPCBER   111  SEFGTDVDRC -HAVEPAKSS YEIKSKIRRA VEAEGIPFTF VSSNYFAGYS
Fi2PCBER  111  SEFGTDVDRC -HAVEPAKSS FEIKSKIRRA VEAEGIPFTF VSSNYFGGYS
PbPCBER   111  SEFGMDVDHV -NAVEPAKTA FAMKAQIRRA IEAAGIPYTY VPSNFFAAYY
U33318    112  SEFGLDVDRT -GIVEPAKSI LGAKVGIRRA TEAAGIPYTY AVAGFFAGFG
X92075    111  SEFGNDVDRV -HAVEPAKAA FNTKAQIRRV VEAEGIPFTY VATFFFAGYS
Y12689    115  SDFECEEDRV -RPLPPFEAC LEKKRIVRRA IEAAQIPYTF VSANLCGAYF

```
Du         169  yydn--CHPS  ---QVPPPMD  QFQIYGDGNT  KAYFIDGNDI  GKFTMKTIDD
MtIFR      171  LRNLAQ--LD  ---VTDPPRD  KVVILGDGNV  KGAYVTEADV  GTFTIKAAND
LaIFR      165  AGNLSQ--MK  ---TLLPPRD  KVLLYGDGNV  KPVYMDEDDV  ATYTIKTIDD
PsIFR      171  LRNLAQ--ID  ---ATDPPRD  KVVILGDGNV  RGAYVTEADV  GTYTIRAAND
GmIFR      160  LPNLLQ--QN  ---VTAPPRD  EVVILGDGNI  KGVYVIEEDV  ATYTIKAVDD
CaIFR      171  LRNLAQ--FD  ---ATEPPRD  KVIILGDGNV  KGAYVTEADV  GTYTIRAAND
StIFR      160  LPNLAQ--PG  ---AAGPPND  KVVILGHGNT  KAVFNKEEDI  GTYTINAVDD
NtIFR      162  LPNLGQ--LE  ---AKTPPRD  KVVIFGDGNP  KAIYVKEEDI  ATYTIEAVDD
AtF18014   169  VPCLGQCH1r  ---LRSPPRD  KVSIYDTGNG  KAIVNTEEDI  VAYTLKAVDD
AtT22F8    160  LPTLAQ--PG  ---ATSAPRD  KVIVLGDGNP  KAVFNKEEDI  GTYTINAVDD
PtPCBER    161  LRSLAQ--AG  ---LTAPPRD  KVVILGDGNA  RVVFVKEEDI  GTFTIKAVDD
Th2PLR     162  AGGLAQ--IG  ---RLMPPRD  EVVIYGDGNV  KAVWVDEDDV  GIYTLKTIDD
Tp1PCBER   165  AGSLAQ--LQ  dapRMMPARD  KVLIYGDGNV  KGVYVDEDDA  GIYIVKSIDD
TH7PCBER   161  AANLAQ--AG  ---LKTPPKD  KVVILGDGNA  KAVYVKEEDI  GTFTIKAVDD
TH6PCBER   160  LPSLGQ--PG  ---LSSPPRD  KAVISGDGNA  KVVFVKEEDI  GTFTIKAVDD
TP5PCBER   160  LPSLGQ--PG  ---LSAPPRD  KAVISGDGNA  KVVFVKEEDI  GTFTIKAVDD
TH4PCBER   161  LPGLGQ--PG  ---LTTPPRD  KIVILGDGNA  KVVYAKEEDI  GTFTIKAVDD
TH3PCBER   161  LPSFAQ--AG  ---LTSPPRD  KVVILGDGNA  KAVYVKEEDI  GTFAIKAADD
TH2PCBER   161  LPSFAQ--AG  ---LTSPPRD  KVVILGDGNA  KAVYVKEEDI  GTFAIKAADD
TH1PCBER   161  LPGLGQ--PG  ---LTTPPRD  KIVILGDGNA  KVVYAKEEDI  GTFTIKAVDD
FiPCBER    160  LPTLVQ--PG  ---VTAPPRD  KVIILGDGNA  KAVFNEEHDI  GTYTIKAVDD
Fi2PCBER   160  LPTLVQ--PG  ---VTAPPRD  KVIILGDGNA  KAVFNEEHDI  GTYTIKAVDD
PbPCBER    160  LPTLAQ--FG  ---LTAPPRD  KITILGDGNA  KLVFNKEDDI  GTYTIKAVDD
U33318     161  LPKVGQ--VL  ---APGPPAD  KAVVLGDGDT  KAVFVEEGDI  ATYTVLAADD
X92075     160  LPNLAQ--PG  ---AAGPPND  KVVILGHGNT  KAVFNKEEDI  GTYTINAVDD
Y12689     164  VNVL-----L  ---RPSESHD  DVVVYGSGEA  KAVFNYEEDI  AKCTIKVIND

```
Du        214  IRTLNKNVHF  RPSSNCYSIN  ELASLWEKKI  GRTLPRFTVT  ADKLLAHAAE
MtIFR     216  PNTLNKAVHI  RLPKNYLTQN  EVISLWEKKI  GKTLEKTYVS  EEQVLKDIQE
LaIFR     210  PRTLNKTVYL  RPPENILTHK  ELIEKWEELI  GKQLEKNSIS  EKDFLSTLKG
PsIFR     216  PNTLNKAVHI  RLPNNYLTAN  EVIALWEKKI  GKTLEKTYVS  EEQVLKDIQT
GmIFR     205  PRTLNKTLYL  RPHANVLTFN  ELVSLWENKI  KSSLDKIYVP  EDQLLKSIQE
CaIFR     216  PRTLNKAVHI  RLPHNYLTSN  EVVSLWEKKI  GKTLEKSYIS  EEKVLKDINV
StIFR     205  PKTLNKILYI  KPPHNIITLN  ELVSLWEKKT  GKNLERLYVP  EEQVLKNIQE
NtIFR     207  PRTLNKTLHM  RPPANILSFN  EIVSLWEDKI  GKTLEKLYLS  EEDILQIVQE
AtF18014  216  PRTLNKILYI  HPPNYIVSQN  DMVGLWEEKI  GKTLEKTYVS  EEELLKTIQE
AtT22F8   205  PRTLNKILYI  RPPMNTYSFN  DLVSLWENKI  GKTLERIYVP  EEQLLKQIIE
PtPCBER   206  PRTLNKTLYL  RLPANTLSLN  ELVAKWEKLS  DKTLEKAYVP  EEEVLKLIAD
Th2PLR    207  PRTLNKTVYI  RPLKNILSQK  ELVAKWEKLS  GKFLKKTYIS  AEDFLAGIED
Tp1PCBER  213  PRTLNKTVYI  RPPMNILSQK  EVVEIWERLS  GLSLEKIYVS  EDQLLNMKD-
TH7PCBER  206  PRTLNKTLYL  RLPANTLSFN  ELVGIWEKKI  DKTLDKVYVP  EEEVLKLIAE
TH6PCBER  205  PRALNKILYL  RLPANTYSIN  DLVALWEKKI  GKTLEKTYLS  EEEVLKKIAE
TP5PCBER  205  PRALNKILYL  RLPANTYSIN  DLVALWEKKI  GKTLEKTYLS  EEEVLKKIAE
TH4PCBER  206  LRTLNKTLYL  RLPANTLSFN  EVVGLWEKKI  DKTLEKVYVP  EEGVLKLIAD
TH3PCBER  206  PRTLNKTLYL  RLPANTLSFN  ELVALWEKKI  GKTLEKVYVP  EEHVVKLIAE
TH2PCBER  206  PRTLNKTLYL  RLPANTLSFN  ELVALWEKKI  GKTLEKVYVP  EEHVVKLIAE
TH1PCBER  206  LRTLNKTLYL  RLPANTLSFN  EVVGLWEKKI  DKTLEKVYVP  EEGVLKLIAD
FiPCBER   205  PRTLNKILYI  KPPKNIYSFN  ELVALWENKI  GKTLEKIYVQ  EEQLIKQIEE
Fi2PCBER  205  PRTLNKILYI  KPPKNILHSM  KLVALWENKI  GKTLEKIYVP  EEQLIKQIEE
PbPCBER   205  ARTLNKTVLI  KPPKNTYSFN  ELIDLWEKKI  GKTLEKTFVP  EEKLLKDIQE
U33318    206  PRAENKVLYI  KPPANTLSHN  ELLSLWEKKT  GKTFRREYVP  EEAVLKQIQE
X92075    205  PKTLNKILYI  KPPHNIITLN  ELVSLWEKKT  GKNLERLYVP  EEQVLKNIQE
Y12689    206  PRTCNRIVIY  RPQASIISQL  ELISLWEQKT  GWSFKRVHVS  EEELVKLSET

```
Du        264  NIIPESIVSS FTHDIFINGC QVNFSIDEHS DVEIDTLYPD EKFRSLDDCY
MtIFR     266  SSFPHNYLLA LYHSQQIKGD A-VYEIDPTK DIEASEAYPD VTYTTADEYL
LaIFR     260  LDFASQVGVG HFYHIFYEGC LTNFEIG-EN GEEASELYPE VNYTRMDQYL
PsIFR     266  SSFPHNYLLA LYHSQQIKGD A-VYEIDPAK DVEAYDAYPD VKYTTADEYL
GmIFR     255  SSFPANFMLA LGHSMLVKGD C-NYEIDPSF GVEASKLYPE VKYTTVDNYL
CaIFR     266  STFPHNYLLA LYHSQQIKGD A-VYEIDPAK DAEAYDLYPD VKYTTADEYL
StIFR     255  ASVPMNVGLS IYHTAFVKGD HTNFEIEPSF GVEASEVYPD VKYTPIDEIL
NtIFR     257  GPLPLRTNLA ICHSVFVNGD SANFEVQPPT GVEATELYPK VKYTTVDEFY
AtF18014  266  SKPPMDFLVG LIHTILVKSD FTSFTIDPSF GVEASELYPE VKYTSVDEFL
AtT22F8   255  SSPPLNVMLS LCHCVFVKGG HTSFEIEPSF GVEASELYPD VKYTTVDEIL
PtPCBER   256  TPFPANISIA ISHSIFVKGD QTNFEIG-PA GVEASQLYPD VKYTTVDEYL
Th2PLR    257  QPYEHQVGIS HFYQMFYSGD LYNFEIG-PD GREATMLYPE VQYTTMDSYL
Tp1PCBER  262  KSYVEKMARC HLYHFFIKGD LYNFEIG-PN ATEGTKLYPE VKYTTMDSYM
TH7PCBER  256  TPFPGNISIA IRHSIFVKGD QTNFEIG-PD GVEASELYPD VKYTTVDEYL
TH6PCBER  255  SPFPVNAMLS TGHSIFVKGD QTNFEIG-PD GVEASQLYPE VKYTTVEEYL
TP5PCBER  255  SPFPVNAMLS TGHSIFVKGD QTNFEIG-PD GVEASQLYPE VKYTTVEEYL
TH4PCBER  256  TPFPANIGIA IGHSIFVRGD QTNFEIG-AD GVEASQLYPE VQYTTVDEYL
TH3PCBER  256  TPFPANIVIA IGHSIFVKGD QTNFDIG-PD GVEGSLLYPD VKYTTVDEYL
TH2PCBER  256  TPFPANIVIA IGHSIFVKGD QTNFDIG-PD GVEGSLLYPD VKYTTVDEYL
TH1PCBER  256  TPFPANIGIA IGHSIFVRGD QTNFEIG-AD GVEASQLYPE VQYTTVDEYL
FiPCBER   255  SPFPINIVLA INHSVFVKGD LTNFKIEPSF GVEASELYPD VKYTTVEEYL
Fi2PCBER  255  SPFPINIVLA INHSAFVKGD LTNFKIEPSF GVEASELYPD VKYTTVEEYL
PbPCBER   255  SPIPINIVLS INHSALVNGD MTNFEIDPSW GLEASELYPD VKYTTVEEYL
U33318    256  SPIPLNIILA IGHAAFVRGE QTGFEIDPAK GVDASELYPD VKYTTVDEYL
X92075    255  ASVPMNVGLS IYHTAFVKGD HTNFEIEPSF GVEASEVYPD VKYTPIDEIL
Y12689    256  LPPPEDIPIS IIHSALAKGD LMNFELG-ED DIEASMLYPD FKFTTIDQLL

| | | | | | | |
|---|---|---|---|---|---|---|
| Du | 314 | EDFVpmvhdk | ihagksgeik | ikdgkplvqt | gtieeinkdi | ktlvetqpne |
| MtIFR | 315 | NQFV | | | | |
| LaIFR | 309 | KVYV | | | | |
| PsIFR | 315 | NQFV | | | | |
| GmIFR | 304 | NAFV | | | | |
| CaIFR | 315 | DQFV | | | | |
| StIFR | 305 | NQYV | | | | |
| NtIFR | 307 | NKFV | | | | |
| AtF18014 | 316 | NRFI | | | | |
| AtT22F8 | 305 | NQYV | | | | |
| PtPCBER | 305 | SNFV | | | | |
| Th2PLR | 306 | KRYL | | | | |
| Tp1PCBER | 311 | ERYL | | | | |
| TH7PCBER | 305 | IKFV | | | | |
| TH6PCBER | 304 | GQYV | | | | |
| TP5PCBER | 304 | GQYV | | | | |
| TH4PCBER | 305 | SKFV | | | | |
| TH3PCBER | 305 | SAFV | | | | |
| TH2PCBER | 305 | SAFV | | | | |
| TH1PCBER | 305 | SKFV | | | | |
| Fi PCBER | 305 | SHFV | | | | |
| Fi2PCBER | 305 | NHFV | | | | |
| PbPCBER | 305 | DQFV | | | | |
| U33318 | 306 | NRFL | | | | |
| X92075 | 305 | NQYV | | | | |
| Y12689 | 305 | DIFLidppkp | artafe | | | |

| | | | |
|---|---|---|---|
| Du | 364 | eikkdmkalv | eavpisamg |
| MtIFR | 319 | ---------- | --------- |
| LaIFR | 313 | ---------- | --------- |
| PsIFR | 319 | ---------- | --------- |
| GmIFR | 308 | ---------- | --------- |
| CaIFR | 319 | ---------- | --------- |
| StIFR | 309 | ---------- | --------- |
| NtIFR | 311 | ---------- | --------- |
| AtF18O14 | 320 | ---------- | --------- |
| AtT22F8 | 309 | ---------- | --------- |
| PtPCBER | 309 | ---------- | --------- |
| Th2PLR | 310 | ---------- | --------- |
| Tp1PCBER | 315 | ---------- | --------- |
| TH7PCBER | 309 | ---------- | --------- |
| TH6PCBER | 308 | ---------- | --------- |
| TP5PCBER | 308 | ---------- | --------- |
| TH4PCBER | 309 | ---------- | --------- |
| TH3PCBER | 309 | ---------- | --------- |
| TH2PCBER | 309 | ---------- | --------- |
| TH1PCBER | 309 | ---------- | --------- |
| FiPCBER | 309 | ---------- | --------- |
| Fi2PCBER | 309 | ---------- | --------- |
| PbPCBER | 309 | ---------- | --------- |
| U33318 | 310 | ---------- | --------- |
| X92075 | 309 | ---------- | --------- |
| Y12689 | 321 | ---------- | --------- |

SEQUENCE LISTING

<160> NUMBER OF SEQ ID NOS: 56

<210> SEQ ID NO 1
<211> LENGTH: 9
<212> TYPE: PRT
<213> ORGANISM: Artificial sequence
<220> FEATURE:
<223> OTHER INFORMATION: Onobrychis viciifolia

```
<400> SEQUENCE: 1

His Phe Asp Cys Ala Ala Asp Tyr Lys
1               5

<210> SEQ ID NO 2
<211> LENGTH: 13
<212> TYPE: PRT
<213> ORGANISM: Artificial sequence
<220> FEATURE:
<223> OTHER INFORMATION: Onobrychis viciifolia

<400> SEQUENCE: 2

Lys Glu Asn Phe Gln Val Phe Asp Phe Glu Leu Ser Lys
1               5                   10

<210> SEQ ID NO 3
<211> LENGTH: 7
<212> TYPE: PRT
<213> ORGANISM: Artificial sequence
<220> FEATURE:
<223> OTHER INFORMATION: Onobrychis viciifolia

<400> SEQUENCE: 3

Gly Asp Leu Ile Leu Met Asp
1               5

<210> SEQ ID NO 4
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: 2...2
<223> OTHER INFORMATION: Xaa is Met, Ile, Val, Leu, Phe, or Tyr
<220> FEATURE:
<221> NAME/KEY: misc_feature
<222> LOCATION: 3...3
<223> OTHER INFORMATION: Xaa is  Met, Ile, Val, or Leu
<220> FEATURE:
<221> NAME/KEY: misc_feature
<222> LOCATION: 5...5
<223> OTHER INFORMATION: Xaa is Ala, Gly, or Pro
<220> FEATURE:
<221> NAME/KEY: misc_feature
<222> LOCATION: 8...8
<223> OTHER INFORMATION: Xaa is any amino acid
<220> FEATURE:
<221> NAME/KEY: misc_feature
<222> LOCATION: 9...9
<223> OTHER INFORMATION: Xaa is Met, Ile, Val, Leu, Phe, or Tyr
<220> FEATURE:
<221> NAME/KEY: misc_feature
<222> LOCATION: 11...11
<223> OTHER INFORMATION: Xaa is a charged amino acid residue, Asn, or
      Gln

<400> SEQUENCE: 4

Leu Xaa Xaa Gly Xaa Thr Gly Xaa Xaa Gly Xaa
1               5                   10

<210> SEQ ID NO 5
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: 2...2
```

```
<223> OTHER INFORMATION: Xaa is Arg or Lys
<220> FEATURE:
<221> NAME/KEY: misc_feature
<222> LOCATION: (3)...(4)
<223> OTHER INFORMATION: Xaa is Phe, Tyr,  Met, Ile, Val, or Leu
<220> FEATURE:
<221> NAME/KEY: misc_feature
<222> LOCATION: 9...9
<223> OTHER INFORMATION: Xaa is Ala, Gly, Arg, or Lys
<220> FEATURE:
<221> NAME/KEY: misc_feature
<222> LOCATION: 10...10
<223> OTHER INFORMATION: Xaa is any amino acid

<400> SEQUENCE: 5

Lys Xaa Xaa Xaa Pro Ser Glu Phe Xaa Xaa Asp
1               5                   10

<210> SEQ ID NO 6
<211> LENGTH: 8
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: 1...1
<223> OTHER INFORMATION: Xaa is Asp or Asn
<220> FEATURE:
<221> NAME/KEY: misc_feature
<222> LOCATION: 3...3
<223> OTHER INFORMATION: Xaa is any amino acid residue
<220> FEATURE:
<221> NAME/KEY: misc_feature
<222> LOCATION: 4...4
<223> OTHER INFORMATION: Xaa is Arg, Lys, Asn or Gln
<220> FEATURE:
<221> NAME/KEY: misc_feature
<222> LOCATION: 5...5
<223> OTHER INFORMATION: Xaa is Ala, Gly, Ser or Thr

<400> SEQUENCE: 6

Xaa Asp Xaa Xaa Xaa Leu Asn Lys
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: 1...1
<223> OTHER INFORMATION: Xaa is Ala, Gly, Val, Ile, Met or Leu
<220> FEATURE:
<221> NAME/KEY: misc_feature
<222> LOCATION: (4)...(5)
<223> OTHER INFORMATION: Xaa is a charged amino acid residue
<220> FEATURE:
<221> NAME/KEY: misc_feature
<222> LOCATION: 6...6
<223> OTHER INFORMATION: Xaa is any amino acid residue
<220> FEATURE:
<221> NAME/KEY: misc_feature
<222> LOCATION: 7...7
<223> OTHER INFORMATION: Xaa is Phe or Tyr

<400> SEQUENCE: 7

Xaa Tyr Pro Xaa Xaa Xaa Xaa
1               5

<210> SEQ ID NO 8
```

```
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (2)...(3)
<223> OTHER INFORMATION: Xaa is Met, Ile, Val, or Leu
<220> FEATURE:
<221> NAME/KEY: misc_feature
<222> LOCATION: 5...5
<223> OTHER INFORMATION: Xaa is Ala or Gly
<220> FEATURE:
<221> NAME/KEY: misc_feature
<222> LOCATION: 8...8
<223> OTHER INFORMATION: Xaa is Phe or Tyr
<220> FEATURE:
<221> NAME/KEY: misc_feature
<222> LOCATION: 9...9
<223> OTHER INFORMATION: Xaa is Met, Ile, Val, or Leu
<220> FEATURE:
<221> NAME/KEY: misc_feature
<222> LOCATION: 11...11
<223> OTHER INFORMATION: Xaa is Gln or Asn

<400> SEQUENCE: 8

Leu Xaa Xaa Gly Xaa Thr Gly Xaa Xaa Gly Xaa
 1               5                  10

<210> SEQ ID NO 9
<211> LENGTH: 11
<212> TYPE: PRT
<213> ORGANISM: Artificial sequence
<220> FEATURE:
<223> OTHER INFORMATION: Synthetic construct

<400> SEQUENCE: 9

Leu Val Val Gly Gly Thr Gly Phe Ile Gly Gln
 1               5                  10

<210> SEQ ID NO 10
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: 2...2
<223> OTHER INFORMATION: Xaa is Arg or Lys
<220> FEATURE:
<221> NAME/KEY: misc_feature
<222> LOCATION: (3)...(4)
<223> OTHER INFORMATION: Xaa is Phe or Tyr
<220> FEATURE:
<221> NAME/KEY: misc_feature
<222> LOCATION: 9...9
<223> OTHER INFORMATION: Xaa is Ala or Gly
<220> FEATURE:
<221> NAME/KEY: misc_feature
<222> LOCATION: 10...10
<223> OTHER INFORMATION: Xaa is a basic or half-basic amino acid

<400> SEQUENCE: 10

Lys Xaa Xaa Xaa Pro Ser Glu Phe Xaa Xaa Asp
 1               5                  10

<210> SEQ ID NO 11
<211> LENGTH: 11
<212> TYPE: PRT
<213> ORGANISM: Artificial sequence
<220> FEATURE:
```

<223> OTHER INFORMATION: Synthetic construct

<400> SEQUENCE: 11

Lys Lys Phe Leu Pro Ser Glu Phe Gly His Asp
1               5                   10

<210> SEQ ID NO 12
<211> LENGTH: 8
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: 1...1
<223> OTHER INFORMATION: Xaa is Asp or Asn
<220> FEATURE:
<221> NAME/KEY: misc_feature
<222> LOCATION: 3...3
<223> OTHER INFORMATION: Xaa is Met, Ile, Val or Leu
<220> FEATURE:
<221> NAME/KEY: misc_feature
<222> LOCATION: 4...4
<223> OTHER INFORMATION: Xaa is Arg or Lys
<220> FEATURE:
<221> NAME/KEY: misc_feature
<222> LOCATION: 5...5
<223> OTHER INFORMATION: Xaa is Ser or Thr

<400> SEQUENCE: 12

Xaa Asp Xaa Xaa Xaa Leu Asn Lys
1               5

<210> SEQ ID NO 13
<211> LENGTH: 8
<212> TYPE: PRT
<213> ORGANISM: Artificial sequence
<220> FEATURE:
<223> OTHER INFORMATION: Synthetic construct

<400> SEQUENCE: 13

Asp Asp Ile Arg Thr Leu Asn Lys
1               5

<210> SEQ ID NO 14
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: 1...1
<223> OTHER INFORMATION: Xaa is Val, Ile, Met or Leu
<220> FEATURE:
<221> NAME/KEY: misc_feature
<222> LOCATION: (4)...(5)
<223> OTHER INFORMATION: Xaa is Asp or Glu
<220> FEATURE:
<221> NAME/KEY: misc_feature
<222> LOCATION: 6...6
<223> OTHER INFORMATION: Xaa is Arg or Lys
<220> FEATURE:
<221> NAME/KEY: misc_feature
<222> LOCATION: 7...7
<223> OTHER INFORMATION: Xaa is Phe or Tyr

<400> SEQUENCE: 14

Xaa Tyr Pro Xaa Xaa Xaa Xaa
1               5

```
<210> SEQ ID NO 15
<211> LENGTH: 7
<212> TYPE: PRT
<213> ORGANISM: Artificial sequence
<220> FEATURE:
<223> OTHER INFORMATION: Synthetic construct

<400> SEQUENCE: 15

Leu Tyr Pro Asp Glu Lys Phe
1               5

<210> SEQ ID NO 16
<211> LENGTH: 12
<212> TYPE: PRT
<213> ORGANISM: Desmodium uncinatum
<220> FEATURE:
<221> NAME/KEY: misc_feature
<222> LOCATION: 2...2
<223> OTHER INFORMATION: Xaa is Leu or Ile

<400> SEQUENCE: 16

Phe Xaa Pro Ser Glu Phe Gly His Asp Val Asp Arg
1               5                   10

<210> SEQ ID NO 17
<211> LENGTH: 5
<212> TYPE: PRT
<213> ORGANISM: Desmodium uncinatum
<220> FEATURE:
<221> NAME/KEY: misc_feature
<222> LOCATION: 4...4
<223> OTHER INFORMATION: Xaa is Leu or Ile

<400> SEQUENCE: 17

Ala Tyr Phe Xaa Asp
1               5

<210> SEQ ID NO 18
<211> LENGTH: 15
<212> TYPE: PRT
<213> ORGANISM: Desmodium uncinatum
<220> FEATURE:
<221> NAME/KEY: misc_feature
<222> LOCATION: (4)...(10)
<223> OTHER INFORMATION: Xaa is Leu or Ile

<400> SEQUENCE: 18

Glu Tyr Glu Xaa Asp Val Val Xaa Ser Xaa Val Gly Gly Ala Arg
1               5                   10                  15

<210> SEQ ID NO 19
<211> LENGTH: 16
<212> TYPE: PRT
<213> ORGANISM: Desmodium uncinatum
<220> FEATURE:
<221> NAME/KEY: misc_feature
<222> LOCATION: (2)...(14)
<223> OTHER INFORMATION: Xaa is Leu or Ile

<400> SEQUENCE: 19

Thr Xaa Val Val Gly Gly Thr Gly Phe Xaa Gly Gln Phe Xaa Thr Lys
1               5                   10                  15

<210> SEQ ID NO 20
<211> LENGTH: 12
<212> TYPE: PRT
<213> ORGANISM: Desmodium uncinatum
<220> FEATURE:
<221> NAME/KEY: misc_feature
```

```
<222> LOCATION: (1)...(10)
<223> OTHER INFORMATION: Xaa is Leu or Ile

<400> SEQUENCE: 20

Xaa G

```
<221> NAME/KEY: misc_feature
<222> LOCATION: (3)...(18)
<223> OTHER INFORMATION: n is inosine

<400> SEQUENCE: 24
ggnttyggnt ayccnacntt y                                              21

<210> SEQ ID NO 25
<211> LENGTH: 30
<212> TYPE: DNA
<213> ORGANISM: Artificial sequence
<220> FEATURE:
<223> OTHER INFORMATION: primer of the Desmodium uncinatum LAR gene
<220> FEATURE:
<221> NAME/KEY: misc_feature
<222> LOCATION: (4)...(24)
<223> OTHER INFORMATION: n is inosine

<400> SEQUENCE: 25
yttnanngcy tcnannanng tnanytgrtc                                     30

<210> SEQ ID NO 26
<211> LENGTH: 228
<212> TYPE: DNA
<213> ORGANISM: Artificial sequence
<220> FEATURE:
<223> OTHER INFORMATION: primer of the Desmodium uncinatum LAR gene
<220> FEATURE:
<221> NAME/KEY: CDS
<222> LOCATION: (1)..(228)
<223> OTHER INFORMATION:

<400> SEQUENCE: 26 ggg ttc ggt tat ccg acg ttt ttg ctc gta agg cca gga cct gtc tca      48
Gly Phe Gly Tyr Pro Thr Phe Leu Leu Val Arg Pro Gly Pro Val Ser
1               5                   10                  15 cct tcc aag gct gtc att atc aaa acc ttt caa gac aaa ggt gct aag      96
Pro Ser Lys Ala Val Ile Ile Lys Thr Phe Gln Asp Lys Gly Ala Lys
            20                  25                  30 gtt atc tat ggc gta att aat gac aag gaa tgc atg gag aag att ttg     144
Val Ile Tyr Gly Val Ile Asn Asp Lys Glu Cys Met Glu Lys Ile Leu
        35                  40                  45 aag gag tac gag att gat gtc gtc att tct ctt gta gga ggc gca cga     192
Lys Glu Tyr Glu Ile Asp Val Val Ile Ser Leu Val Gly Gly Ala Arg
    50                  55                  60 cta ttg gac cag ctc acc ctc ctc gag gcc ctc aaa                     228
Leu Leu Asp Gln Leu Thr Leu Leu Glu Ala Leu Lys
65                  70                  75

<210> SEQ ID NO 27
<211> LENGTH: 76
<212> TYPE: PRT
<213> ORGANISM: Artificial sequence
<220> FEATURE:
<223> OTHER INFORMATION: Desmodium uncinatum LAR gene

<400> SEQUENCE: 27

Gly Phe Gly Tyr Pro Thr Phe Leu Leu Val Arg Pro Gly Pro Val Ser
1               5                   10                  15

Pro Ser Lys Ala Val Ile Ile Lys Thr Phe Gln Asp Lys Gly Ala Lys
            20                  25                  30

Val Ile Tyr Gly Val Ile Asn Asp Lys Glu Cys Met Glu Lys Ile Leu
        35                  40                  45

Lys Glu Tyr Glu Ile Asp Val Val Ile Ser Leu Val Gly Gly Ala Arg
    50                  55                  60
```

```
Leu Leu Asp Gln Leu Thr Leu Leu Glu Ala Leu Lys
65              70                  75

<210> SEQ ID NO 28
<211> LENGTH: 1652
<212> TYPE: DNA
<213> ORGANISM: Desmodium uncinatum
<220> FEATURE:
<221> NAME/KEY: CDS
<222> LOCATION: (122)..(1267)
<223> OTHER INFORMATION: n is any nucleotide residue

<400> SEQUENCE: 28
gcctcaactc actttgtgt gatacgctcc aagcaaaagc tagctaagaa caagaaaata      60
tacatagaaa agcaagatcc gaggttgttg gaaaaaataa attgagaaag aagaagaaaa     120 t atg acg gta tcg ggt gca att cct tca atg acc aag aac cga act ttg    169
  Met Thr Val Ser Gly Ala Ile Pro Ser Met Thr Lys Asn Arg Thr Leu
  1               5                  10                  15 gtg gtc gga gga act ggg ttc ata ggt cag ttc ata act aag gca agt      217
Val Val Gly Gly Thr Gly Phe Ile Gly Gln Phe Ile Thr Lys Ala Ser
            20                  25                  30 ctt ggc ttt ggg tac cct acc ttt ttg ctc gta agg cca gga cct gtc      265
Leu Gly Phe Gly Tyr Pro Thr Phe Leu Leu Val Arg Pro Gly Pro Val
        35                  40                  45 tca cct tcc aag gct gtc att atc aaa acc ttt caa gac aaa ggt gct      313
Ser Pro Ser Lys Ala Val Ile Ile Lys Thr Phe Gln Asp Lys Gly Ala
    50                  55                  60 aag gtt atc tat ggt gta att aat gac aag gaa tgc atg gag aag att      361
Lys Val Ile Tyr Gly Val Ile Asn Asp Lys Glu Cys Met Glu Lys Ile
65                  70                  75                  80 ttg aag gag tac gag att gat gtc gtc att tct ctt gta gga ggc gca      409
Leu Lys Glu Tyr Glu Ile Asp Val Val Ile Ser Leu Val Gly Gly Ala
                85                  90                  95 cga cta ttg gat cag ctt acc ttg ttg gag gcc ata aaa tct gtg aag      457
Arg Leu Leu Asp Gln Leu Thr Leu Leu Glu Ala Ile Lys Ser Val Lys
            100                 105                 110 act atc aag agg ttt ctg cct tca gag ttt ggg cac gat gtg gat agg      505
Thr Ile Lys Arg Phe Leu Pro Ser Glu Phe Gly His Asp Val Asp Arg
        115                 120                 125 aca gat cct gta gag cca gga ttg aca atg tac aaa gag aag cgt ttg      553
Thr Asp Pro Val Glu Pro Gly Leu Thr Met Tyr Lys Glu Lys Arg Leu
    130                 135                 140 gtt agg cgt gct gtt gag gaa tat ggg att cct ttc acc aac att tgc      601
Val Arg Arg Ala Val Glu Glu Tyr Gly Ile Pro Phe Thr Asn Ile Cys
145                 150                 155                 160 tgc aac tcc att gct tct tgg cct tat tat gac aat tgt cac cct tcc      649
Cys Asn Ser Ile Ala Ser Trp Pro Tyr Tyr Asp Asn Cys His Pro Ser
                165                 170                 175 cag gtc cct cca ccc atg gat cag ttt caa atc tat ggt gat ggc aac      697
Gln Val Pro Pro Pro Met Asp Gln Phe Gln Ile Tyr Gly Asp Gly Asn
            180                 185                 190 acc aaa gct tac ttc att gat ggc aat gat att gga aag ttc aca atg      745
Thr Lys Ala Tyr Phe Ile Asp Gly Asn Asp Ile Gly Lys Phe Thr Met
        195                 200                 205 aag acc att gat gat atc aga aca ctg aac aaa aat gtt cat ttt cga      793
Lys Thr Ile Asp Asp Ile Arg Thr Leu Asn Lys Asn Val His Phe Arg
    210                 215                 220 ccc tcg agc aac tgt tat tcc atc aat gaa ctt gct tct tta tgg gaa      841
Pro Ser Ser Asn Cys Tyr Ser Ile Asn Glu Leu Ala Ser Leu Trp Glu
225                 230                 235                 240
```

```
aag aaa att gga cgt aca ctt ccc aga ttc acc gta aca gcg gat aaa      889
Lys Lys Ile Gly Arg Thr Leu Pro Arg Phe Thr Val Thr Ala Asp Lys
            245                 250                 255 ctt ctt gct cat gct gca gaa aat att ata cca gaa agt att gta tca      937
Leu Leu Ala His Ala Ala Glu Asn Ile Ile Pro Glu Ser Ile Val Ser
        260                 265                 270 tcg ttc acc cat gat att ttc atc aac ggt tgc caa gtt aac ttc agc      985
Ser Phe Thr His Asp Ile Phe Ile Asn Gly Cys Gln Val Asn Phe Ser
    275                 280                 285 ata gat gaa cat agt gat gtt gag att gac aca ctc tat cca gat gaa     1033
Ile Asp Glu His Ser Asp Val Glu Ile Asp Thr Leu Tyr Pro Asp Glu
290                 295                 300 aaa ttt cga tcc ttg gac gat tgc tat gag gac ttt gtt ccc atg gtc     1081
Lys Phe Arg Ser Leu Asp Asp Cys Tyr Glu Asp Phe Val Pro Met Val
305                 310                 315                 320 cat gac aag att cat gca gga aaa agt gga gaa att aaa att aaa gat     1129
His Asp Lys Ile His Ala Gly Lys Ser Gly Glu Ile Lys Ile Lys Asp
                325                 330                 335 gga aag ccc ttg gta cag acc gga aca att gaa gaa att aat aag gac     1177
Gly Lys Pro Leu Val Gln Thr Gly Thr Ile Glu Glu Ile Asn Lys Asp
            340                 345                 350 ata aag act ttg gta gag aca caa cca aat gaa gaa att aaa aag gat     1225
Ile Lys Thr Leu Val Glu Thr Gln Pro Asn Glu Glu Ile Lys Lys Asp
        355                 360                 365 atg aag gct ttg gta gag gca gtg cca att tca gct atg ggc             1267
Met Lys Ala Leu Val Glu Ala Val Pro Ile Ser Ala Met Gly
    370                 375                 380 tagttgaaaa tgaaccacct taatatttc tgttcccact                           1307 ttcatggact ttggtggagg cagaaattca ttatattcat gaataatttt agaatcttat    1367
tcaaaaggtc ccctggtttg tttctattca gatcaaacta tttcatattc acctaaataa    1427
ttagtttgat tttctgatcg aactagttat ggatgttgca tgtcttgcat ggctacaata    1487
agttctagtc tattggtctt ggttctactc ttttagattt aattactacc ttatgcttgc    1547
tatgggatca aattttcaga atgtacgtat gtacggttga aatgtccttt tgtggttaat    1607
gaattttatc tgtccttatt gatgatgtat tcnatatatt attga                    1652

<210> SEQ ID NO 29
<211> LENGTH: 382
<212> TYPE: PRT
<213> ORGANISM: Desmodium uncinatum

<400> SEQUENCE: 29

Met Thr Val Ser Gly Ala Ile Pro Ser Met Thr Lys Asn Arg Thr Leu
1               5                   10                  15

Val Val Gly Gly Thr Gly Phe Ile Gly Gln Phe Ile Thr Lys Ala Ser
            20                  25                  30

Leu Gly Phe Gly Tyr Pro Thr Phe Leu Leu Val Arg Pro Gly Pro Val
        35                  40                  45

Ser Pro Ser Lys Ala Val Ile Ile Lys Thr Phe Gln Asp Lys Gly Ala
    50                  55                  60

Lys Val Ile Tyr Gly Val Ile Asn Asp Lys Glu Cys Met Glu Lys Ile
65                  70                  75                  80

Leu Lys Glu Tyr Glu Ile Asp Val Val Ile Ser Leu Val Gly Gly Ala
                85                  90                  95

Arg Leu Leu Asp Gln Leu Thr Leu Leu Glu Ala Ile Lys Ser Val Lys
            100                 105                 110
```

```
Thr Ile Lys Arg Phe Leu Pro Ser Glu Phe Gly His Asp Val Asp Arg
        115                 120                 125

Thr Asp Pro Val Glu Pro Gly Leu Thr Met Tyr Lys Glu Lys Arg Leu
    130                 135                 140

Val Arg Arg Ala Val Glu Glu Tyr Gly Ile Pro Phe Thr Asn Ile Cys
145                 150                 155                 160

Cys Asn Ser Ile Ala Ser Trp Pro Tyr Tyr Asp Asn Cys His Pro Ser
                165                 170                 175

Gln Val Pro Pro Met Asp Gln Phe Gln Ile Tyr Gly Asp Gly Asn
            180                 185                 190

Thr Lys Ala Tyr Phe Ile Asp Gly Asn Asp Ile Gly Lys Phe Thr Met
        195                 200                 205

Lys Thr Ile Asp Asp Ile Arg Thr Leu Asn Lys Asn Val His Phe Arg
        210                 215                 220

Pro Ser Ser Asn Cys Tyr Ser Ile Asn Glu Leu Ala Ser Leu Trp Glu
225                 230                 235                 240

Lys Lys Ile Gly Arg Thr Leu Pro Arg Phe Thr Val Thr Ala Asp Lys
                245                 250                 255

Leu Leu Ala His Ala Ala Glu Asn Ile Ile Pro Glu Ser Ile Val Ser
                260                 265                 270

Ser Phe Thr His Asp Ile Phe Ile Asn Gly Cys Gln Val Asn Phe Ser
        275                 280                 285

Ile Asp Glu His Ser Asp Val Glu Ile Asp Thr Leu Tyr Pro Asp Glu
        290                 295                 300

Lys Phe Arg Ser Leu Asp Asp Cys Tyr Glu Asp Phe Val Pro Met Val
305                 310                 315                 320

His Asp Lys Ile His Ala Gly Lys Ser Gly Glu Ile Lys Ile Lys Asp
                325                 330                 335

Gly Lys Pro Leu Val Gln Thr Gly Thr Ile Glu Glu Ile Asn Lys Asp
            340                 345                 350

Ile Lys Thr Leu Val Glu Thr Gln Pro Asn Glu Glu Ile Lys Lys Asp
        355                 360                 365

Met Lys Ala Leu Val Glu Ala Val Pro Ile Ser Ala Met Gly
        370                 375                 380

<210> SEQ ID NO 30
<211> LENGTH: 18
<212> TYPE: PRT
<213> ORGANISM: Artificial sequence
<220> FEATURE:
<223> OTHER INFORMATION: Synthetic construct

<400> SEQUENCE: 30

His Asp Lys Ile His Ala Gly Lys Ser Gly Glu Ile Lys Ile Lys Asp
1               5                   10                  15

Gly Lys

<210> SEQ ID NO 31
<211> LENGTH: 21
<212> TYPE: PRT
<213> ORGANISM: Artificial sequence
<220> FEATURE:
<223> OTHER INFORMATION: Synthetic construct

<400> SEQUENCE: 31

Asn Lys Asp Ile Lys Thr Leu Val Glu Thr Gln Pro Asn Glu Glu Ile
1               5                   10                  15
```

Lys Lys Asp Met Lys
            20

<210> SEQ ID NO 32
<211> LENGTH: 318
<212> TYPE: PRT
<213> ORGANISM: Medicago truncatula

<400> SEQUENCE: 32

Met Ala Thr Glu Asn Lys Ile Leu Ile Leu Gly Pro Thr Gly Ala Ile
1               5                   10                  15

Gly Arg His Ile Val Trp Ala Ser Ile Lys Ala Gly Asn Pro Thr Tyr
            20                  25                  30

Ala Leu Val Arg Lys Thr Pro Gly Asn Val Asn Lys Pro Lys Leu Ile
        35                  40                  45

Thr Ala Ala Asn Pro Glu Thr Lys Glu Glu Leu Ile Asp Asn Tyr Gln
    50                  55                  60

Ser Leu Gly Val Ile Leu Leu Glu Gly Asp Ile Asn Asp His Glu Thr
65                  70                  75                  80

Leu Val Lys Ala Ile Lys Gln Val Asp Ile Val Ile Cys Ala Ala Gly
                85                  90                  95

Arg Leu Leu Ile Glu Asp Gln Val Lys Ile Ile Lys Ala Ile Lys Glu
            100                 105                 110

Ala Gly Asn Val Lys Lys Phe Phe Pro Ser Glu Phe Gly Leu Asp Val
        115                 120                 125

Asp Arg His Glu Ala Val Glu Pro Val Arg Gln Val Phe Glu Glu Lys
    130                 135                 140

Ala Ser Ile Arg Arg Val Ile Glu Ala Glu Gly Val Pro Tyr Thr Tyr
145                 150                 155                 160

Leu Cys Cys His Ala Phe Thr Gly Tyr Phe Leu Arg Asn Leu Ala Gln
                165                 170                 175

Leu Asp Val Thr Asp Pro Pro Arg Asp Lys Val Val Ile Leu Gly Asp
            180                 185                 190

Gly Asn Val Lys Gly Ala Tyr Val Thr Glu Ala Asp Val Gly Thr Phe
        195                 200                 205

Thr Ile Lys Ala Ala Asn Asp Pro Asn Thr Leu Asn Lys Ala Val His
    210                 215                 220

Ile Arg Leu Pro Lys Asn Tyr Leu Thr Gln Asn Glu Val Ile Ser Leu
225                 230                 235                 240

Trp Glu Lys Lys Ile Gly Lys Thr Leu Glu Lys Thr Tyr Val Ser Glu
                245                 250                 255

Glu Gln Val Leu Lys Asp Ile Gln Glu Ser Ser Phe Pro His Asn Tyr
            260                 265                 270

Leu Leu Ala Leu Tyr His Ser Gln Gln Ile Lys Gly Asp Ala Val Tyr
        275                 280                 285

Glu Ile Asp Pro Thr Lys Asp Ile Glu Ala Ser Glu Ala Tyr Pro Asp
    290                 295                 300

Val Thr Tyr Thr Thr Ala Asp Glu Tyr Leu Asn Gln Phe Val
305                 310                 315

<210> SEQ ID NO 33
<211> LENGTH: 312
<212> TYPE: PRT
<213> ORGANISM: Lupinis albus

<400> SEQUENCE: 33

-continued

```
Met Gly Lys Ser Lys Val Leu Val Gly Gly Thr Gly Tyr Val Gly
1               5                   10                  15

Arg Arg Ile Val Lys Ala Ser Leu Glu His Gly His Glu Thr Phe Ile
            20                  25                  30

Leu Gln Arg Pro Glu Ile Gly Leu Asp Ile Glu Lys Leu Gln Ile Leu
            35                  40                  45

Leu Ser Phe Lys Lys Gln Gly Ala Ile Leu Val Glu Ala Ser Phe Ser
    50                  55                  60

Asp His Lys Ser Leu Val Asp Ala Val Lys Leu Val Asp Val Ile
65                  70                  75                  80

Cys Thr Met Ser Gly Val His Phe Arg Ser His Asn Leu Leu Thr Gln
                85                  90                  95

Leu Lys Leu Val Glu Ala Ile Lys Asp Ala Gly Asn Ile Lys Arg Phe
            100                 105                 110

Leu Pro Ser Glu Phe Gly Met Asp Pro Ala Leu Met Gly His Ala Leu
            115                 120                 125

Glu Pro Gly Arg Val Thr Phe Asp Glu Lys Met Thr Val Arg Lys Ala
130                 135                 140

Ile Glu Glu Ala Asn Ile Pro Phe Thr Tyr Ile Ser Ala Asn Cys Phe
145                 150                 155                 160

Ala Gly Tyr Phe Ala Gly Asn Leu Ser Gln Met Lys Thr Leu Leu Pro
                165                 170                 175

Pro Arg Asp Lys Val Leu Leu Tyr Gly Asp Gly Asn Val Lys Pro Val
            180                 185                 190

Tyr Met Asp Glu Asp Val Ala Thr Tyr Thr Ile Lys Thr Ile Asp
            195                 200                 205

Asp Pro Arg Thr Leu Asn Lys Thr Val Tyr Leu Arg Pro Pro Glu Asn
            210                 215                 220

Ile Leu Thr His Lys Glu Leu Ile Glu Lys Trp Glu Glu Leu Ile Gly
225                 230                 235                 240

Lys Gln Leu Glu Lys Asn Ser Ile Ser Glu Lys Asp Phe Leu Ser Thr
            245                 250                 255

Leu Lys Gly Leu Asp Phe Ala Ser Gln Val Gly Val Gly His Phe Tyr
            260                 265                 270

His Ile Phe Tyr Glu Gly Cys Leu Thr Asn Phe Glu Ile Gly Glu Asn
            275                 280                 285

Gly Glu Glu Ala Ser Glu Leu Tyr Pro Glu Val Asn Tyr Thr Arg Met
            290                 295                 300

Asp Gln Tyr Leu Lys Val Tyr Val
305                 310

<210> SEQ ID NO 34
<211> LENGTH: 318
<212> TYPE: PRT
<213> ORGANISM: Pisum sativum

<400> SEQUENCE: 34

Met Ala Thr Glu Asn Lys Ile Leu Ile Leu Gly Ala Thr Gly Ala Ile
1               5                   10                  15

Gly Arg His Ile Val Trp Ala Ser Ile Lys Ala Gly Asn Pro Thr Tyr
            20                  25                  30

Ala Leu Val Arg Lys Thr Ser Asp Asn Val Asn Lys Pro Lys Leu Thr
            35                  40                  45

Glu Ala Ala Asn Pro Glu Thr Lys Glu Glu Leu Leu Lys Asn Tyr Gln
```

```
                 50                  55                  60
Ala Ser Gly Val Ile Leu Leu Glu Gly Asp Ile Asn Asp His Glu Thr
 65                  70                  75                  80

Leu Val Asn Ala Ile Lys Gln Val Asp Thr Val Ile Cys Ala Ala Gly
                 85                  90                  95

Arg Leu Leu Ile Glu Asp Gln Val Lys Val Ile Lys Ala Ile Lys Glu
                100                 105                 110

Ala Gly Asn Val Lys Arg Phe Phe Pro Ser Glu Phe Gly Leu Asp Val
                115                 120                 125

Asp Arg His Asp Ala Val Glu Pro Val Arg Gln Val Phe Glu Glu Lys
130                 135                 140

Ala Ser Ile Arg Arg Val Val Glu Ser Glu Gly Val Pro Tyr Thr Tyr
145                 150                 155                 160

Leu Cys Cys His Ala Phe Thr Gly Tyr Phe Leu Arg Asn Leu Ala Gln
                165                 170                 175

Ile Asp Ala Thr Asp Pro Pro Arg Asp Lys Val Val Ile Leu Gly Asp
                180                 185                 190

Gly Asn Val Arg Gly Ala Tyr Val Thr Glu Ala Asp Val Gly Thr Tyr
                195                 200                 205

Thr Ile Arg Ala Ala Asn Asp Pro Asn Thr Leu Asn Lys Ala Val His
                210                 215                 220

Ile Arg Leu Pro Asn Asn Tyr Leu Thr Ala Asn Glu Val Ile Ala Leu
225                 230                 235                 240

Trp Glu Lys Lys Ile Gly Lys Thr Leu Glu Lys Thr Tyr Val Ser Glu
                245                 250                 255

Glu Gln Val Leu Lys Asp Ile Gln Thr Ser Ser Phe Pro His Asn Tyr
                260                 265                 270

Leu Leu Ala Leu Tyr His Ser Gln Gln Ile Lys Gly Asp Ala Val Tyr
                275                 280                 285

Glu Ile Asp Pro Ala Lys Asp Val Glu Ala Tyr Asp Ala Tyr Pro Asp
                290                 295                 300

Val Lys Tyr Thr Thr Ala Asp Glu Tyr Leu Asn Gln Phe Val
305                 310                 315

<210> SEQ ID NO 35
<211> LENGTH: 307
<212> TYPE: PRT
<213> ORGANISM: Glycine max

<400> SEQUENCE: 35

Met Ala Ala Lys Ser Lys Ile Leu Val Ile Gly Gly Thr Gly Tyr Ile
 1               5                  10                  15

Gly Lys Phe Ile Val Lys Ala Ser Ser Glu Ala Gly His Pro Thr Phe
                20                  25                  30

Ala Leu Val Arg Glu Ser Thr Leu Ser His Pro Glu Lys Phe Lys Leu
                35                  40                  45

Ile Glu Ser Phe Lys Thr Ser Gly Val Thr Leu Leu Tyr Gly Asp Leu
                50                  55                  60

Thr Asp His Glu Ser Leu Val Lys Ala Ile Lys Gln Val Asp Val Val
 65                 70                  75                  80

Ile Ser Ala Leu Gly Ala Glu Gln Ile Asp Asp Gln Val Lys Ile Ile
                85                  90                  95

Ala Ala Ile Lys Glu Ala Gly Asn Ile Lys Arg Leu Leu Pro Ser Glu
                100                 105                 110
```

```
Phe Gly His Asp Val Asp His His Asn Ala Val Glu Pro Val Ser Ser
        115                 120                 125

Phe Phe Glu Lys Lys Val Lys Ile Arg Arg Ala Ile Glu Ala Glu Gly
    130                 135                 140

Ile Pro Tyr Thr Tyr Ile Ser Ser Asn Ser Phe Ala Gly His Phe Leu
145                 150                 155                 160

Pro Asn Leu Leu Gln Gln Asn Val Thr Ala Pro Pro Arg Asp Glu Val
                165                 170                 175

Val Ile Leu Gly Asp Gly Asn Ile Lys Gly Val Tyr Val Ile Glu Glu
            180                 185                 190

Asp Val Ala Thr Tyr Thr Ile Lys Ala Val Asp Asp Pro Arg Thr Leu
        195                 200                 205

Asn Lys Thr Leu Tyr Leu Arg Pro His Ala Asn Val Leu Thr Phe Asn
    210                 215                 220

Glu Leu Val Ser Leu Trp Glu Asn Lys Ile Lys Ser Ser Leu Asp Lys
225                 230                 235                 240

Ile Tyr Val Pro Glu Asp Gln Leu Leu Lys Ser Ile Gln Glu Ser Ser
                245                 250                 255

Phe Pro Ala Asn Phe Met Leu Ala Leu Gly His Ser Met Leu Val Lys
            260                 265                 270

Gly Asp Cys Asn Tyr Glu Ile Asp Pro Ser Phe Gly Val Glu Ala Ser
        275                 280                 285

Lys Leu Tyr Pro Glu Val Lys Tyr Thr Thr Val Asp Asn Tyr Leu Asn
    290                 295                 300

Ala Phe Val
305

<210> SEQ ID NO 36
<211> LENGTH: 318
<212> TYPE: PRT
<213> ORGANISM: Cicer arietinum

<400> SEQUENCE: 36

Met Ala Ser Gln Asn Arg Ile Leu Val Leu Gly Pro Thr Gly Ala Ile
1               5                   10                  15

Gly Arg His Val Val Trp Ala Ser Ile Lys Ala Gly Asn Pro Thr Tyr
            20                  25                  30

Ala Leu Ile Arg Lys Thr Pro Gly Asp Ile Asn Lys Pro Ser Leu Val
        35                  40                  45

Ala Ala Ala Asn Pro Glu Ser Lys Glu Glu Leu Leu Gln Ser Phe Lys
    50                  55                  60

Ala Ala Gly Val Ile Leu Leu Glu Gly Asp Met Asn Asp His Glu Ala
65                  70                  75                  80

Leu Val Lys Ala Ile Lys Gln Val Asp Thr Val Ile Cys Thr Phe Gly
                85                  90                  95

Arg Leu Leu Ile Leu Asp Gln Val Lys Ile Ile Lys Ala Ile Lys Glu
            100                 105                 110

Ala Gly Asn Val Lys Arg Phe Phe Pro Ser Glu Phe Gly Leu Asp Val
        115                 120                 125

Asp Arg His Asp Ala Val Asp Pro Val Arg Pro Val Phe Asp Glu Lys
    130                 135                 140

Ala Ser Ile Arg Arg Val Val Glu Ala Glu Gly Val Pro Tyr Thr Tyr
145                 150                 155                 160

Leu Cys Cys His Ala Phe Thr Gly Tyr Phe Leu Arg Asn Leu Ala Gln
                165                 170                 175
```

```
Phe Asp Ala Thr Glu Pro Pro Arg Asp Lys Val Ile Ile Leu Gly Asp
            180                 185                 190

Gly Asn Val Lys Gly Ala Tyr Val Thr Glu Ala Asp Val Gly Thr Tyr
        195                 200                 205

Thr Ile Arg Ala Ala Asn Asp Pro Arg Thr Leu Asn Lys Ala Val His
    210                 215                 220

Ile Arg Leu Pro His Asn Tyr Leu Thr Ser Asn Glu Val Val Ser Leu
225                 230                 235                 240

Trp Glu Lys Lys Ile Gly Lys Thr Leu Glu Lys Ser Tyr Ile Ser Glu
                245                 250                 255

Glu Lys Val Leu Lys Asp Ile Asn Val Ser Thr Phe Pro His Asn Tyr
            260                 265                 270

Leu Leu Ala Leu Tyr His Ser Gln Gln Ile Lys Gly Asp Ala Val Tyr
        275                 280                 285

Glu Ile Asp Pro Ala Lys Asp Ala Glu Ala Tyr Asp Leu Tyr Pro Asp
    290                 295                 300

Val Lys Tyr Thr Thr Ala Asp Glu Tyr Leu Asp Gln Phe Val
305                 310                 315

<210> SEQ ID NO 37
<211> LENGTH: 308
<212> TYPE: PRT
<213> ORGANISM: Solanum tuberosum

<400> SEQUENCE: 37

Met Ala Gly Lys Ser Lys Ile Leu Phe Ile Gly Gly Thr Gly Tyr Ile
1               5                   10                  15

Gly Lys Phe Ile Val Glu Ala Ser Ala Lys Ala Gly His Asp Thr Phe
            20                  25                  30

Val Leu Val Arg Glu Ser Thr Leu Ser Asn Pro Thr Lys Thr Lys Leu
        35                  40                  45

Ile Asp Thr Phe Lys Ser Phe Gly Val Thr Phe Val His Gly Asp Leu
    50                  55                  60

Tyr Asp His Glu Ser Leu Val Lys Ala Ile Lys Gln Val Asp Val Val
65                  70                  75                  80

Ile Ser Thr Val Gly His Ala Leu Leu Ala Asp Gln Val Lys Leu Ile
                85                  90                  95

Ala Ala Ile Lys Glu Ala Gly Asn Val Lys Arg Phe Phe Pro Ser Glu
            100                 105                 110

Phe Gly Asn Asp Val Asp Arg Val His Ala Val Glu Pro Ala Lys Ala
        115                 120                 125

Ala Phe Asn Thr Lys Ala Gln Ile Arg Arg Val Glu Ala Glu Gly
    130                 135                 140

Ile Pro Phe Thr Tyr Val Ala Thr Phe Phe Ala Gly Tyr Ser Leu
145                 150                 155                 160

Pro Asn Leu Ala Gln Pro Gly Ala Ala Gly Pro Asn Asp Lys Val
                165                 170                 175

Val Ile Leu Gly His Gly Asn Thr Lys Ala Val Phe Asn Lys Glu Glu
            180                 185                 190

Asp Ile Gly Thr Tyr Thr Ile Asn Ala Val Asp Asp Pro Lys Thr Leu
        195                 200                 205

Asn Lys Ile Leu Tyr Ile Lys Pro Pro His Asn Ile Ile Thr Leu Asn
    210                 215                 220

Glu Leu Val Ser Leu Trp Glu Lys Lys Thr Gly Lys Asn Leu Glu Arg
```

-continued

```
            225                 230                 235                 240
Leu Tyr Val Pro Glu Glu Gln Val Leu Lys Asn Ile Gln Glu Ala Ser
                245                 250                 255
Val Pro Met Asn Val Gly Leu Ser Ile Tyr His Thr Ala Phe Val Lys
            260                 265                 270
Gly Asp His Thr Asn Phe Glu Ile Glu Pro Ser Phe Gly Val Glu Ala
        275                 280                 285
Ser Glu Val Tyr Pro Asp Val Lys Tyr Thr Pro Ile Asp Glu Ile Leu
    290                 295                 300
Asn Gln Tyr Val
305

<210> SEQ ID NO 38
<211> LENGTH: 310
<212> TYPE: PRT
<213> ORGANISM: Nicotiana tabacum

<400> SEQUENCE: 38

Met Val Val Ser Glu Lys Ser Lys Ile Leu Ile Ile Gly Gly Thr Gly
1               5                   10                  15
Tyr Ile Gly Lys Tyr Leu Val Glu Thr Ser Ala Lys Ser Gly His Pro
            20                  25                  30
Thr Phe Ala Leu Ile Arg Glu Ser Thr Leu Lys Asn Pro Glu Lys Ser
        35                  40                  45
Lys Leu Ile Asp Thr Phe Lys Ser Tyr Gly Val Thr Leu Leu Phe Gly
    50                  55                  60
Asp Ile Ser Asn Gln Glu Ser Leu Leu Lys Ala Ile Lys Gln Val Asp
65                  70                  75                  80
Val Val Ile Ser Thr Val Gly Gly Gln Gln Phe Thr Asp Gln Val Asn
                85                  90                  95
Ile Ile Lys Ala Ile Lys Glu Ala Gly Asn Ile Lys Arg Phe Leu Pro
            100                 105                 110
Ser Glu Phe Gly Phe Asp Val Asp His Ala Arg Ala Ile Glu Pro Ala
        115                 120                 125
Ala Ser Leu Phe Ala Leu Lys Val Arg Ile Arg Arg Met Ile Glu Ala
    130                 135                 140
Glu Gly Ile Pro Tyr Thr Tyr Val Ile Cys Asn Trp Phe Ala Asp Phe
145                 150                 155                 160
Phe Leu Pro Asn Leu Gly Gln Leu Glu Ala Lys Thr Pro Pro Arg Asp
                165                 170                 175
Lys Val Val Ile Phe Gly Asp Gly Asn Pro Lys Ala Ile Tyr Val Lys
            180                 185                 190
Glu Glu Asp Ile Ala Thr Tyr Thr Ile Glu Ala Val Asp Asp Pro Arg
        195                 200                 205
Thr Leu Asn Lys Thr Leu His Met Arg Pro Pro Ala Asn Ile Leu Ser
    210                 215                 220
Phe Asn Glu Ile Val Ser Leu Trp Glu Asp Lys Ile Gly Lys Thr Leu
225                 230                 235                 240
Glu Lys Leu Tyr Leu Ser Glu Asp Ile Leu Gln Ile Val Gln Glu
                245                 250                 255
Gly Pro Leu Pro Leu Arg Thr Asn Leu Ala Ile Cys His Ser Val Phe
            260                 265                 270
Val Asn Gly Asp Ser Ala Asn Phe Glu Val Gln Pro Pro Thr Gly Val
        275                 280                 285
```

```
Glu Ala Thr Glu Leu Tyr Pro Lys Val Lys Tyr Thr Thr Val Asp Glu
    290                 295                 300

Phe Tyr Asn Lys Phe Val
305                 310

<210> SEQ ID NO 39
<211> LENGTH: 319
<212> TYPE: PRT
<213> ORGANISM: Arabidopsis thaliana

<400> SEQUENCE: 39

Met Thr Ser Lys Ile Leu Val Ile Gly Ala Thr Gly Leu Ile Gly Lys
1               5                   10                  15

Val Leu Val Glu Glu Ser Ala Lys Ser Gly His Ala Thr Phe Ala Leu
            20                  25                  30

Val Arg Glu Ala Ser Leu Ser Asp Pro Val Lys Ala Gln Leu Val Glu
        35                  40                  45

Arg Phe Lys Asp Leu Gly Val Thr Ile Leu Tyr Val Arg Ser Asn Pro
    50                  55                  60

Leu Leu Met Leu Gly Ser Leu Ser Asp Lys Glu Ser Leu Val Lys Ala
65                  70                  75                  80

Ile Lys Gln Val Asp Val Val Ile Ser Ala Val Gly Arg Phe Gln Thr
                85                  90                  95

Glu Ile Leu Asn Gln Thr Asn Ile Ile Asp Ala Ile Lys Glu Ser Gly
            100                 105                 110

Asn Val Lys Arg Phe Leu Pro Ser Glu Phe Gly Asn Asp Val Asp Arg
        115                 120                 125

Thr Val Ala Ile Glu Pro Thr Leu Ser Glu Phe Ile Thr Lys Ala Gln
    130                 135                 140

Ile Arg Arg Ala Ile Glu Ala Ala Lys Ile Pro Tyr Thr Tyr Val Val
145                 150                 155                 160

Ser Gly Cys Phe Ala Gly Leu Phe Val Pro Cys Leu Gly Gln Cys His
                165                 170                 175

Leu Arg Leu Arg Ser Pro Pro Arg Asp Lys Val Ser Ile Tyr Asp Thr
            180                 185                 190

Gly Asn Gly Lys Ala Ile Val Asn Thr Glu Glu Asp Ile Val Ala Tyr
        195                 200                 205

Thr Leu Lys Ala Val Asp Asp Pro Arg Thr Leu Asn Lys Ile Leu Tyr
    210                 215                 220

Ile His Pro Pro Asn Tyr Ile Val Ser Gln Asn Asp Met Val Gly Leu
225                 230                 235                 240

Trp Glu Glu Lys Ile Gly Lys Thr Leu Glu Lys Thr Tyr Val Ser Glu
                245                 250                 255

Glu Glu Leu Leu Lys Thr Ile Gln Glu Ser Lys Pro Met Asp Phe
            260                 265                 270

Leu Val Gly Leu Ile His Thr Ile Leu Val Lys Ser Asp Phe Thr Ser
        275                 280                 285

Phe Thr Ile Asp Pro Ser Phe Gly Val Glu Ala Ser Glu Leu Tyr Pro
    290                 295                 300

Glu Val Lys Tyr Thr Ser Val Asp Glu Phe Leu Asn Arg Phe Ile
305                 310                 315

<210> SEQ ID NO 40
<211> LENGTH: 308
<212> TYPE: PRT
<213> ORGANISM: Arabidopsis thaliana
```

```
<400> SEQUENCE: 40

Met Thr Ser Lys Ser Lys Ile Leu Phe Ile Gly Gly Thr Gly Tyr Ile
1               5                   10                  15

Gly Lys Tyr Ile Val Glu Ala Ser Ala Arg Ser Gly His Pro Thr Leu
                20                  25                  30

Val Leu Val Arg Asn Ser Thr Leu Thr Ser Pro Ser Arg Ser Ser Thr
                35                  40                  45

Ile Glu Asn Phe Lys Asn Leu Gly Val Gln Phe Leu Leu Gly Asp Leu
    50                  55                  60

Asp Asp His Thr Ser Leu Val Asn Ser Ile Lys Gln Ala Asp Val Val
65                  70                  75                  80

Ile Ser Thr Val Gly His Ser Leu Leu Gly His Gln Tyr Lys Ile Ile
                85                  90                  95

Ser Ala Ile Lys Glu Ala Gly Asn Val Lys Arg Phe Phe Pro Ser Glu
                100                 105                 110

Phe Gly Asn Asp Val Asp Arg Val Phe Thr Val Glu Pro Ala Lys Ser
            115                 120                 125

Ala Tyr Ala Thr Lys Ala Lys Ile Arg Arg Thr Ile Glu Ala Glu Gly
130                 135                 140

Ile Pro Tyr Thr Tyr Val Ser Cys Asn Phe Phe Ala Gly Tyr Phe Leu
145                 150                 155                 160

Pro Thr Leu Ala Gln Pro Gly Ala Thr Ser Ala Pro Arg Asp Lys Val
                165                 170                 175

Ile Val Leu Gly Asp Gly Asn Pro Lys Ala Val Phe Asn Lys Glu Glu
                180                 185                 190

Asp Ile Gly Thr Tyr Thr Ile Asn Ala Val Asp Asp Pro Arg Thr Leu
            195                 200                 205

Asn Lys Ile Leu Tyr Ile Arg Pro Pro Met Asn Thr Tyr Ser Phe Asn
210                 215                 220

Asp Leu Val Ser Leu Trp Glu Asn Lys Ile Gly Lys Thr Leu Glu Arg
225                 230                 235                 240

Ile Tyr Val Pro Glu Glu Gln Leu Leu Lys Gln Ile Ile Glu Ser Ser
                245                 250                 255

Pro Pro Leu Asn Val Met Leu Ser Leu Cys His Cys Val Phe Val Lys
                260                 265                 270

Gly Gly His Thr Ser Phe Glu Ile Glu Pro Ser Phe Gly Val Glu Ala
            275                 280                 285

Ser Glu Leu Tyr Pro Asp Val Lys Tyr Thr Thr Val Asp Glu Ile Leu
            290                 295                 300

Asn Gln Tyr Val
305

<210> SEQ ID NO 41
<211> LENGTH: 308
<212> TYPE: PRT
<213> ORGANISM: Pinus taeda

<400> SEQUENCE: 41

Met Gly Ser Arg Ser Arg Ile Leu Leu Ile Gly Ala Thr Gly Tyr Ile
1               5                   10                  15

Gly Arg His Val Ala Lys Ala Ser Leu Asp Leu Gly His Pro Thr Phe
                20                  25                  30

Leu Leu Val Arg Glu Ser Thr Ala Ser Ser Asn Ser Glu Lys Ala Gln
                35                  40                  45
```

```
Leu Leu Glu Ser Phe Lys Ala Ser Gly Ala Asn Ile Val His Gly Ser
 50                  55                  60

Ile Asp Asp His Ala Ser Leu Val Glu Ala Val Lys Asn Val Asp Val
 65                  70                  75                  80

Val Ile Ser Thr Val Gly Ser Leu Gln Ile Glu Ser Gln Val Asn Ile
                 85                  90                  95

Ile Lys Ala Ile Lys Glu Val Gly Thr Val Lys Arg Phe Phe Pro Ser
            100                 105                 110

Glu Phe Gly Asn Asp Val Asp Asn Val His Ala Val Glu Pro Ala Lys
            115                 120                 125

Ser Val Phe Glu Val Lys Ala Lys Val Arg Arg Ala Ile Glu Ala Glu
        130                 135                 140

Gly Ile Pro Tyr Thr Tyr Val Ser Ser Asn Cys Phe Ala Gly Tyr Phe
145                 150                 155                 160

Leu Arg Ser Leu Ala Gln Ala Gly Leu Thr Ala Pro Pro Arg Asp Lys
                165                 170                 175

Val Val Ile Leu Gly Asp Gly Asn Ala Arg Val Val Phe Val Lys Glu
            180                 185                 190

Glu Asp Ile Gly Thr Phe Thr Ile Lys Ala Val Asp Asp Pro Arg Thr
        195                 200                 205

Leu Asn Lys Thr Leu Tyr Leu Arg Leu Pro Ala Asn Thr Leu Ser Leu
    210                 215                 220

Asn Glu Leu Val Ala Leu Trp Glu Lys Lys Ile Asp Lys Thr Leu Glu
225                 230                 235                 240

Lys Ala Tyr Val Pro Glu Glu Val Leu Lys Leu Ile Ala Asp Thr
                245                 250                 255

Pro Phe Pro Ala Asn Ile Ser Ile Ala Ile Ser His Ser Ile Phe Val
            260                 265                 270

Lys Gly Asp Gln Thr Asn Phe Glu Ile Gly Pro Ala Gly Val Glu Ala
        275                 280                 285

Ser Gln Leu Tyr Pro Asp Val Lys Tyr Thr Thr Val Asp Glu Tyr Leu
    290                 295                 300

Ser Asn Phe Val
305

<210> SEQ ID NO 42
<211> LENGTH: 309
<212> TYPE: PRT
<213> ORGANISM: Tsuga heterophylla

<400> SEQUENCE: 42

Met Ser Arg Val Leu Ile Val Gly Gly Thr Gly Tyr Ile Gly Arg Lys
  1               5                  10                  15

Phe Val Lys Ala Ser Leu Ala Leu Gly His Pro Thr Val Leu Ser
            20                  25                  30

Arg Pro Glu Val Gly Phe Asp Ile Glu Lys Val His Met Leu Leu Ser
        35                  40                  45

Phe Lys Gln Ala Gly Ala Arg Leu Leu Glu Gly Ser Phe Glu Asp Phe
    50                  55                  60

Gln Ser Leu Val Ala Ala Leu Lys Gln Val Asp Val Val Ile Ser Ala
 65                  70                  75                  80

Val Ala Gly Asn His Phe Arg Asn Leu Ile Leu Gln Gln Leu Lys Leu
                 85                  90                  95

Val Glu Ala Ile Lys Glu Ala Arg Asn Ile Lys Arg Phe Leu Pro Ser
```

```
                   100                 105                 110
Glu Phe Gly Met Asp Pro Asp Leu Met Glu His Ala Leu Glu Pro Gly
            115                 120                 125
Asn Ala Val Phe Ile Asp Lys Arg Lys Val Arg Arg Ala Ile Glu Ala
        130                 135                 140
Ala Gly Ile Pro Tyr Thr Tyr Val Ser Ser Asn Ile Phe Ala Gly Tyr
145                 150                 155                 160
Leu Ala Gly Gly Leu Ala Gln Ile Gly Arg Leu Met Pro Pro Arg Asp
                165                 170                 175
Glu Val Val Ile Tyr Gly Asp Gly Asn Val Lys Ala Val Trp Val Asp
            180                 185                 190
Glu Asp Asp Val Gly Ile Tyr Thr Leu Lys Thr Ile Asp Asp Pro Arg
        195                 200                 205
Thr Leu Asn Lys Thr Val Tyr Ile Arg Pro Leu Lys Asn Ile Leu Ser
210                 215                 220
Gln Lys Glu Leu Val Ala Lys Trp Glu Lys Leu Ser Gly Lys Phe Leu
225                 230                 235                 240
Lys Lys Thr Tyr Ile Ser Ala Glu Asp Phe Leu Ala Gly Ile Glu Asp
                245                 250                 255
Gln Pro Tyr Glu His Gln Val Gly Ile Ser His Phe Tyr Gln Met Phe
            260                 265                 270
Tyr Ser Gly Asp Leu Tyr Asn Phe Glu Ile Gly Pro Asp Gly Arg Glu
        275                 280                 285
Ala Thr Met Leu Tyr Pro Glu Val Gln Tyr Thr Thr Met Asp Ser Tyr
    290                 295                 300
Leu Lys Arg Tyr Leu
305
```

<210> SEQ ID NO 43
<211> LENGTH: 314
<212> TYPE: PRT
<213> ORGANISM: Thuja plicata

<400> SEQUENCE: 43

```
Met Asp Lys Lys Ser Arg Val Leu Ile Val Gly Gly Thr Gly Phe Ile
1               5                   10                  15
Gly Lys Arg Ile Val Lys Ala Ser Leu Ala Leu Gly His Pro Thr Tyr
                20                  25                  30
Val Leu Phe Arg Pro Glu Ala Leu Ser Tyr Ile Asp Lys Val Gln Met
            35                  40                  45
Leu Ile Ser Phe Lys Gln Leu Gly Ala Lys Leu Leu Glu Ala Ser Leu
        50                  55                  60
Asp Asp His Gln Gly Leu Val Asp Val Val Lys Gln Val Asp Val Val
65                  70                  75                  80
Ile Ser Ala Val Ser Gly Gly Leu Val Arg His His Ile Leu Asp Gln
                85                  90                  95
Leu Lys Leu Val Glu Ala Ile Lys Glu Ala Gly Asn Ile Lys Arg Phe
            100                 105                 110
Leu Pro Ser Glu Phe Gly Met Asp Pro Asp Val Val Glu Asp Pro Leu
        115                 120                 125
Glu Pro Gly Asn Ile Thr Phe Ile Asp Lys Arg Lys Val Arg Arg Ala
    130                 135                 140
Ile Glu Ala Ala Thr Ile Pro Tyr Thr Tyr Val Ser Ser Asn Met Phe
145                 150                 155                 160
```

```
Ala Gly Phe Phe Ala Gly Ser Leu Ala Gln Leu Gln Asp Ala Pro Arg
                165                 170                 175

Met Met Pro Ala Arg Asp Lys Val Leu Ile Tyr Gly Asp Gly Asn Val
            180                 185                 190

Lys Gly Val Tyr Val Asp Glu Asp Ala Gly Ile Tyr Ile Val Lys
        195                 200                 205

Ser Ile Asp Asp Pro Arg Thr Leu Asn Lys Thr Val Tyr Ile Arg Pro
210                 215                 220

Pro Met Asn Ile Leu Ser Gln Lys Glu Val Val Glu Ile Trp Glu Arg
225                 230                 235                 240

Leu Ser Gly Leu Ser Leu Glu Lys Ile Tyr Val Ser Glu Asp Gln Leu
                245                 250                 255

Leu Asn Met Lys Asp Lys Ser Tyr Val Glu Lys Met Ala Arg Cys His
                260                 265                 270

Leu Tyr His Phe Phe Ile Lys Gly Asp Leu Tyr Asn Phe Glu Ile Gly
            275                 280                 285

Pro Asn Ala Thr Glu Gly Thr Lys Leu Tyr Pro Glu Val Lys Tyr Thr
        290                 295                 300

Thr Met Asp Ser Tyr Met Glu Arg Tyr Leu
305                 310

<210> SEQ ID NO 44
<211> LENGTH: 308
<212> TYPE: PRT
<213> ORGANISM: Tsuga heterophylla

<400> SEQUENCE: 44

Met Gly Ser Ser Arg Ile Leu Ile Ile Gly Ala Thr Gly Tyr Ile
1               5                   10                  15

Gly Arg His Val Ala Lys Ala Ser Leu Asp Leu Gly His Pro Thr Phe
                20                  25                  30

Leu Leu Leu Arg Asp Ser Thr Ser Ser Asn Ser Glu Lys Ala Gln
            35                  40                  45

Leu Val Glu Ser Phe Lys Asp Ser Ser Ala His Ile Leu His Gly Ser
    50                  55                  60

Ile Glu Asp His Ala Ser Leu Val Glu Ala Val Lys Gln Val Asp Val
65                  70                  75                  80

Val Ile Ser Thr Val Gly Thr Gln Gln Ile Glu Lys Gln Val Asn Ile
                85                  90                  95

Ile Lys Gly Ile Lys Glu Val Arg Thr Ile Lys Arg Phe Leu Pro Ser
            100                 105                 110

Glu Phe Arg Asn Asp Val Asp Asn Val His Ala Val Glu Pro Ala Lys
        115                 120                 125

Ser Val Phe Gly Leu Lys Ala Lys Val Arg Arg Ala Ile Glu Ala Glu
    130                 135                 140

Gly Ile Pro Tyr Thr Tyr Val Ser Ser Asn Cys Phe Ala Gly Tyr Phe
145                 150                 155                 160

Ala Ala Asn Leu Ala Gln Ala Gly Leu Lys Thr Pro Lys Asp Lys
                165                 170                 175

Val Val Ile Leu Gly Asp Gly Asn Ala Lys Ala Val Tyr Val Lys Glu
            180                 185                 190

Glu Asp Ile Gly Thr Phe Thr Ile Lys Ala Val Asp Asp Pro Arg Thr
        195                 200                 205

Leu Asn Lys Thr Leu Tyr Leu Arg Leu Pro Ala Asn Thr Leu Ser Phe
    210                 215                 220
```

```
Asn Glu Leu Val Gly Ile Trp Glu Lys Lys Ile Asp Lys Thr Leu Asp
225                 230                 235                 240

Lys Val Tyr Val Pro Glu Glu Val Leu Lys Leu Ile Ala Glu Thr
            245                 250                 255

Pro Phe Pro Gly Asn Ile Ser Ile Ala Ile Arg His Ser Ile Phe Val
            260                 265                 270

Lys Gly Asp Gln Thr Asn Phe Glu Ile Gly Pro Asp Gly Val Glu Ala
            275                 280                 285

Ser Glu Leu Tyr Pro Asp Val Lys Tyr Thr Thr Val Asp Glu Tyr Leu
    290                 295                 300

Ile Lys Phe Val
305

<210> SEQ ID NO 45
<211> LENGTH: 307
<212> TYPE: PRT
<213> ORGANISM: Tsuga heterophylla

<400> SEQUENCE: 45

Met Ala Asn Ser Ser Lys Ile Leu Ile Ile Gly Gly Thr Gly Tyr Ile
1               5                   10                  15

Gly Arg His Ile Ser Lys Ala Ser Leu Ala Leu Gly His Pro Thr Phe
            20                  25                  30

Leu Leu Val Arg Glu Ser Ser Ala Ser Asn Pro Glu Lys Ala Lys Leu
        35                  40                  45

Leu Glu Ser Phe Lys Ala Ser Gly Ala Ile Ile Val Asn Gly Ser Leu
    50                  55                  60

Glu Asp Gln Ala Ser Leu Val Glu Ala Ile Lys Lys Val Asp Val Val
65                  70                  75                  80

Ile Ser Ala Val Lys Gly Pro Gln Leu Gly Asp Gln Leu Asn Ile Ile
                85                  90                  95

Lys Ala Ile Lys Glu Ile Gly Thr Ile Lys Arg Phe Leu Pro Ser Glu
            100                 105                 110

Phe Gly Asn Asp Val Asp Arg Thr His Ala Val Glu Pro Ala Lys Thr
        115                 120                 125

Met Phe Ala Asn Lys Ala Lys Ile Arg Arg Ala Ile Glu Ala Glu Gly
130                 135                 140

Ile Pro Tyr Thr Tyr Val Ser Ser Asn Cys Phe Ala Gly Leu Phe Leu
145                 150                 155                 160

Pro Ser Leu Gly Gln Pro Gly Leu Ser Ser Pro Arg Asp Lys Ala
                165                 170                 175

Val Ile Ser Gly Asp Gly Asn Ala Lys Val Val Phe Val Lys Glu Glu
            180                 185                 190

Asp Ile Gly Thr Phe Thr Ile Lys Ala Val Asp Asp Pro Arg Ala Leu
        195                 200                 205

Asn Lys Ile Leu Tyr Leu Arg Leu Pro Ala Asn Thr Tyr Ser Ile Asn
    210                 215                 220

Asp Leu Val Ala Leu Trp Glu Lys Lys Ile Gly Lys Thr Leu Glu Lys
225                 230                 235                 240

Thr Tyr Leu Ser Glu Glu Val Leu Lys Lys Ile Ala Glu Ser Pro
                245                 250                 255

Phe Pro Val Asn Ala Met Leu Ser Thr Gly His Ser Ile Phe Val Lys
            260                 265                 270

Gly Asp Gln Thr Asn Phe Glu Ile Gly Pro Asp Gly Val Glu Ala Ser
```

```
                  275                 280                 285
Gln Leu Tyr Pro Glu Val Lys Tyr Thr Thr Val Glu Glu Tyr Leu Gly
    290                 295                 300

Gln Tyr Val
305

<210> SEQ ID NO 46
<211> LENGTH: 307
<212> TYPE: PRT
<213> ORGANISM: Tsuga heterophylla

<400> SEQUENCE: 46

Met Ala Asn Ser Ser Lys Ile Leu Ile Ile Gly Gly Thr Gly Tyr Ile
1               5                   10                  15

Gly Arg His Ile Ser Lys Ala Ser Leu Ala Leu Gly His Pro Thr Phe
                20                  25                  30

Leu Leu Val Arg Glu Ser Ser Ala Ser Asn Pro Glu Lys Ala Lys Leu
            35                  40                  45

Leu Glu Ser Phe Lys Ala Ser Gly Ala Ile Ile Val Asn Gly Ser Leu
        50                  55                  60

Glu Asp Gln Val Ser Leu Val Glu Ala Ile Lys Lys Val Asp Val Val
65                  70                  75                  80

Ile Ser Ala Val Lys Gly Pro Gln Leu Gly Asp Gln Leu Asn Ile Ile
                85                  90                  95

Lys Ala Ile Lys Glu Ile Gly Thr Ile Lys Arg Phe Leu Pro Ser Glu
            100                 105                 110

Phe Gly Asn Asp Val Asp Arg Thr His Ala Val Glu Pro Ala Lys Thr
        115                 120                 125

Met Phe Ala Asn Lys Ala Lys Ile Arg Arg Ala Ile Glu Ala Glu Gly
    130                 135                 140

Ile Pro Tyr Thr Tyr Val Ser Ser Asn Cys Phe Ala Gly Leu Phe Leu
145                 150                 155                 160

Pro Ser Leu Gly Gln Pro Gly Leu Ser Ala Pro Pro Arg Asp Lys Ala
                165                 170                 175

Val Ile Ser Gly Asp Gly Asn Ala Lys Val Val Phe Val Lys Glu Glu
            180                 185                 190

Asp Ile Gly Thr Phe Thr Ile Lys Ala Val Asp Asp Pro Arg Ala Leu
        195                 200                 205

Asn Lys Ile Leu Tyr Leu Arg Leu Pro Ala Asn Thr Tyr Ser Ile Asn
    210                 215                 220

Asp Leu Val Ala Leu Trp Glu Lys Lys Ile Gly Lys Thr Leu Glu Lys
225                 230                 235                 240

Thr Tyr Leu Ser Glu Glu Val Leu Lys Lys Ile Ala Glu Ser Pro
                245                 250                 255

Phe Pro Val Asn Ala Met Leu Ser Thr Gly His Ser Ile Phe Val Lys
            260                 265                 270

Gly Asp Gln Thr Asn Phe Glu Ile Gly Pro Asp Gly Val Glu Ala Ser
        275                 280                 285

Gln Leu Tyr Pro Glu Val Lys Tyr Thr Thr Val Glu Glu Tyr Leu Gly
    290                 295                 300

Gln Tyr Val
305

<210> SEQ ID NO 47
<211> LENGTH: 308
```

```
<212> TYPE: PRT
<213> ORGANISM: Tsuga heterophylla

<400> SEQUENCE: 47

Met Gly Ser Lys Ser Arg Val Leu Ile Ile Gly Gly Thr Gly Tyr Ile
1               5                   10                  15

Gly Arg His Val Ala Lys Ala Ser Leu Asp Leu Gly His Pro Thr Phe
                20                  25                  30

Leu Leu Leu Arg Glu Ser Thr Pro Ser Ser Asn Ser Glu Lys Ala Gln
            35                  40                  45

Leu Val Glu Ser Phe Lys Ala Ser Gly Ala Lys Ile Leu His Gly Ser
    50                  55                  60

Ile Glu Asp His Ala Ser Leu Val Glu Ala Val Lys Gln Val Asp Val
65                  70                  75                  80

Val Ile Ser Thr Val Gly Ser Leu Gln Ile Glu Asn Gln Val Asn Ile
                85                  90                  95

Ile Lys Ala Ile Lys Glu Val Gly Thr Ile Lys Arg Phe Leu Pro Ser
                100                 105                 110

Glu Phe Gly Asn Asp Val Asp Lys Val His Ala Val Glu Pro Ala Lys
            115                 120                 125

Ser Val Phe Glu Val Lys Ala Lys Val Arg Arg Ala Ile Glu Ala Glu
    130                 135                 140

Gly Ile Pro Tyr Thr Tyr Ile Ser Ser Asn Cys Phe Ala Gly Tyr Phe
145                 150                 155                 160

Leu Pro Gly Leu Gly Gln Pro Gly Leu Thr Thr Pro Arg Asp Lys
                165                 170                 175

Ile Val Ile Leu Gly Asp Gly Asn Ala Lys Val Val Tyr Ala Lys Glu
                180                 185                 190

Glu Asp Ile Gly Thr Phe Thr Ile Lys Ala Val Asp Asp Leu Arg Thr
            195                 200                 205

Leu Asn Lys Thr Leu Tyr Leu Arg Leu Pro Ala Asn Thr Leu Ser Phe
    210                 215                 220

Asn Glu Val Val Gly Leu Trp Glu Lys Lys Ile Asp Lys Thr Leu Glu
225                 230                 235                 240

Lys Val Tyr Val Pro Glu Glu Gly Val Leu Lys Leu Ile Ala Asp Thr
                245                 250                 255

Pro Phe Pro Ala Asn Ile Gly Ile Ala Ile Gly His Ser Ile Phe Val
            260                 265                 270

Arg Gly Asp Gln Thr Asn Phe Glu Ile Gly Ala Asp Gly Val Glu Ala
        275                 280                 285

Ser Gln Leu Tyr Pro Glu Val Gln Tyr Thr Thr Val Asp Glu Tyr Leu
    290                 295                 300

Ser Lys Phe Val
305

<210> SEQ ID NO 48
<211> LENGTH: 308
<212> TYPE: PRT
<213> ORGANISM: Tsuga heterophylla

<400> SEQUENCE: 48

Met Gly Ser Lys Ser Lys Ile Leu Ile Ile Gly Ala Thr Gly Tyr Ile
1               5                   10                  15

Gly Arg Gln Val Ala Lys Ala Ser Leu Ala Leu Ser His Pro Thr Phe
                20                  25                  30
```

-continued

```
Leu Leu Val Arg Asp Ser Pro Ala Ser Ser Lys Pro Glu Lys Ala Gln
        35                  40                  45

Leu Leu Asp Ser Phe Lys Ala Ser Gly Ala Asn Ile Leu Lys Gly Ser
    50                  55                  60

Leu Glu Asp His Ala Ser Leu Val Glu Ala Val Lys Lys Val Asp Val
65                  70                  75                  80

Val Ile Ser Thr Val Gly Gly Glu Gln Ile Ala Asn Gln Phe Asn Ile
                85                  90                  95

Ile Lys Ala Ile Lys Glu Val Gly Thr Ile Lys Arg Phe Leu Pro Ser
            100                 105                 110

Glu Phe Gly Asn Asp Val Asp Asn Val His Ala Val Glu Pro Ala Lys
        115                 120                 125

Ser Val Phe Glu Leu Lys Ala Gln Val Arg Arg Ala Ile Glu Ala Glu
    130                 135                 140

Ser Ile Pro Tyr Thr Tyr Val Ser Ser Asn Cys Phe Ala Gly Tyr Phe
145                 150                 155                 160

Leu Pro Ser Phe Ala Gln Ala Gly Leu Thr Ser Pro Arg Asp Lys
                165                 170                 175

Val Val Ile Leu Gly Asp Gly Asn Ala Lys Ala Val Tyr Val Lys Glu
            180                 185                 190

Glu Asp Ile Gly Thr Phe Ala Ile Lys Ala Ala Asp Pro Arg Thr
        195                 200                 205

Leu Asn Lys Thr Leu Tyr Leu Arg Leu Pro Ala Asn Thr Leu Ser Phe
    210                 215                 220

Asn Glu Leu Val Ala Leu Trp Glu Lys Lys Ile Gly Lys Thr Leu Glu
225                 230                 235                 240

Lys Val Tyr Val Pro Glu Glu His Val Val Lys Leu Ile Ala Glu Thr
                245                 250                 255

Pro Phe Pro Ala Asn Ile Val Ile Ala Ile Gly His Ser Ile Phe Val
            260                 265                 270

Lys Gly Asp Gln Thr Asn Phe Asp Ile Gly Pro Asp Gly Val Glu Gly
        275                 280                 285

Ser Leu Leu Tyr Pro Asp Val Lys Tyr Thr Thr Val Asp Glu Tyr Leu
    290                 295                 300

Ser Ala Phe Val
305
```

<210> SEQ ID NO 49
<211> LENGTH: 308
<212> TYPE: PRT
<213> ORGANISM: Tsuga heterophylla

<400> SEQUENCE: 49

```
Met Gly Ser Lys Ser Lys Ile Leu Ile Ile Gly Ala Thr Gly Tyr Ile
1               5                   10                  15

Gly Arg Gln Val Ala Lys Ala Ser Leu Ala Leu Ser His Pro Thr Phe
                20                  25                  30

Leu Leu Val Arg Asp Ser Pro Ala Ser Ser Lys Pro Glu Lys Ala Gln
        35                  40                  45

Leu Leu Asp Ser Phe Lys Ala Ser Gly Ala Asn Ile Leu Lys Gly Ser
    50                  55                  60

Leu Glu Asp His Ala Ser Leu Val Glu Ala Val Lys Lys Val Asp Val
65                  70                  75                  80

Val Ile Ser Thr Val Gly Gly Glu Gln Ile Ala Asn Gln Phe Asn Ile
                85                  90                  95
```

```
Ile Lys Ala Ile Lys Glu Val Gly Thr Ile Lys Arg Phe Leu Pro Ser
                100                 105                 110

Glu Phe Gly Asn Asp Val Asp Asn Val His Ala Val Glu Pro Ala Lys
            115                 120                 125

Ser Val Phe Glu Leu Lys Ala Gln Val Arg Arg Ala Ile Glu Ala Glu
        130                 135                 140

Ser Ile Pro Tyr Thr Tyr Val Ser Ser Asn Cys Phe Ala Gly Tyr Phe
145                 150                 155                 160

Leu Pro Ser Phe Ala Gln Ala Gly Leu Thr Ser Pro Pro Arg Asp Lys
                165                 170                 175

Val Val Ile Leu Gly Asp Gly Asn Ala Lys Ala Val Tyr Val Lys Glu
            180                 185                 190

Glu Asp Ile Gly Thr Phe Ala Ile Lys Ala Ala Asp Asp Pro Arg Thr
        195                 200                 205

Leu Asn Lys Thr Leu Tyr Leu Arg Leu Pro Ala Asn Thr Leu Ser Phe
210                 215                 220

Asn Glu Leu Val Ala Leu Trp Glu Lys Lys Ile Gly Lys Thr Leu Glu
225                 230                 235                 240

Lys Val Tyr Val Pro Glu Glu His Val Val Lys Leu Ile Ala Glu Thr
                245                 250                 255

Pro Phe Pro Ala Asn Ile Val Ile Ala Ile Gly His Ser Ile Phe Val
            260                 265                 270

Lys Gly Asp Gln Thr Asn Phe Asp Ile Gly Pro Asp Gly Val Glu Gly
        275                 280                 285

Ser Leu Leu Tyr Pro Asp Val Lys Tyr Thr Thr Val Asp Glu Tyr Leu
    290                 295                 300

Ser Ala Phe Val
305

<210> SEQ ID NO 50
<211> LENGTH: 308
<212> TYPE: PRT
<213> ORGANISM: Tsuga heterophylla

<400> SEQUENCE: 50

Met Gly Ser Lys Ser Arg Val Leu Ile Ile Gly Gly Thr Gly Tyr Ile
1               5                   10                  15

Gly Arg His Val Ala Lys Ala Ser Leu Asp Leu Gly His Pro Thr Phe
            20                  25                  30

Leu Leu Leu Arg Glu Ser Thr Ala Ser Ser Asn Ser Glu Lys Ala Gln
        35                  40                  45

Leu Val Glu Ser Phe Lys Ala Ser Gly Ala Asn Ile Leu His Gly Ser
    50                  55                  60

Ile Glu Asp His Ala Ser Leu Val Glu Ala Val Lys Gln Val Asp Val
65                  70                  75                  80

Val Ile Ser Thr Val Gly Ser Leu Gln Ile Glu Asn Gln Val Asn Ile
                85                  90                  95

Ile Lys Ala Ile Lys Glu Val Gly Thr Ile Lys Arg Phe Leu Pro Ser
                100                 105                 110

Glu Phe Gly Asn Asp Val Asp Lys Val His Ala Val Glu Pro Ala Lys
            115                 120                 125

Ser Val Phe Glu Val Lys Ala Lys Val Arg Arg Ala Ile Glu Ala Glu
        130                 135                 140

Gly Ile Pro Tyr Thr Tyr Ile Ser Ser Asn Cys Phe Ala Gly Tyr Phe
```

```
            145                 150                 155                 160
Leu Pro Gly Leu Gly Gln Pro Gly Leu Thr Thr Pro Arg Asp Lys
                165                 170                 175

Ile Val Ile Leu Gly Asp Gly Asn Ala Lys Val Val Tyr Ala Lys Glu
            180                 185                 190

Glu Asp Ile Gly Thr Phe Thr Ile Lys Ala Val Asp Asp Leu Arg Thr
            195                 200                 205

Leu Asn Lys Thr Leu Tyr Leu Arg Leu Pro Ala Asn Thr Leu Ser Phe
            210                 215                 220

Asn Glu Val Val Gly Leu Trp Glu Lys Ile Asp Lys Thr Leu Glu
225                 230                 235                 240

Lys Val Tyr Val Pro Glu Gly Val Leu Lys Leu Ile Ala Asp Thr
                245                 250                 255

Pro Phe Pro Ala Asn Ile Gly Ile Ala Ile Gly His Ser Ile Phe Val
            260                 265                 270

Arg Gly Asp Gln Thr Asn Phe Glu Ile Gly Ala Asp Gly Val Glu Ala
            275                 280                 285

Ser Gln Leu Tyr Pro Glu Val Gln Tyr Thr Thr Val Asp Glu Tyr Leu
            290                 295                 300

Ser Lys Phe Val
305

<210> SEQ ID NO 51
<211> LENGTH: 308
<212> TYPE: PRT
<213> ORGANISM: Forsythia X intermedia

<400> SEQUENCE: 51

Met Ala Glu Lys Thr Lys Ile Leu Ile Ile Gly Gly Thr Gly Tyr Ile
1               5                   10                  15

Gly Lys Phe Val Ala Glu Ala Ser Ala Lys Ser Gly His Pro Thr Phe
            20                  25                  30

Ala Leu Phe Arg Glu Ser Thr Ile Ser Asp Pro Val Lys Gly Lys Ile
        35                  40                  45

Ile Glu Gly Phe Lys Asn Ser Gly Val Thr Ile Leu Thr Gly Asp Leu
50                  55                  60

Tyr Asp His Glu Ser Leu Val Lys Ala Ile Lys Gln Val Asp Val Val
65                  70                  75                  80

Ile Ser Thr Val Gly Ser Leu Gln Leu Ala Asp Gln Val Lys Ile Ile
                85                  90                  95

Ala Ala Ile Lys Glu Ala Gly Asn Val Lys Arg Phe Pro Ser Glu
            100                 105                 110

Phe Gly Thr Asp Val Asp Arg Cys His Ala Val Glu Pro Ala Lys Ser
        115                 120                 125

Ser Tyr Glu Ile Lys Ser Lys Ile Arg Arg Ala Val Glu Ala Glu Gly
    130                 135                 140

Ile Pro Phe Thr Phe Val Ser Ser Asn Tyr Phe Ala Gly Tyr Ser Leu
145                 150                 155                 160

Pro Thr Leu Val Gln Pro Gly Val Thr Ala Pro Arg Asp Lys Val
                165                 170                 175

Ile Ile Leu Gly Asp Gly Asn Ala Lys Ala Val Phe Asn Glu His
            180                 185                 190

Asp Ile Gly Thr Tyr Thr Ile Lys Ala Val Asp Asp Pro Arg Thr Leu
            195                 200                 205
```

-continued

Asn Lys Ile Leu Tyr Ile Lys Pro Pro Lys Asn Ile Tyr Ser Phe Asn
    210                 215                 220

Glu Leu Val Ala Leu Trp Glu Asn Lys Ile Gly Lys Thr Leu Glu Lys
225                 230                 235                 240

Ile Tyr Val Gln Glu Gln Leu Ile Lys Gln Ile Glu Glu Ser Pro
                245                 250                 255

Phe Pro Ile Asn Ile Val Leu Ala Ile Asn His Ser Val Phe Val Lys
            260                 265                 270

Gly Asp Leu Thr Asn Phe Lys Ile Glu Pro Ser Phe Gly Val Glu Ala
        275                 280                 285

Ser Glu Leu Tyr Pro Asp Val Lys Tyr Thr Thr Val Glu Glu Tyr Leu
    290                 295                 300

Ser His Phe Val
305

<210> SEQ ID NO 52
<211> LENGTH: 308
<212> TYPE: PRT
<213> ORGANISM: Forsythia X intermedia

<400> SEQUENCE: 52

Met Ala Glu Lys Thr Lys Ile Leu Ile Ile Gly Gly Thr Gly Tyr Ile
1               5                   10                  15

Gly Lys Phe Val Ala Glu Ala Ser Ala Lys Ser Gly His Pro Thr Phe
            20                  25                  30

Ala Leu Phe Arg Glu Ser Thr Ile Ser Asp Pro Val Lys Gly Lys Ile
        35                  40                  45

Ile Glu Gly Phe Lys Asn Ser Gly Val Thr Ile Leu Thr Gly Asp Leu
    50                  55                  60

Tyr Asp His Glu Ser Leu Val Lys Ala Ile Lys Gln Val Asp Val Val
65                  70                  75                  80

Ile Ser Thr Val Gly Ser Leu Gln Leu Ala Asp Gln Val Lys Ile Ile
                85                  90                  95

Gly Ala Ile Lys Glu Ala Gly Asn Val Lys Arg Phe Phe Pro Ser Glu
            100                 105                 110

Phe Gly Thr Asp Val Asp Arg Cys His Ala Val Glu Pro Ala Lys Ser
        115                 120                 125

Ser Phe Glu Ile Lys Ser Lys Ile Arg Arg Ala Val Glu Ala Glu Gly
    130                 135                 140

Ile Pro Phe Thr Phe Val Ser Ser Asn Tyr Phe Gly Gly Tyr Ser Leu
145                 150                 155                 160

Pro Thr Leu Val Gln Pro Gly Val Thr Ala Pro Pro Arg Asp Lys Val
                165                 170                 175

Ile Ile Leu Gly Asp Gly Asn Ala Lys Ala Val Phe Asn Glu Glu His
            180                 185                 190

Asp Ile Gly Thr Tyr Thr Ile Lys Ala Val Asp Asp Pro Arg Thr Leu
        195                 200                 205

Asn Lys Ile Leu Tyr Ile Lys Pro Pro Lys Asn Ile Leu His Ser Met
    210                 215                 220

Lys Leu Val Ala Leu Trp Glu Asn Lys Ile Gly Lys Thr Leu Glu Lys
225                 230                 235                 240

Ile Tyr Val Pro Glu Glu Gln Leu Ile Lys Gln Ile Glu Glu Ser Pro
                245                 250                 255

Phe Pro Ile Asn Ile Val Leu Ala Ile Asn His Ser Ala Phe Val Lys
            260                 265                 270

```
Gly Asp Leu Thr Asn Phe Lys Ile Glu Pro Ser Phe Gly Val Glu Ala
        275                 280                 285

Ser Glu Leu Tyr Pro Asp Val Lys Tyr Thr Thr Val Glu Glu Tyr Leu
        290                 295                 300

Asn His Phe Val
305

<210> SEQ ID NO 53
<211> LENGTH: 308
<212> TYPE: PRT
<213> ORGANISM: Populus balsamifera

<400> SEQUENCE: 53

Met Ala Asp Lys Ser Lys Ile Leu Ile Ile Gly Gly Thr Gly Tyr Ile
1               5                   10                  15

Gly Lys Phe Ile Val Glu Ala Ser Ala Lys Ala Gly His Pro Thr Phe
            20                  25                  30

Ala Leu Val Arg Glu Ser Thr Val Ser Asp Pro Val Lys Arg Glu Leu
        35                  40                  45

Val Glu Lys Phe Lys Asn Leu Gly Val Thr Leu Ile His Gly Asp Val
    50                  55                  60

Asp Gly His Asp Asn Leu Val Lys Ala Ile Lys Arg Val Asp Val Val
65                  70                  75                  80

Ile Ser Ala Ile Gly Ser Met Gln Ile Ala Asp Gln Thr Lys Ile Ile
                85                  90                  95

Ala Ala Ile Lys Glu Ala Gly Asn Val Lys Arg Phe Phe Pro Ser Glu
            100                 105                 110

Phe Gly Met Asp Val Asp His Val Asn Ala Val Glu Pro Ala Lys Thr
        115                 120                 125

Ala Phe Ala Met Lys Ala Gln Ile Arg Arg Ala Ile Glu Ala Ala Gly
    130                 135                 140

Ile Pro Tyr Thr Tyr Val Pro Ser Asn Phe Phe Ala Ala Tyr Tyr Leu
145                 150                 155                 160

Pro Thr Leu Ala Gln Phe Gly Leu Thr Ala Pro Pro Arg Asp Lys Ile
                165                 170                 175

Thr Ile Leu Gly Asp Gly Asn Ala Lys Leu Val Phe Asn Lys Glu Asp
            180                 185                 190

Asp Ile Gly Thr Tyr Thr Ile Lys Ala Val Asp Asp Ala Arg Thr Leu
        195                 200                 205

Asn Lys Thr Val Leu Ile Lys Pro Pro Lys Asn Thr Tyr Ser Phe Asn
    210                 215                 220

Glu Leu Ile Asp Leu Trp Glu Lys Lys Ile Gly Lys Thr Leu Glu Lys
225                 230                 235                 240

Thr Phe Val Pro Glu Glu Lys Leu Leu Lys Asp Ile Gln Glu Ser Pro
                245                 250                 255

Ile Pro Ile Asn Ile Val Leu Ser Ile Asn His Ser Ala Leu Val Asn
            260                 265                 270

Gly Asp Met Thr Asn Phe Glu Ile Asp Pro Ser Trp Gly Leu Glu Ala
        275                 280                 285

Ser Glu Leu Tyr Pro Asp Val Lys Tyr Thr Thr Val Glu Glu Tyr Leu
    290                 295                 300

Asp Gln Phe Val
305
```

<210> SEQ ID NO 54
<211> LENGTH: 309
<212> TYPE: PRT
<213> ORGANISM: Zea mays

<400> SEQUENCE: 54

Met Ala Ser Glu Lys Ser Lys Ile Leu Val Gly Thr Gly Tyr
1               5                   10                  15

Leu Gly Arg His Val Val Ala Ala Ser Ala Arg Leu Gly His Pro Thr
            20                  25                  30

Ser Ala Leu Val Arg Asp Thr Ala Pro Ser Asp Pro Ala Lys Ala Ala
            35                  40                  45

Leu Leu Lys Ser Phe Gln Asp Ala Gly Val Thr Leu Leu Lys Gly Asp
        50                  55                  60

Leu Tyr Asp Gln Ala Ser Leu Val Ser Ala Val Lys Gly Ala Asp Val
65                  70                  75                  80

Val Ile Ser Val Leu Gly Ser Met Gln Ile Ala Asp Gln Ser Arg Leu
                85                  90                  95

Val Asp Ala Ile Lys Glu Ala Gly Asn Val Lys Arg Phe Phe Pro Ser
            100                 105                 110

Glu Phe Gly Lys Asp Val Asp Arg Thr Gly Ile Val Glu Pro Ala Lys
        115                 120                 125

Ser Ile Leu Gly Ala Lys Val Gly Ile Arg Arg Ala Thr Glu Ala Ala
    130                 135                 140

Gly Ile Pro Tyr Thr Tyr Ala Val Ala Gly Phe Phe Ala Gly Phe Gly
145                 150                 155                 160

Leu Pro Lys Val Gly Gln Val Lys Ala Pro Gly Pro Pro Ala Asp Lys
                165                 170                 175

Ala Val Val Leu Gly Asp Gly Asp Thr Lys Ala Val Phe Val Glu Glu
            180                 185                 190

Gly Asp Ile Ala Thr Tyr Thr Val Leu Ala Ala Asp Pro Arg Ala
        195                 200                 205

Glu Asn Lys Val Leu Tyr Ile Lys Pro Pro Ala Asn Thr Leu Ser His
    210                 215                 220

Asn Glu Leu Leu Ser Leu Trp Glu Lys Lys Thr Gly Lys Thr Phe Arg
225                 230                 235                 240

Arg Glu Tyr Val Pro Glu Glu Ala Val Leu Lys Gln Ile Gln Glu Ser
                245                 250                 255

Pro Ile Pro Leu Asn Ile Ile Leu Ala Ile Gly His Ala Ala Phe Val
            260                 265                 270

Arg Gly Glu Gln Thr Gly Phe Glu Ile Asp Pro Ala Lys Gly Val Asp
        275                 280                 285

Ala Ser Glu Leu Tyr Pro Asp Val Lys Tyr Thr Thr Val Asp Glu Tyr
    290                 295                 300

Leu Asn Arg Phe Leu
305

<210> SEQ ID NO 55
<211> LENGTH: 308
<212> TYPE: PRT
<213> ORGANISM: Solanum tuberosum

<400> SEQUENCE: 55

Met Ala Gly Lys Ser Lys Ile Leu Phe Ile Gly Gly Thr Gly Tyr Ile
1               5                   10                  15

Gly Lys Phe Ile Val Glu Ala Ser Ala Lys Ala Gly His Asp Thr Phe

-continued

```
                20                  25                  30
Val Leu Val Arg Glu Ser Thr Leu Ser Asn Pro Thr Lys Thr Lys Leu
            35                  40                  45
Ile Asp Thr Phe Lys Ser Phe Gly Val Thr Phe Val His Gly Asp Leu
 50                  55                  60
Tyr Asp His Glu Ser Leu Val Lys Ala Ile Lys Gln Val Asp Val Val
 65                  70                  75                  80
Ile Ser Thr Val Gly His Ala Leu Leu Ala Asp Gln Val Lys Leu Ile
                85                  90                  95
Ala Ala Ile Lys Glu Ala Gly Asn Val Lys Arg Phe Phe Pro Ser Glu
                100                 105                 110
Phe Gly Asn Asp Val Asp Arg Val His Ala Val Glu Pro Ala Lys Ala
                115                 120                 125
Ala Phe Asn Thr Lys Ala Gln Ile Arg Arg Val Val Glu Ala Glu Gly
                130                 135                 140
Ile Pro Phe Thr Tyr Val Ala Thr Phe Phe Phe Ala Gly Tyr Ser Leu
145                 150                 155                 160
Pro Asn Leu Ala Gln Pro Gly Ala Ala Gly Pro Pro Asn Asp Lys Val
                165                 170                 175
Val Ile Leu Gly His Gly Asn Thr Lys Ala Val Phe Asn Lys Glu Glu
                180                 185                 190
Asp Ile Gly Thr Tyr Thr Ile Asn Ala Val Asp Asp Pro Lys Thr Leu
                195                 200                 205
Asn Lys Ile Leu Tyr Ile Lys Pro Pro His Asn Ile Ile Thr Leu Asn
                210                 215                 220
Glu Leu Val Ser Leu Trp Glu Lys Lys Thr Gly Lys Asn Leu Glu Arg
225                 230                 235                 240
Leu Tyr Val Pro Glu Glu Gln Val Leu Lys Asn Ile Gln Glu Ala Ser
                245                 250                 255
Val Pro Met Asn Val Gly Leu Ser Ile Tyr His Thr Ala Phe Val Lys
                260                 265                 270
Gly Asp His Thr Asn Phe Glu Ile Glu Pro Ser Phe Gly Val Glu Ala
                275                 280                 285
Ser Glu Val Tyr Pro Asp Val Lys Tyr Thr Pro Ile Asp Glu Ile Leu
                290                 295                 300
Asn Gln Tyr Val
305

<210> SEQ ID NO 56
<211> LENGTH: 320
<212> TYPE: PRT
<213> ORGANISM: Citrus paradisi

<400> SEQUENCE: 56

Met Glu Gly Glu Asn Thr Lys Pro Lys Ile Leu Ile Phe Gly Gly Thr
 1                5                  10                  15
Gly Tyr Phe Gly Lys Tyr Met Val Lys Ala Ser Val Ser Ser Gly His
                20                  25                  30
Lys Thr Phe Val Tyr Ala Arg Pro Val Thr Gln Asn Ser Arg Pro Ser
            35                  40                  45
Lys Leu Glu Ile His Lys Glu Phe Gln Gly Ile Gly Val Thr Ile Ile
            50                  55                  60
Glu Gly Glu Leu Asp Glu His Glu Lys Ile Val Ser Ile Leu Lys Glu
 65                  70                  75                  80
```

-continued

```
Val Asp Val Val Ile Ser Thr Val Thr Tyr Pro Gln Cys Lys Asp Gln
             85              90              95

Leu Lys Ile Val His Ala Ile Lys Val Ala Gly Asn Ile Lys Arg Phe
            100             105             110

Leu Pro Ser Asp Phe Glu Cys Glu Glu Asp Arg Val Arg Pro Leu Pro
            115             120             125

Pro Phe Glu Ala Cys Leu Glu Lys Lys Arg Ile Val Arg Arg Ala Ile
        130             135             140

Glu Ala Ala Gln Ile Pro Tyr Thr Phe Val Ser Ala Asn Leu Cys Gly
145                 150             155                 160

Ala Tyr Phe Val Asn Val Leu Leu Arg Pro Ser Glu Ser His Asp Asp
                165             170             175

Val Val Val Tyr Gly Ser Gly Glu Ala Lys Ala Val Phe Asn Tyr Glu
            180             185             190

Glu Asp Ile Ala Lys Cys Thr Ile Lys Val Ile Asn Asp Pro Arg Thr
            195             200             205

Cys Asn Arg Ile Val Ile Tyr Arg Pro Gln Ala Ser Ile Ile Ser Gln
    210             215             220

Lys Glu Leu Ile Ser Leu Trp Glu Gln Lys Thr Gly Trp Ser Phe Lys
225             230             235                 240

Arg Val His Val Ser Glu Glu Glu Leu Val Lys Leu Ser Glu Thr Leu
                245             250             255

Pro Pro Pro Glu Asp Ile Pro Ile Ser Ile Ile His Ser Ala Leu Ala
            260             265             270

Lys Gly Asp Leu Met Asn Phe Glu Leu Gly Glu Asp Ile Glu Ala
        275             280             285

Ser Met Leu Tyr Pro Asp Phe Lys Phe Thr Thr Ile Asp Gln Leu Leu
    290             295             300

Asp Ile Phe Leu Ile Asp Pro Pro Lys Pro Ala Arg Thr Ala Phe Glu
305             310             315             320
```

GENE AND USES THEREFOR TO MODIFY PASTURE QUALITIES OF CROPS

This application is a §371 national stage of PCT International Application No. PCT/AU02/00179, filed Feb. 21, 2002, designating the United States of America, which claims priority of Australian Application No. PR3241/01, filed Feb. 21, 2001, the entire contents of which is hereby incorporated by reference into this application.

FIELD OF THE INVENTION

The present invention relates generally to isolated leucoanthocyanidin reductase polypeptides of the Reductase-Epimerase-Dehydrogenase (RED) protein family, and nucleic acid molecules encoding same and their use in regulating the biosynthesis and accumulation of proanthocyanidins in plants. The present invention is further directed to isolated nucleic acid molecules of plants which encode leucoanthocyanidin reductases of the RED protein family. The isolated polypeptides and nucleic acid molecules of the present invention are useful for modifying the pasture quality of legumes, and, in particular, for producing bloat-safe forage crops, or crops having enhanced nutritional value, enhanced disease resistance or pest resistance, or enhanced malting qualities.

GENERAL

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

Throughout this specification, unless the context requires otherwise the word "comprise", and variations such as "comprises" and "comprising", will be understood to imply the inclusion of a stated integer or step or group of integers or steps but not the exclusion of any other integer or step or group of integers or steps. The present invention is not to be limited in scope by the specific embodiments described herein, which are intended for the purposes of exemplification only. Functionally-equivalent products, compositions and methods are clearly within the scope of the invention, as described herein.

Bibliographic details of the publications referred to by author in this specification are collected at the end of the description. Reference herein to prior art, including any one or more prior art documents, is not to be taken as an acknowledgment, or suggestion, that said prior art is common general knowledge in Australia or forms a part of the common general knowledge in Australia.

As used herein, the term "derived from" shall be taken to indicate that a particular integer or group of integers has originated from the species specified, but has not necessarily been obtained directly from the specified source.

This specification contains nucleotide sequence information prepared using the program Patentin Version 3.0, presented herein after the claims. Each nucleotide sequence is identified in the sequence listing by the numeric indicator <210> followed by the sequence identifier (e.g. <210>1, <210>2, etc). The length, type of sequence (DNA, protein (PRT), etc) and source organism for each nucleotide sequence are indicated by information provided in the numeric indicator fields <211>, <212> and <213>, respectively. Nucleotide sequences referred to in the specification are defined by the term "SEQ ID NO:", followed by the sequence identifier (e.g. SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymidine, Y represents a pyrimidine residue, R represents a purine residue, M represents Adenine or Cytosine, K represents Guanine or Thymidine, S represents Guanine or Cytosine, W represents Adenine or Thymidine, H represents a nucleotide other than Guanine, B represents a nucleotide other than Adenine, V represents a nucleotide other than Thymidine, D represents a nucleotide other than Cytosine and N represents any nucleotide residue.

BACKGROUND TO THE INVENTION

In work leading up to the present invention, the inventors sought to develop fodder and forage legumes which improve the productivity of livestock animals, in particular ruminant livestock animals that are grazed thereon. By protecting protein from microbial degradation in the rumen, the inventors considered that the availability of protein from soft legume leaf cells to the livestock animal could be increased, thereby enhancing live-weight gains, wool growth and milk production. Increased post-rumen protein supply, was thus expected by the inventors to significantly enhance the efficiency of pasture use.

Pasture bloat is a serious risk for cattle grazing on forage legumes. Bloat often results in loss of livestock, and productivity may also be reduced considerably by the stress of sub-lethal bloat. The fear of bloat and the required vigilance also has a negative impact on dairy farmers lifestyle.

Bloat is a major constraint on dairy farm profitability. The cost of bloat also impacts significantly on beef production.

Because of high nutritive value, white clover and lucerne are used extensively in the dairy industry. It is estimated that white clover is potentially worth at least AUD412 million to the Australian dairy industry. Bloat was identified as a major constraint on the realization of this economic potential, costing the Australian agricultural sector alone AUD184 million per annum. There is a clear need in the dairy industry for the production of bloat-safe lucerne and white clover crops.

DESCRIPTION OF THE PRIOR ART

It is known that bloat is caused by the production of a highly stable protein foam in the rumen during the initial rapid fermentation of fresh legume forage. There is negative correlation between the level of condensed tannins in the foliage of legumes and the ability of particular legumes to induce bloating in livestock animals such as cattle, which have been grazed thereon (Jones and Lyttleton, 1971; Li et al., 1996; Table 1). Furthermore, Tanner et al. (1995) have demonstrated that the presence of foliar proanthocyanidin significantly reduces the compressive strength of protein foams formed from red clover leaf protein.

TABLE 1

Correlation between the absence of condensed tannins and bloating

| | Condensed tannins in foliage | |
|---|---|---|
| | Absent | Present |
| Bloat-safe | Dolichos axillaris | Onobrychis viciifolia |
| | Phaseolus atropurpureus | Onithopus pinnatus |
| | Lotononis bainesii | Ornithipus compressus |
| | Glycine javanica | Coronilla varia |
| | Stylosanthes humilis | Lotus corniculatus |
| | Astragalus cicer | Lotus pedunculatus |
| | Centroema pubescens | Lotus purshianus |
| | | Lotus angustissimus |
| | | Lotus tenuis |
| | | Lespediza stipulacea |
| | | Desmodium intortum |
| | | Desmodium uncinatum |
| | | Leucaena leucocephala |
| | | Macrotyloma axillare |
| | | Stylosanthes gracilis |
| | | Trifolium dubium |
| Bloating | Trifolium hybridum | |
| | Trifolium repens | |
| | Trofolium pratense | |
| | Dolichos lablab | |
| | Medicago sativa | |

Furthermore, there is also correlation between the presence of condensed tannins in forage crops such as *Lotus corniculatus*, *Onobrychis viciifolia* and *Trifolium arvense*, and the levels of post-rumen protein availability and protein loss in rumenants.

In general, there is a higher efficiency of protein utilization by rumenous livestock animals fed on forage crops which contain condensed tannins than by animals fed on crops with low tannin content (Terrill et al, 1992b; McNabb et al, 1993; Wang et al, 1994; Lee et al, 1995; Niezen et al, 1995). Without tannins, the rapid release of soluble protein from the soft legume leaf cells results in more protein than can be incorporated into rumen microbial protein. The excess soluble protein is broken down to ammonia which is absorbed and excreted as urea. This represents a major wastage of dietary protein; approximately 30–40% of dietary protein may be lost due to rumen degradation (Barry and Reid, 1985).

Condensed tannins are polymeric phenolics present in many plants including ferns, sorghum, grain legumes, grapes and other fruit, fodder and forage legumes. Condensed tannins, such as proanthocyanidins and oligomers or polymers thereof, comprise flavan-3-ol monomeric units, linked, for example, by C4:C8 or C4:C6 bonds.

Although proanthocyanidins accumulate in the vacuoles of higher plant cells, much of their biosynthesis, from malonyl CoA to catechin, occurs in the cytosol. The cytosolic enzyme leucoanthocyanidin reductase catalyses the first committed step in the synthesis of proanthocyanidin from leucoanthocyanidin.

International Patent Application No. PCT/AU97/00529 published in February, 1998 describes the purification of leucoanthocyanidin reductase enzyme of the aldo-keto reductase family of proteins from *Onobrychis viciifolia*, and the cloning of a gene encoding said enzyme. The aldo-keto reductase superfamily of enzymes is a well-defined class of NAD(P)-utilizing reductases, including soybean and alfalfa chalcone reductases (CHR), plant sorbitol-6-phosphate dehydrogenases (sorb6PD), barley and mammalian aldose reductases (ALDR), bovine prostaglandin F synthase, bacterial morphine dehydrogenase (morph deHase) and human hydroxysteroid dehydrogenase (3αHyroxSTERD). The aldo-keto reductases, including the leucoanthocyanidin reductase described in International Patent Application No. PCT/AU97/00529, are characterized by an amino acid sequence comprising the following peptide motifs:

(i) the HFDCAADYK motif (SEQ ID NO: 1);
(ii) the KENFQVFDFELSK motif (SEQ ID NO: 2); and
(iii) the GDLILMD (SEQ ID NO: 3) motif.

Additionally, aldo-keto reductase enzymes, including the putative leucoanthocyanidin reductase described in International Patent Application No. PCT/AU97/00529, generally have a subunit molecular weight of about 35 kDa, and an isoelectric point of about 6.09±0.64.

Devic et al. (1999) disclose the isolation and cloning of a gene that is presumably involved in the proanthocyanidin metabolic pathway between anthocyanins and proanthocyanidins in the seed coat of *Arabidopsis thaliana*. This gene, designated BANYULS (BAN) encodes a protein having limited similarity at the amino acid sequence level to dihydroflavanol reductase (DFR), and other enzymes of the phenylpropanoid biosynthesis pathway.

Jende-Strid (1978; 1984) disclose a sodium azide-induced mutant of barley (*Hordeum vulgare*), designated ant19, that synthesizes wild-type levels of anthocyanins in its vegetative tissues, however lacks catechins or proanthocyanidin in the testa, and postulate that the ant19 gene may encode LAR. However, the ant19 gene has not been isolated. Nor has the coding capacity of the barley ant19 gene been confirmed by functional tests.

SUMMARY OF THE INVENTION

In work leading up to the present invention, the inventors sought to isolate nucleotide sequences encoding leucoanthocyanidin reductase (LAR) from an important fodder crop, *Desmodium uncinatum*. They purified an LAR enzyme from the leaves of *D. uncinatum*, and determined the amino acid sequences of fragments of the isolated protein.

Surprisingly, the inventors found that the isolated LAR of *D. uncinatum* is not an aldo-keto reductase protein, as expected from the disclosure contained in International Patent Application No. PCT/AU97/00529. In fact, the *D. uncinatum* LAR enzyme belongs to the Reductase-Epimerase-Dehydrogenase (RED) protein superfamily.

The isolated *D. uncinatum* protein preparation exemplified herein has been purified approximately 48,500-fold, and is substantially free of conspecific proteins as determined by SDS/PAGE or two-dimensional gel electrophoresis or N-terminal amino acid sequence analysis of the isolated protein. By "conspecific protein" means a protein of the same plant species from which the LAR protein was originally derived. By "sustantially free of conspecific proteins" means that the LAR preparation is sufficiently free of other plant proteins to be suitable for a specific application of the protein product, such as, for example, enzyme assay, antibody preparation, amino acid sequence or composition analysis, peptide fragment production, or protein crystal structure determination. As will be known to those skilled in the art, a protein preparation that is substantially free of conspecific proteins for the purposes of enzyme assay may not be suitable for amino acid sequence determination, because said conspecific proteins, whilst not adversely affecting enzyme activity may confound sequence analysis of the LAR protein. Notwithstanding that this is the case, the skilled artisan will readily be able to determine the tolerance of an LAR enzyme preparation to any conspecific protein.

Accordingly, one aspect of the present invention provides an isolated LAR polypeptide of the RED protein superfamily, a truncated form of said LAR polypeptide, or an internal fragment or N-terminal fragment or C-terminal fragment of said LAR polypeptide, wherein said fragment comprises at least about 10 contiguous amino acids in length derived from said LAR polypeptide.

Those skilled in the art will be aware that a family of proteins means a group of functionally and/or structurally related proteins. Structurally-related proteins generally contain one or more conserved sequences (hereinafter "signature" or "signature motif"). As will be known to those skilled in the art, a signature is generally determined by conducting a multiple alignment of amino acid sequences, preferably using amino acid sequences having similar, or at least related, catalytic functions or substrate specificities. Such alignments can be readily conducted using any art-recognized techniques for comparison of amino acid sequences, such as, for example, the CLUSTAL W algorithm of Thompson et al (1994) for multiple alignments, which algorithm maximizes the number of identical/similar amino acids and minimizes the number and/or length of sequence gaps.

A "superfamily" generally refers to a large group of functionally divergent protein families that share particular signature motifs.

An analysis of protein families and superfamilies may be conducted using the software of the Dept. of Genetics at Washington University School of Medicine, 4566 Scott Ave, St. Louis, Mo. 63110, USA, and, more particularly, using the Pfam database of multiple alignments of protein domains or conserved protein regions (Bateman et al., 2000). The alignments in the Pfam database represent evolutionarily-conserved signatures which have implications for protein function, wherein Profile Hidden Markov Models (i.e. profile HMMs) built from the Pfam alignments can be used to assign a protein to an existing protein family, even if the overall sequence identity is weak.

It is known in the art that the power of profile HMM methods can be further enhanced through iteration of the search procedure. Accordingly, after a profile is run against a particular database, new similar sequences can be detected, generating a new multiple alignment which includes these latter sequences, from which a new profile can be abstracted. Iteration can be repeated as often as desirable, or until convergence, when no new statistically significant sequences are detected. Accordingly, the PSI BLAST algorithm (Altschul, et al., 1997), which iterates the search procedure, is particularly preferred for identifying proteins of the RED superfamily.

The Reductase-Epimerase-Dehydrogenase superfamily includes the following proteins: 3-beta-hydroxysteroid dehydrogenase, dihydroflavanol reductase, UDP-Galactose-4-epimerase, cinnamoyl-CoA reductase, Isoflavone reductase; 2'-hydroxyisoflavone reductase; NADPH oxidoreductase; phenylcoumaran benzylic ether reductase; and pinoresinol-lariciresinol reductase. The RED enzyme family is highly diverse, both in amino acid sequence and the types of chemical reactions that it catalyses. Recoghisable members of the family can have less than 20% amino acid identity but can be recognised and further characterized by the presence of one or more characteristic signature motifs, as detennined using the PSI-BLAST algorithm set at an E-value threshold of 0.001 for inclusion in the iteration process (Altschul et al., 1997). The catalytic versatility of the RED domain is probably why the family is very common among enzymes of plant secondary product metabolism. For example dihydroflavanol reductase, the enzyme preceding LAR in the proanthocyanidin pathway is also a member of the RED family but has less than 20% amino acid identity to *Desmodium* LAR. Among the more closely related RED family members, namely the Isoflavone reductase group including isoflavone reductase; 2'-hydroxyisoflavone reductase; NADPH oxidoreductase; phenylcoumaran benzylic ether reductase; and pinoresinol-lariciresinol reductase, the amino acid sequence identity can be very low. Chickpea isoflavone reductase (pir|||S17830) is only 38% identical to *Arabidopsis* isoflavone reductase (pir|||T05274). In the case of pinoresinol-lariciresinol reductase, isoforms within the same species, namely *Thuja plicata* are only 69% identical and 57% between *Thuja* and *Forsythia*.

Preferably, a Reductase-Epimerase-Dehydrogenase (RED) protein has an amino acid sequence that comprises one, more preferably two, even more preferably three, and still more preferably all, of the following signature motifs:

(i) Leu-$Xaa_1$-$Xaa_2$-Gly-$Xaa_3$-Thr-Gly-$Xaa_4$-$Xaa_1$-Gly-$Xaa_5$, wherein $Xaa_1$ is selected from the group consisting of: Met, Ile, Val, Leu, Phe, and Tyr; $Xaa_2$ is selected from the group consisting of: Met, Ile, Val, and Leu; $Xaa_3$ is selected from the group consisting of: Ala, Gly, and Pro; $Xaa_4$ is any amino acid; and $Xaa_5$ is selected from the group consisting of: a charged amino acid residue, Asn, and Gln (SEQ ID NO: 4);

(ii) Lys-$Xaa_1$-$Xaa_2$-$Xaa_2$-Pro-Ser-Glu-Phe-$Xaa_3$-Xaa4-Asp, wherein $Xaa_1$ is Arg or Lys; $Xaa_2$ is selected from the group consisting of: Phe, Tyr, Met, Val, Ile, and Leu; $Xaa_3$ is selected from the group consisting of: Ala, Gly, Arg, and Lys; and $Xaa_4$ is any amino acid residue (SEQ ID NO: 5);

(iii) $Xaa_1$-Asp-$Xaa_2$-$Xaa_3$-$Xaa_4$-Leu-Asn-Lys, wherein $Xaa_1$ is Asp or Asn; $Xaa_2$ is any amino acid residue; $Xaa_3$ is selected from the group consisting of: Arg, Lys, Asn, and Gln; and $Xaa_4$ is selected from the group consisting of: Ala, Gly, Ser, and Thr (SEQ ID NO: 6); and (iv) $Xaa_1$-Tyr-Pro-$Xaa_2$-$Xaa_2$-$Xaa_3$-$Xaa_4$, wherein $Xaa_1$ is selected from the group consisting of: Ala, Gly, Val, Ile, Met, and Leu; $Xaa_2$ is a charged amino acid residue: $Xaa_3$ is any amino acid residue; and $Xaa_4$ is Phe or Tyr (SEQ ID NO: 7).

As a member of the RED protein superfamily, the leucoanthocyanidin reductase polypeptide will be understood to include at least one, preferably at least two, more preferably at least three, and even more preferably all four of the signature motifs supra.

As used herein, the term "leucoanthocyanidin reductase" or "LAR" shall be taken to refer to a polypeptide or enzyme which is capable of carrying out the reduction of C-4 of a flavan-3,4-diol substrate or epimer thereof, such as, for example, a compound listed in Table 2. The reaction utilizes a cofactor selected from the group consisting of: NAD, NADH, NADP, and NADPH. Known products of the reaction catalyzed by LAR are compounds selected from the group consisting of: catechin, gallocatechin, afzelechin, and epimers thereof (e.g. epi-catechin, epi-gallocatechin, and epi-afzelechin). As will be known to those skilled in the art, epi-catechin, epi-gallocatechin, and epi-afzelechin are abundant in the condensed tannins present in the leaves of legumes.

The term "LAR" shall also be taken to include the isolated LAR enzyme, a native or denatured LAR polypeptide, or a recombinant LAR polypeptide. For the present purposes, the term "LAR" shall also be taken to include any peptide fragments or parts derived from a polypeptide, polypeptide aggregate or fusion polypeptide or homologue, analogue or derivative thereof, which, although they have no enzyme catalytic activity are at least useful for the performance of any embodiment described herein.

Accordingly, the term "LAR polypeptide of the Reductase-Epimerase-Dehydrogenase (RED) protein family" means LAR as defined herein above having at least about 35% amino acid sequence identity to a protein selected from the group consisting of: isoflavone reductase; 2'-hydroxyisoflavone reductase; NADPH oxidoreductase; phenylcoumaran benzylic ether reductase; and pinoresinol-lariciresinol reductase; and preferably, having one or more of RED signature motifs.

The present inventors provide the amino acid sequences set forth in SEQ ID NOs: 16–23, 27, and 29–31, as exemplary LAR polypeptides of the RED protein superfamily. For the purposes of nomenclature, the amino acid sequences set forth in SEQ ID NOs: 16–21 represent internal fragments of the *D. uncinatum* LAR polypeptide, derived by trypsinization of the isolated LAR enzyme. The amino acid sequences set forth in SEQ ID NOs: 22 and 23 represent the N-terminal sequence of the isolated *D. uncinatum* LAR enzyme. The amino acid sequence set forth in SEQ ID NO: 27 represents the deduced amino acid sequence encoded by an amplified fragment of the isolated mature *D. uncinatum* LAR gene. The amino acid sequence set forth in SEQ ID NO: 29 represents the deduced amino acid sequence encoded by a full-length *D. uncinatum* LAR cDNA. An exemplary truncated form of the LAR polypeptide is represented by amino acids 1 to 317 of SEQ ID NO:29. The amino acid sequences set forth in SEQ ID NOs: 30 and 31 represent synthetic peptides used to generate antibodies against the LAR polypeptides of the RED superfamily.

Whilst the exemplified method described herein for isolating the LAR polypeptide from *D. uncinatum* is an optimized protocol to provide LAR in a form suitable for amino acid sequence determination, those skilled in the art will be aware that a simplified protocol may be developed based upon this optimization by the present inventors. For many applications that merely require a partially purified enzyme preparation, such as, for example, the performance of enzyme assays in vitro, it is generally sufficient to employ only those processes that provide the greatest step purification. Accordingly, a second aspect of the present invention provides a method of isolating an LAR polypeptide of the RED protein superfamily from, a cell, said method comprising at least three purification steps each of which employs a matrix having a different dye ligand attached thereto, and a purification step that employs an ion exchange matrix.

The present inventors have further produced antibodies directed against synthetic peptides encoded by portions of the full length LAR cDNA. Accordingly, a further aspect of the present invention provides an antibody molecule prepared by a process comprising immunizing an animal with an immunologically-effective amount of an isolated LAR polypeptide of the RED protein superfamily or a truncated form thereof or a fragment comprising at least about 10 contiguous amino acids in length of said LAR polypeptide, and isolating a monoclonal or polyclonal antibody from said animal. This invention clearly extends to any monoclonal or polyclonal antibody that binds to an LAR polypeptide of the RED protein superfamily or to a truncated form thereof or to a fragment comprising at least about 10 contiguous amino acids in length of said LAR polypeptide.

The inventors have further produced degenerate oligonucleotide primers capable of hybridizing to mRNA encoding *D. uncinatum* LAR peptide fragments, and amplified nucleotide sequences encoding LAR in a polymerase chain reaction. The amplified probe was used to isolate full-length cDNAs and genes encoding *D. uncinatum* LAR. The nucleotide sequence of the *D. uncinatum* LAR-encoding cDNA is set forth herein as SEQ ID NO: 28. Gene fragments, exemplified herein as oligonucleotide primers of the LAR gene, are set forth herein as SEQ ID NOs: 24–26. More particularly, the nucleotide sequences set forth as SEQ ID NOs: 24 and 25 relate to degenerate oligonucleotide primers derived from the amino acid sequences of internal peptide fragments produced by trypsinization of isolated LAR. Additional gene fragments are exemplified herein as a fragment of the *D. uncinatum* LAR gene produced by PCR using the degenerate oligonucleotide primers supra, the nucleotide sequence of which is set forth in SEQ ID NO: 26.

Accordingly, a further aspect of the present invention provides an isolated nucleic acid molecule comprising a nucleotide sequence that encodes a member selected from the group consisting of: (i) an LAR polypeptide of the RED protein superfamily; (ii) a truncated form of said LAR polypeptide; (iii) a fragment comprising at least about 10 contiguous amino acids of said LAR polypeptide; and (iv) a nucleotide sequence that is complementary to (i), (ii) or (iii).

In an alternative embodiment, there is provided an isolated nucleic acid molecule comprising a nucleotide sequence that encodes an LAR polypeptide of the RED protein superfamily or a fragment thereof, wherein said nucleic acid molecule is isolated by a process comprising:

(i) hybridizing a probe or primer comprising at least about 20 contiguous nucleotides of SEQ ID NO: 28 or a degenerate or complementary nucleotide sequence thereto, to nucleic acid of plants;
(ii) detecting said hybridization;
(iii) isolating the hybridized nucleic acid; and
(iv) determining the amino acid sequence encoded by the hybridized nucleic acid or the function of said amino acid sequence so as to determine that the hybridized nucleic acid encodes said LAR polypeptide.

This invention clearly extends to any gene constructs that comprise the LAR gene of the present invention, such as, for example, any expression gene constructs produced for expressing said LAR gene in a bacterial, insect, yeast, plant, fungal, or animal cell. Accordingly, a further aspect of the present invention is directed to a gene construct comprising an isolated nucleic acid that encodes an LAR polypeptide of the RED protein superfamily or a fragment thereof or complementary nucleotide sequence thereto A further aspect of the invention contemplates an isolated cell comprising a heterologous LAR gene, preferably wherein said LAR gene is present in said cell in an expressible format.

A further aspect of the invention contemplates a transformed plant comprising a non-endogenous LAR gene or fragment thereof introduced into its genome, or a nucleotide sequence that is complementary to said LAR gene or said fragment, in an expressible format. Preferably, the transformed plant of the invention further expresses a non-endogenous LAR polypeptide of the RED protein superfamily. This aspect of the invention clearly extends to any plant parts, or progeny plants, that are derived from the primary transformed plant.

A still further aspect of the invention contemplates a method of enhancing the expression of an LAR polypeptide of the RED protein superfamily in a plant comprising introducing to the genome of said plant a non-endogenous LAR gene or a fragment of said LAR gene or a nucleotide sequence that is complementary to said non-endogenous LAR gene or said fragment in an expressible format.

A still further aspect of the invention contemplates a method of reducing the expression of an LAR polypeptide of the RED protein superfamily in a plant comprising introducing to the genome of said plant a member selected from the group consisting of: an antisense molecule, a ribozyme, a PTGS molecule, and a co-suppression molecule, wherein said member comprises at least about 20 contiguous nucleotides of an LAR gene in an expressible format.

The present invention further extends to the use of the transformed plants and methods described herein to reduce the severity or incidence of bloat in pasture animals.

BRIEF DESCRIPTION OF THE DRAWINGS

FIG. 4 is a copy of a schematic representation showing the alignment of the *D. uncinatum* LAR polypeptide to other polypeptides of the RED protein superfamily. DuLAR, *D. uncinatum* LAR (SEQ ID NO: 29); MtIFR, *Medicago truncatula* isoflavone reductase (SEQ ID NO: 32); LaIFR, probable *Lupinis albus* 2'-hydroxyisoflavone reductase (SEQ ID NO: 33); PsIFR, *Pisum sativum* 2'hydroxyisoflavone reductase (SEQ ID NO: 34); GmIFR, *Glycine max* isoflavone reductase homologue-1 (SEQ ID NO: 35); CaIFR, *Cicer arietinum* NADPH:isoflavone oxidoreductase (SEQ ID NO: 36); StIFR, *Solanum tuberosum* isoflavone reductase homologue (SEQ ID NO: 37); NtIFR, *Nicotiana tabacum* reductase homologue (SEQ ID NO: 38); AtF1804, *Arabidopsis thaliana* isoflavone reductase homologue (SEQ ID NO: 39); AtF22F8, *A. thaliana* NADPH:isoflavone oxidoreductase-like protein (SEQ ID NO: 40); PtPCBER, *Pinus taeda* phenylcoumaran benzylic ether reductase PT1 (SEQ ID NO: 41); Th2PLR, *Tsuga heterophylla* pinoresinol-lariciresinol reductase TH2 (SEQ ID NO: 42); Tp1PCBER, *Thuja plicata* phenylcoumaran benzylic ether reductase homologue Tp1 (SEQ ID NO: 43); Th7PCBER, *Tsuga heterophylla* phenylcoumaran benzylic ether reductase homologue TH7 (SEQ ID NO: 44); Th6PCBER, *Tsuga heterophylla* phenylcoumaran benzylic ether reductase homologue TH6 (SEQ ID NO: 45); Th5PCBER, *Tsuga heterophylla* phenylcoumaran benzylic ether reductase homologue TH5 (SEQ ID NO: 46); Th4PCBER, *Tsuga heterophylla* phenylcoumaran benzylic ether reductase homologue TH4 (SEQ ID NO: 47); Th3PCBER, *Tsuga heterophylla* phenylcoumaran benzylic ether reductase homologue TH3 (SEQ ID NO: 48); Th2PCBER, *Tsuga heterophylla* phenylcoumaran benzylic ether reductase homologue TH2 (SEQ ID NO: 49); Th1PCBER, *Tsuga heterophylla* phenylcoumaran benzylic ether reductase homologue TH1 (SEQ ID NO: 50); Fi1PCBER, *Forsythia X intermedia* phenylcoumaran benzylic ether reductase homologue Fi1 (SEQ ID NO: 51); Fi2PCBER, *Forsythia X intermedia* phenylcoumaran benzylic ether reductase homologue Fi2 (SEQ ID NO: 52); and PbPCBER, *Populus balsamifera* susp. *trichocarpa* phenylcoumaran benzylic ether reductase (SEQ ID NO: 53); U33318 *Zea mays* sulfur starvation induced isoflavone reductase-like (IRL) mRNA, complete cds (SEQ ID NO: 54); X92075, *S. tuberosum* mRNA for isoflavone reductase homologue (SEQ ID NO: 55); and Y12689, *C. paradisi* mRNA isoflavone reductase-like protein (SEQ ID NO: 56).

DETAILED DESCRIPTION OF THE PREFERRED EMBODIMENTS

Figure 1:
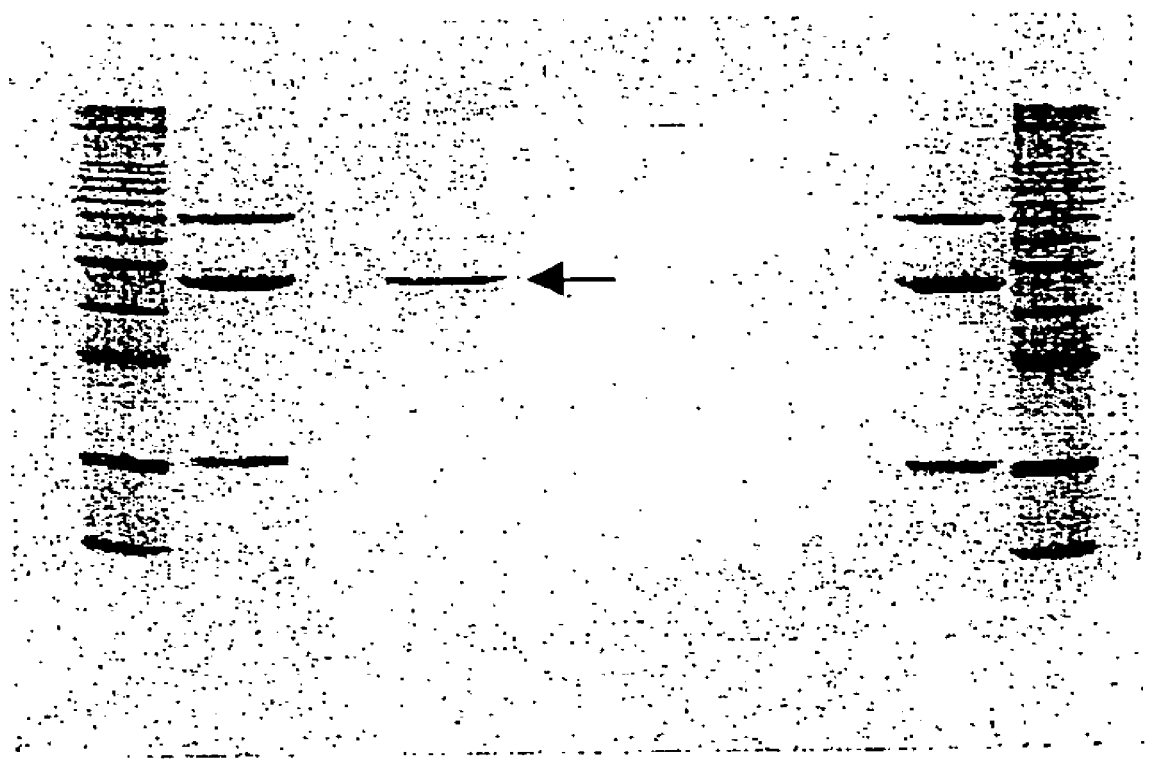
FIG. 1 is a copy of a photographic representation of a Coomassie Brilliant Blue G250-stained SDS/polyacrylamide gel of the purified LAR protein from *D. uncinatum*. Lanes 1 and 5, molecular weight standard proteins comprising a 10 kDa molecular weight ladder (Gibco BRL); Lanes 2 and 4, 1 μg each of bovine serum albumin protein, ovalbumin, and soybean trypsin inhibitor proteins; and Lane 3, purified LAR protein. The arrow indicates the position of the 48 kDa LAR polypeptides.

One aspect of the present invention provides an isolated LAR polypeptide of the RED protein superfamily or a truncated form thereof or a fragment comprising at least about 10 contiguous amino acids in length derived from said LAR polypeptide.

Preferably, the isolated LAR polypeptide of the invention is characterized by one, two or three of the following features:

(i) It has an isoelectric point in the range of about 5.7 to about 5.8, and, more particularly, an isoelectric point of about 5.7 or about 5.8, as determined by two-dimensional SDS/PAGE;

(ii) It has an estimated molecular weight of about 48 kDa as determined by SDS/PAGE; and (iii) It has LAR enzyme activity.

The range provided herein for the estimated molecular weight of an LAR polypeptide of the RED protein superfamily is merely an approximation as determined by SDS/PAGE, and some variation in this estimate may occur, for example, under different conditions employed to determine said molecular weight, and between different species of origin. Additionally, proteolytic cleavage that does not significantly reduce enzyme activity may modify the estimated molecular weight of the LAR polypeptide. Accordingly, the invention is not limited by this feature.

Preferably, the LAR of the invention utilizes NADPH or NADH as a cofactor, in a reaction selected from the group consisting of:

(i) the conversion of 2,3-trans-3,4-cis-leucocyanidin to catechin;

(ii) the conversion of 3,4-cis-leucodelphinidin to gallocatechin; and (iii) the conversion of 3,4-cis-leucopelargonidin to afzelechin.

Preferably, the isolated protein is substantially free of conspecific proteins.

In a particularly preferred embodiment of the invention, the isolated LAR polypeptide of the invention is from *D. uncinatum*. The inventors have isolated at least two isoforms of the *D. uncinatum* enzyme, one of which comprises the amino acid sequence set forth in SEQ ID NO: 29.

Fragments of the isolated LAR polypeptide of the present invention are useful for the purposes of producing antibodies against one or more B-cell or T-cell epitopes of LAR, which antibodies may be used, for example, to identify cDNA clones encoding homologues of the exemplified cDNA clone provided herein, or to inhibit LAR enzyme activity in vivo or in vitro, or in immunohistochemical staining to determine the site of expression of LAR. Alternatively, fragments of the entire LAR polypeptide may be useful as competitive inhibitors of the native enzyme, particularly if they include the substrate binding site(s) of the enzyme. Those skilled in the art will appreciate that longer fragments than those consisting of only 10 amino acids in length may have improved utility than shorter fragments. Preferably, a fragment of an LAR polypeptide of the invention will comprise at least about 20 contiguous amino acid residues, and more preferably at least about 50 contiguous amino acid residues derived from the native enzyme.

Fragments derived from the internal region, the N-terminal region, or the C-terminal region of the native enzyme are encompassed by the present invention.

The present invention also extends to truncated forms of the LAR polypeptide of the RED protein superfamily. The term "truncated form" as used herein means a non-full-length LAR polypeptide, particularly one which retains the LAR enzyme activity of the full-length LAR polypeptide. In one embodiment, the truncated form of the LAR polypeptide comprises an amino acid sequence as set forth in SEQ ID NO:29 truncated by deletion of about 60 to 70, preferably about 65, C-terminal residues. One preferred embodiment of the truncated form of the LAR polypeptide comprises amino acids 1–317 of SEQ ID NO:29.

Fragments and isolated polypeptides contemplated herein include modified peptides in which ligands are attached to one or more of the amino acid residues contained therein, such as a hapten; a carbohydrate; an amino acid, such as, for example, lysine; a peptide or polypeptide, such as, for example, keyhole limpet haemocyanin (KLH), ovalbumin, or phytohaemagglutinin (PHA); or a reporter molecule, such as, for example, a radionuclide, fluorescent compound, or antibody molecule. Glycosylated, fluorescent, acylated or alkylated forms of the subject peptides are particularly contemplated by the present invention. Additionally, homopolymers or heteropolymers comprising two or more copies of the subject LAR polypeptides are contemplated herein. Procedures for derivatizing peptides are well-known in the art.

Notwithstanding that the present inventors have exemplified the LAR polypepude of the invention by providing at least two LAR isoforms from *D. uncinatum*, the invention clearly extends to isolated LAR polypeptides from other plant species, and, in the case of isolated proteins prepared by recombinant means, from any cellular source that supports the production of a recombinant LAR protein.

Accordingly, the present invention clearly encompasses homologues of the LAR polypeptide and peptide fragments described herein.

In the present context, "homologues" of an LAR polypeptide refer to those polypeptides, enzymes or proteins which have a similar catalytic activity to the *D. uncinatum* LAR enzyme, notwithstanding any amino acid substitutions, additions or deletions thereto. A homologue of the *D. uncinatum* LAR polypeptide exemplified herein may be isolated or derived from the same or another plant species.

For example, the amino acids of a homologous polypeptide may be replaced by other amino acids having similar properties, for example hydrophobicity, hydrophilicity, hydrophobic moment, charge or antigenicity, and so on. Substitutions encompass amino acid alterations in which an amino acid is replaced with a different naturally-occurring or a non-conventional amino acid residue.

Conservative amino acid substitutions are particularly contemplated herein for the production of homologues of the *D. uncinatum* LAR enzyme, such as, for example Gly←→Ala; Ser←→Thr; Met←→Val←→Ile←→Leu; Asp←→Glu; Lys←→Arg; Asn←→Gln; or Phe←→Trp←→Tyr. Such conservative substitutions will not generally inactivate the enzyme activity of an LAR polypeptide.

The non-conservative substitution of one or more amino acid residues in the native *D. uncinatum* LAR polypeptide for any other naturally-occurring amino acid, or for a non-naturally occurring amino acid analogue, is also contemplated herein. Such substitutions generally involve modifications to charge, in particular charge reversals, or changes to the hydrophobicity of the LAR polypeptide, and, more preferably, will modify the activity of the polypeptide.

Amino acid substitutions are typically of single residues, but may be of multiple residues, either clustered or dispersed.

Homologues of the isolated *D. uncinatum* LAR polypeptides, wherein amino acid resides are deleted, or alternatively, additional amino acid residues are inserted are also contemplated herein. Amino acid deletions will usually be of the order of about 1–10 amino acid residues, and may occur throughout the length of the polypeptide. Insertions may be of any length, and may be made to the N-terminus, the C-terminus or be internal. Generally, insertions within the amino acid sequence will be smaller than amino-or carboxyl-terminal fusions and of the order of 1–4 amino acid residues.

Preferably, an isolated LAR polypeptide of the RED protein superfamily will comprise an amino acid sequence comprising one or more of the following amino acid signatures:

(i) Leu-$Xaa_1$-$Xaa_1$-Gly-$Xaa_2$-Thr-Gly-$Xaa_3$-$Xaa_1$-Gly-$Xaa_4$, wherein $Xaa_1$ is selected from the group consisting of: Met, Ile, Val, and Leu; $Xaa_2$ is Ala or Gly; $Xaa_3$ is Phe or Tyr; and $Xaa_4$ is Gln or Asn (SEQ ID NO: 8), and still more preferably, the signature: Leu-Val-Val-Gly-Gly-Thr-Gly-Phe-Ile-Gly-Gln (SEQ ID NO: 9);

(ii) Lys-$Xaa_1$-$Xaa_2$-$Xaa_2$-Pro-Ser-Glu-Phe-$Xaa_3$-$Xaa_4$-Asp, wherein $Xaa_1$ is Arg or Lys; $Xaa_2$ is Phe or Tyr; $Xaa_3$ is Ala or Gly; and $Xaa_4$ is a basic or half basic amino acid residue (SEQ ID NO: 10), and still more preferably, the signature: Lys-Lys-Phe-Leu-Pro-Ser-Glu-Phe-Gly-His-Asp (SEQ ID NO: 11);

(iii) $Xaa_1$-Asp-$Xaa_2$-$Xaa_3$-$Xaa_4$-Leu-Asn-Lys, wherein $Xaa_1$ is Asp or Asn; $Xaa_2$ is selected from the group consisting of: Met, Ile, Val, and Leu; $Xaa_3$ is Arg or Lys; and $Xaa_4$ is Ser or Thr (SEQ ID NO: 12), and still more preferably, the signature: Asp-Asp-Ile-Arg-Thr-Leu-Asn-Lys (SEQ ID NO: 13); and (iv) $Xaa_1$-Tyr-Pro-$Xaa_2$-$Xaa_2$-$Xaa_3$-$Xaa_4$, wherein $Xaa_1$ is selected from the group consisting of: Val, Ile, Met, and Leu; $Xaa_2$ is Asp or Glu; $Xaa_3$ is Arg or Lys; and $Xaa_4$ is Phe or Tyr (SEQ ID NO: 14), and still more preferably, the signature: Leu-Tyr-Pro-Asp-Glu-Lys-Phe (SEQ ID NO: 15).

Alternatively, or in addition, an LAR polypeptide of the present invention will comprise an amino acid sequence having at least about 40% identity overall to an amino acid sequence selected from the group consisting of: SEQ ID NOs: 16–23, 27, and 29–31. Preferably, the LAR polypeptide of the present invention will comprise an amino acid sequence having at least about 40% identity overall to the amino acid sequence of the full-length *D. uncinatum* LAR polypeptide exemplified in SEQ ID NO: 29.

Preferably, the percentage identity overall to an amino acid sequence presented herein is at least about 50%, more preferably at least about 60%, even more preferably at least about 70%, even more preferably at least about 80%, even more preferably at least about 90%, and even more preferably at least about 95% or 99%.

Those skilled in the art will be aware that the particular percentage identity between two or more amino acid sequences in a pairwise or multiple alignment may vary depending on the occurrence, and length, of any gaps in the alignment. Preferably, for the purposes of defining the percentage identity to the amino acid sequences listed herein, reference to a percentage identity between two or more amino acid sequences shall be taken to refer to the number of identical residues between said sequences as determined using any standard algorithm known to those skilled in the art that maximizes the number of identical residues and minimizes the number and/or length of sequence gaps in the alignment. For example, amino acid sequence identities or similarities may be calculated using the GAP programme and/or aligned using the PILEUP programme of the Computer Genetics Group, Inc., University Research Park, Madison, Wis., United States of America (Devereaux et al, 1984). The GAP programme utilizes the algorithm of Needleman and Wunsch (1970). Alternatively or in addition, wherein more than two amino acid sequences are being compared, the ClustalW programme of Thompson et al (1994) can be used.

Those skilled in the art will be aware that the percentage identity to a particular sequence is related to the phylogenetic distance between the species from which the sequences are derived, and as a consequence, those sequences from distantly-related species to *D. uncinatum* are likely to have functionally-equivalent LAR polypeptides to the *D. uncinatum* LAR polypeptide, albeit having a low percentage identity to SEQ ID NO: 29 at the amino acid sequence level. Such distantly-related LAR polypeptides may be isolated without undue experimentation using the isolation procedures described herein, and as a consequence, are clearly encompassed by the present invention.

Preferred sources of the LAR polypeptide of the present invention include any plant species known to produce tannins, and more particularly, catechin, in the seed coat, testa, pericarp, leaf, floral organ, or root. For example, preferred sources include those fodder or forage legumes, companion plants, food crops, trees, shrubs, or ornamentals selected from the group consisting of: *Acacia* spp., *Acer* spp., *Actinidia* spp., *Aesculus* spp., *Agathis* spp., *Albizia* spp., *Alsophila* spp., *Andropogon* spp., *Arachis* spp., *Areca* spp., *Astelia* spp., *Astragalus* spp., *Baikiaea* spp., *Betula* spp., *Bruguiera* spp., *Burkea* spp., *Butea* spp., *Cadaba* spp., *Calliandra* spp., *Camellia* spp., *Canna* spp., *Cassia* spp., *Centroema* spp., *Chaenomeles* spp., *Cinnamomum* spp., *Coffea* spp., *Colophospermum* spp., *Coronillia* spp., *Cotoneaster* spp., *Crataegus* spp., *Cupressus* spp., *Cyathea* spp., *Cydonia* spp., *Cryptomeria* spp., *Cymbopogon* spp., *Cynthea dealbata, Cydonia oblonga, Dalbergia monetaria, Davallia divaricata, Desmodium* spp., *Dicksonia squarosa, Diheteropogon amplectens, Dioclea* spp, *Dolichos* spp., *Dorycnium rectum, Echinochloa pyramidalis, Ehrartia dura*, spp., *Eleusine coracana, Eragrestis* spp., *Erythrina* spp, *Eucalyptus robusta, Euclea schimperi, Eulalia villosa, Fagopyrum* spp., *Feijoa sellowiana, Fragaria* spp., *Flemingia* spp, *Freycinetia banksii, Geranium thunbergii, Ginkgo biloba, Glycine javanica, Gliricidia* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissoluta, Indigo incarnata, Iris* spp., *Leptarrhena pyrolifolia, Lespediza* spp., *Leucaena leucocephala, Loudetia simplex, Lotonus bainesii, Lotus* spp., *Macrotyloma axillare, Malus* spp., *Manihot esculenta, Medicago sativa, Metasequoia glyptostroboides, Musa sapientum, Onobrychis* spp., *Ornithopus* spp., *Peltophorum africanum, Persea gratissima, Phaseolus atropurpureus, Phoenix canariensis, Phormium cookianum, Photinia* spp., *Picea glauca, Pinus* spp., *Podocarpus totara, Pogonarthria* spp., *Populus x euramericana, Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes* spp., *Robinia pseudoacacia, Rosa centifolia, Rubus* spp., *Salix* spp., *Schyzachyrium sanguineum, Sciadopitys verticillata, Sequoia sempervirens, Sequoiadendron giganteum, Sorghum bicolor, Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia sativa, Vitis vinifera, Watsonia pyramidata*, and *Zantedeschia aethiopica*.

Even more preferably, the LAR polypeptide of the invention is derived from a plant selected from the group consisting of: *D. uncinatum, Medicago sativa, Medicago truncatula, Trifolium repens, Lotus corniculatus, Lotus japonicus, Nicotiana tabacum, Vitis vinifera, Camellia sinensis, Hordeum vulgare, Sorghum bicolor, Populus trichocarpa, Forsythia X interrnedia, Thuja plicata, Pinus radiata, Pseudotsuga menziesii*, and *A. thaliana*.

The seeds of any plant, or a tissue, cell or organ culture of any plant, are also preferred sources of LAR.

The teaching provided herein clearly enables those skilled in the art to isolate an LAR polypeptide of plants without undue experimentation. For example, the amino acid sequence of the *D. uncinatum* LAR polypeptide, or the amino acid sequence of a fragment thereof, can be used to design antibodies for use in the affinity purification of immunologically cross-reactive proteins from other plants. Those skilled in the art will recognize that such immunologically cross-reactive proteins are likely to be LAR polypeptides, particularly if peptide fragments having amino acid sequences that are not highly-conserved between LAR and other RED proteins are used as immunogens to elicit the production of those antibodies. Alternatively, such antibodies can be used to isolate cDNA clones that express immunologically cross-reactive proteins according to any art-recognized protocol, such as, for example, the procedure disclosed by Huynh et al. (1985), and the expressed protein subsequently isolated or purified. The isolation or purification of the expressed protein is facilitated by expressing the LAR protein as a fusion protein with a tag, such as, for example, glutathion-S-transferase, FLAG, or oligo-Histidine motifs. Alternatively, the LAR protein may be expressed as an inclusion body, or targeted to a specific organelle (e.g. a plastid, vacuole, mitochondrion, nucleus, etc) to facilitate subsequent isolation. Procedures for recombinantly-expressing proteins, and for sequestering and/or purifying recombinantly-expressed proteins, are well-known to those skilled in the art. Accordingly, the present invention is not to be limited by the mode of purification of exemplified herein.

In a preferred embodiment, the present invention provides a method of isolating an LAR polypeptide of the RED protein superfamily from a cell, said method comprising at least three purification steps each of which employs an affinity matrix having a different dye ligand attached thereto, and a purification step that employs an ion exchange matrix.

The term "purification step" shall be taken to mean a process that results in an increase in protein purity as determined by a comparison of the LAR enzyme specific activities of the starting material and product of the process. Preferably, a purification step will yield an increase of at least 5-fold in enzyme specific activity, more preferably an increase of at least about 10-fold, and even more preferably at least about 20-fold.

The purification steps according to this embodiment of the invention need not be sequential purification steps. For example, they may be separated by one or more intervening procedures used to prepare the protein sample, or by one or more other purification steps.

The term "affinity matrix" means any insoluble matrix, such as, for example, sepharose, superose, sephacryl, agarose, or cellulose, having one or more bound ligands capable of specifically, and preferably, reversibly, associating with a molecule to be purified, separated, or isolated. Preferably, the ligand is a cofactor or substrate analogue, inhibitor, cofactor, antibody molecule, cell or cellular component, polysaccharide, lectin, glycoprotein, cell surface receptor, lectin, or binding partner of the molecule of interest.

Preferably, the dye ligand is a dye having an affinity for LAR selected from the group consisting of:

(i) a dye ligand having low affinity for LAR to which LAR may not bind, or binds weakly, such as, for example, Bayer 4 (see below (ii) a dye ligand having an intermediate binding affinity for LAR, such as, for example, Cibacron Orange F-R (Ciba-Geigy), to which LAR binds and is eluted using a cofactor of LAR; and (iii) a dye ligand having high affinity for LAR, to which LAR binds and is eluted using a salt, such as, for example, NaCl or KCl.

More preferably, (ii) supra uses less than 1 mM cofactor to release LAR from the dye ligand, or (iii) supra uses about 1M NaCl to release LAR from the dye ligand.

Other ligands, including any NADP(H) analogues, are not excluded in performing this embodiment of the invention, and are readily available from public sources to the skilled artisan. Persons skilled in the art will also be aware of the procedures for using such affinity matrices, such as, for example, as described by Scopes (1994).

As used herein, the term "ion exchange" means any process involving the separation of a molecule from other molecules, or the isolation or concentration of a single molecule, based upon the charge of the molecule, or charge differences between the molecule being separated or isolated, and the other molecules.

An "ion exchange matrix" shall be taken to mean any insoluble matrix, such as, for example, sepharose, superose, sephacryl, agarose, or cellulose, having one or more bound charged groups capable of associating with a mobile counter ion that can be exchanged reversibly with another ion of the same charge. The mobile counter ion is generally in solution.

Any known ion exchange matrix may be employed, such as, for example, a cation exchange or anion exchange matrix. A cation exchange matrix is one which has a negatively charged functional group or ligand, and so binds to positively-charged amino acid residues in the protein solution (i.e. the mobile counter ion is a cation) and requires a mobile counter cation for elution of the bound protein. Conversely, an anion exchange matrix is one which has a positively charged functional group or ligand, and so binds to negatively-charged amino acid residues in the protein solution (i.e. the mobile counter ion is a cation) and requires a mobile counter anion for elution of the bound protein. Persons skilled in the art will be aware of the procedures for using such ion exchange matrices, such as, for example, as described by Scopes (1994).

Preferably an anion exchange matrix is used. Even more preferably, the anion exchange matrix is one to which LAR binds at low salt concentrations, and from which said LAR elutes at higher salt concentrations.

The anion used to elute LAR from the anion exchange matrix is preferably a chloride ion, such as, for example, in the form of a sodium salt or potassium salt.

As exemplified herein, the present inventors have shown that a purification step using the anion exchange matrix, MonoQ (Pharmacia), provides a significant step-purification of two *D. uncinatum* LAR polypeptides, wherein LAR binds to the matrix in the absence of a chloride salt and is eluted.

Preferably, said method further comprises one or more additional preliminary or intermediate or final steps selected from the group consisting of: a protein precipitation, a protein concentration, a protein desalting, an affinity purification, an ion exchange, and a gel filtration based upon molecular size or weight.

Preferably, the subject method comprises:
(i) preparing a crude cell extract in a suitable buffer solution;
(ii) incubating said crude cell extract with a precipitant for a time and under conditions sufficient to precipitate LAR enzyme activity and resuspending the precipitated protein in a suitable buffer solution;
(iii) subjecting the resuspended protein from (ii) to affinity chromatography on a matrix having a ligand with low affinity for LAR attached thereto, and collecting an unbound protein fraction having LAR activity;
(iv) subjecting the unbound protein fraction from (iii) to affinity chromatography on a matrix having a ligand with high affinity for LAR attached thereto, eluting said LAR using a salt, and desalting the eluted LAR protein;
(v) subjecting the desalted LAR protein obtained at (iv) to affinity chromatography using a matrix having a ligand with intermediate affinity for LAR attached thereto and eluting LAR protein using NADPH;
(vi) subjecting the LAR protein fraction obtained at (v) to chromatography on hydroxylapatite and isolating fractions having LAR activity; and
(vii) subjecting the LAR protein fraction obtained at (vi) to anion exchange chromatography and eluting LAR protein.

Preferably, the precipitant is ammonium sulfate or polyethylene glycol. Other protein precipitants are not excluded.

In a particularly preferred embodiment, there is provided a method of purifying an LAR polypeptide comprising:
(i) preparing a crude cell extract in a suitable buffer solution;
(ii) incubating said crude cell extract with polyethylene glycol for a time and under conditions sufficient to precipitate LAR enzyme activity and resuspending the precipitated protein in a suitable buffer solution;
(iii) subjecting the resuspended protein from (ii) to affinity chromatography on a matrix having a Procion Yellow H3R ligand attached thereto and collecting an unbound protein fraction having LAR activity;
(iv) subjecting the unbound protein fraction from (iii) to affinity chromatography on a matrix having a Bayer 4 ligand attached thereto (see below), eluting said LAR using a salt, and desalting the eluted LAR protein;
(v) subjecting the desalted LAR protein obtained at (iv) to affinity chromatography using a matrix having a Cibacron Orange F-R ligand (Ciba-Geigy) attached thereto and eluting LAR protein using NADPH;
(vi) subjecting the LAR protein fraction obtained at (v) to chromatography on hydroxylapatite and isolating fractions having LAR activity; and
(vii) subjecting the LAR protein fraction obtained at (vi) to anion exchange chromatography on MonoQ and eluting LAR protein.

The "Bayer 4" dye ligand has the following chemical structure, and analogues of that structure for use in performing the invention will be readily available to the

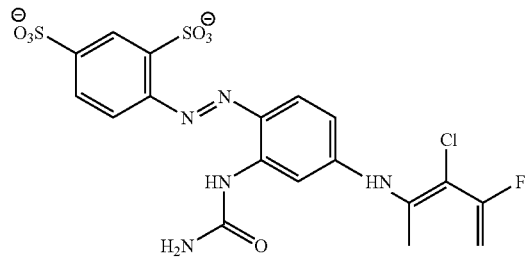

skilled person:

Optionally, wherein a homogeneous protein preparation is not required, the fraction obtained at (v), or by the performance of only the affinity purification steps supra may be sufficient.

Optionally, where the biochemical activity of the enzyme is not essential for its intended purpose, for example in amino acid sequence determinations, the enzyme obtained at (vii) may be further subjected to SDS/PAGE and/or IEF to isolate a proanthocyanidin biosynthetic enzyme which is characterized by an estimated molecular weight of approximately 48,000 or an isoelectric point of about 5.7 or about 5.8.

The composition of the buffers used for each of the steps of the subject method may be determined by the person skilled in the art, without undue experimentation, the only requirement of such buffer compositions being that they are suitable for the maintenance of activity of the enzyme being purified under the chromatographic procedures employed. Preferably, the buffer compositions include at least one, preferably two, more preferably three, and more preferably four, protease inhibitors to prevent proteolysis of the enzyme during the purification procedure. Preferred protease inhibitors for this purpose are selected from the group consisting of: leupeptin, EDTA, pepstatin, E64, and phenylmethylsulfonyl fluoride (PMSF).

This embodiment of the invention is not limited by the cell from which the LAR polypeptide is isolated, because, as stated supra, LAR can be expressed in a recombinant form in practically any cell type, such as, for example, a bacterial cell, insect cell, yeast cell, plant cell, or animal cell. In the case of naturally-occurring LAR polypeptides, the preferred cellular source of the polypeptide will be a plant cell, such as, for example, a plant selected from the list supra.

A further aspect of the present invention provides an antibody molecule prepared by a process comprising immunizing an animal with an immunologically-effective amount of an isolated LAR polypeptide of the RED protein superfamily or a truncated form thereof or a fragment comprising at least about 10 contiguous amino acids in length of said LAR polypeptide, and isolating a monoclonal or polyclonal antibody from said animal.

This aspect of the invention clearly extends to any monoclonal or polyclonal antibody that binds to an LAR polypeptide of the RED protein superfamily or to a truncated form thereof or to a fragment comprising at least about 10 contiguous amino acids in length of said LAR polypeptide.

The term "antibody" as used herein, is intended to include fragments thereof which are also specifically reactive with an LAR polypeptide of the present invention, or with a truncated form or fragment thereof as described herein. Antibodies can be fragmented using conventional techniques and the fragments screened for utility in the same manner as for whole antibodies. For example, F(ab')2 fragments can be generated by treating antibody with pepsin. The resulting F(ab')2 fragment can be treated to reduce disulfide bridges to produce Fab' fragments.

Those skilled in the art will be aware of how to produce antibody molecules when provided with the LAR polypeptide or a truncated form or a fragment thereof, according to the embodiments described herein. For example, by using a polypeptide of the present invention, polyclonal antisera or monoclonal antibodies can be made using standard methods. A mammal, (e.g., a mouse, hamster, or rabbit) can be immunized with an immunogenic form of the polypeptide which elicits an antibody response in the mammal. Techniques for conferring immunogenicity on a polypeptide include conjugation to carriers or other techniques well known in the art. For example, the polypeptide can be administered in the presence of adjuvant. The progress of immunization can be monitored by detection of antibody titers in plasma or serum. Standard ELISA or other immunoassay can be used with the immunogen as antigen to assess the levels of antibodies. Following immunization, antisera can be obtained and, if desired IgG molecules corresponding to the polyclonal antibodies may be isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (1975) as well as other techniques such as the human B-cell hybridoma technique (Kozbor et al., 1983), the EBV-hybridoma technique to produce human monoclonal antibodies (Cole et al., 1985), and screening of combinatorial antibody libraries (Huse et al., 1989). Hybridoma cells can be screened immunochemically for production of antibodies which are specifically reactive with the polypeptide and monoclonal antibodies isolated.

As with all immunogenic compositions for eliciting antibodies, the immunogenically effective amounts of the polypeptides of the invention must be determined empirically. Factors to be considered include the immunogenicity of the native polypeptide, whether or not the polypeptide will be complexed with or covalently attached to a hapten, or carrier protein, or other carrier, and route of administration for the composition, i.e. intravenous, intramuscular, subcutaneous, etc., and the number of immunizing doses to be administered. Such factors are known in the vaccine art and it is well within the skill of immunologists to make such determinations without undue experimentation.

Preferably, the immunogen comprises the full-length LAR polypeptide or a truncated form thereof, or alternatively, a peptide comprising at least about 10 contiguous amino acids of the full-length polypeptide, such as, for example, an internal or N-terminal peptide fragment.

To enhance their immunogenicity, it is well-known to conjugate small peptide fragments to a hapten, such as, for example, dinitrophenyl (DNP), m-maleimidobenzoyl-N-hydroxyl-N-hybroxysuccinimide ester (MBS), or m-amino benzene sulphonate. A "hapten" is a non-immunogenic molecule that will react with a preformed antibody induced by an antigen or carrier molecule. Alternatively, the immunogenicity of small peptide fragments may be enhanced by conjugating the peptide to a carrier molecule, such as, for example, an antigenic peptide or protein, that may be conjugated to a hapten. As will be known to those skilled in the art, a "carrier" is generally an antigenic molecule. Preferred carrier molecules for this purpose include ovalbumin, KLH, and PHA.

In a particularly preferred embodiment, the immunogenic LAR peptide consists of the full-length polypeptide (i.e. SEQ ID NO: 29) or a truncated form thereof, or a fragment thereof comprising at least 12 or at least about 30 contiguous amino acid sequences thereof, such as, for example, the amino acid sequences set forth in any one of SEQ ID NOs: 16–23, 30 or 31.

In a particularly preferred embodiment, the amino acid sequence set forth in SEQ ID NO: 30 or 31 is conjugated to a suitable carrier protein.

It is within the scope of this invention to include any second antibodies (monoclonal, polyclonal or fragments of antibodies) directed to the first mentioned antibodies discussed above. Both the first and second antibodies may be used in detection assays or a first antibody may be used with a commercially available anti-immunoglobulin antibody.

Immunoassays are useful in detecting the presence of an LAR polypeptide of the RED protein superfamily, or synthetic peptide derivative thereof, in a cell, particularly a plant cell. Such an immunoassay is of particular use in determining whether a plant has the capability to produce condensed tannins. Immunoassays are also useful for the quantitation of said LAR polypeptide in a cell, in particular for screening genetic stocks for breeding programmes. The invention described herein extends to all such uses of immunointeractive molecules and diagnostic assays requiring said immunoassays for their performance.

A wide range of immunoassay techniques may be such as those described in U.S. Pat. Nos. 4,016,043, 4,424,279 and 4,018,653. These methods may be employed for detecting a proanthocyanidin biosynthetic enzyme or synthetic peptide derivative thereof. For example, an antibody against LAR or a synthetic peptide derivative thereof (hereinafter referred to as "the antigen"), can be immobilized onto a solid substrate to form a first complex and a biological sample derived from a test sample brought into contact with the bound antigen. After a suitable incubation, sufficient to allow formation of an antibody-antigen secondary complex, a second antibody capable of binding to the antigen and labeled with a reporter molecule is added and incubated, allowing sufficient time for the formation of a tertiary complex of antibody-the antigen-labeled antibody. Any unreacted material is washed away, and the presence of the tertiary complex is determined by observation of a signal produced by the reporter molecule.

The results may either be qualitative, by simple observation of the visible signal, or they may be quantitated by comparison with a control sample containing known amounts of immunogen.

Variations of this assay include a simultaneous assay, in which both sample and labeled antibody are added simultaneously to the bound antibody, or a reverse assay in which the labeled antibody and sample to be tested are first combined, incubated and then added simultaneously to the bound antibody. These techniques are well known to those skilled in the art, and the possibility of minor variations will be readily apparent. The antibodies may be monoclonal or polyclonal.

The solid substrate is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well known in the art and generally consist of cross-linking covalently binding or physically adsorbing the molecule to the insoluble carrier.

As used herein, the term "reporter molecule" shall be taken to mean a molecule which, by its chemical nature, produces an analytically identifiable signal which allows the detection of antigen-bound antibody. Detection may be either qualitative or quantitative. The most commonly used reporter molecule in this type of assay is an enzyme, fluorophore, or radionuclide. In the case of an enzyme immunoassay, the report molecule is an enzyme, preferably conjugated to the second antibody. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable color change. It is also possible to employ fluorogenic substrates, which yield a fluorescent product.

Conjugation of a hapten, carrier, or reporter molecule, can be achieved using glutaraldehyde, or periodate. As will be readily recognized, however, a wide variety of different conjugation techniques exist which are readily available to the skilled artisan.

Alternatively, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic color visually detectable with a light microscope. As in the EIA, the fluorescent labeled antibody is allowed to bind to the first antibody-hapten complex. After washing off the unbound reagent, the remaining complex is then exposed to the light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose.

Those skilled in the art will recognize that cross-reactive proteins (i.e. proteins that bind to anti-LAR antibodies) are most likely to be LAR polypeptides, particularly if peptide fragments having amino acid sequences that are not highly-conserved between LAR and other RED proteins are used as immunogens to elicit the production of the antibodies. Accordingly, the antibodies described herein are useful for isolating or purifying LAR from any plant, by standard procedures of affinity purification using antibodies. Alternatively, they are used for isolating nucleic acid expressing said LAR, from any source, using any art-recognized procedure, such as, for example, the procedure disclosed by Huynh et al. (1985). Alternatively, the antibodies can be used to immunoprecitiate or inhibit LAR enzyme activity present in cell extracts in vitro. Alternatively, they can be used to localize LAR activity in cells, such as, for example, by immunohistochemical staining of plant tissue sections.

A further aspect of the present invention provides an isolated nucleic acid molecule comprising a nucleotide sequence that encodes a member selected from the group consisting of: (i) an LAR polypeptide of the RED protein superfamily; (ii) a truncated form of said LAR polypeptide; (iii) a fragment comprising at least about 10 contiguous amino acids of said LAR polypeptide; and (iv) a nucleotide sequence that is complementary to a sequence encoding (i), (ii) or (iii).

The isolated nucleic acid molecule of the invention can be derived from any plant species. The present invention is not to be limited by the species origin of nucleic acid encoding the LAR pdlypeptide. Without limiting the scope of the invention, preferred plant sources include those plants referred to in the index to the International Code of Botanical Nomenclature (Tokyo Code) as adopted by the Fifteenth International Botanical Congress, Yokohama, August-September 1993 (published as International Code of Botanical Nomenclature (Tokyo Code) Regnum Vegetabile 131, Koeltz Scientific Books, Königstein, ISBN 3-87429-367-X or 1-878762-664 or 80-901699-1-0). More preferably, the isolated nucleic acid of the invention is derived from a plant listed supra.

Even more preferably, the nucleic acid of the invention is derived from a plant selected from the group consisting of: *D. uncinatum, Medicago sativa, Medicago truncatula, Trifolium repens, Lotus corniculatus, Lotus japonicus, Nicotiana tabacum, Vitis vinifera, Camellia sinensis, Hordeum vulgare, Sorghum bicolor, Populus trichocarpa, Forsythia X internedia, Thuja plicata, Pinus radiata, Pseudotsuga menziesii,* and *A. thaliana.* In a particularly preferred embodiment, the isolated nucleic acid molecule of the invention is derived from *Desmodium uncinatum.*

The nucleic acid of the invention may be in the form of RNA; or DNA, such as, for example, single-stranded or double-stranded cDNA, genomic DNA, single-stranded or double-stranded synthetic oligonucleotides, or DNA amplified by polymerase chain reaction (PCR); or a mixed polymer comprising RNA and DNA.

Nucleic acid of the present invention is derived by organic synthesis based upon the nucleotide sequence of a naturally-occurring LAR gene, or from an LAR gene per se. Reference herein to a "LAR gene" is to be taken in its broadest context and includes a member selected from the group consisting of:

(i) a classical genomic gene encoding all or part of an LAR polypeptide of the RED protein superfamily, and consisting of transcriptional and/or translational regulatory sequences and/or a coding region and/or untranslated sequences (i.e. introns, 5'- and 3'- untranslated sequences);

(ii) mRNA or cDNA encoding all or part of an LAR polypeptide of the RED protein superfamily, said mRNA or CDNA corresponding to the coding regions (i.e. exons) and 5'- and 3'-untranslated sequences of the genomic gene;

(iii) a synthetic or fusion molecule encoding all or part of an LAR polypeptide of the RED protein superfamily; and (iv) a complementary nucleotide sequence to any one of (i) to (iii).

Preferred LAR genes of the present invention are derived from naturally-occurring sources using standard recombinant techniques, such as, for example, mutagenesis, to introduce single or multiple nucleotide substitutions, deletions and/or additions relative to the wild-type sequence.

It is clearly within the scope of the present invention to include any nucleic acid comprising a nucleotide sequence complementary to an LAR gene as defined herein, in particular complementary nucleotide sequences that are useful as hybridization probes, or amplification primers, for isolating or identifying an LAR gene, or for reducing the level of expression of an endogenous LAR gene in a cell, tissue, organ, or whole plant. Such complementary nucleotide sequences may be in the form of RNA, such as, for example, antisense mRNA, or a ribozyme; DNA, such as, for example, single-stranded or double-stranded cDNA, genomic DNA, single-stranded or double-stranded synthetic oligonucleotides, or DNA amplified by polymerase chain reaction (PCR); or a mixed polymer comprising RNA and DNA. As will be known to those skilled in the art, sequences complementary to the coding region and/or non-oding region of a gene may be useful for such applications.

An antisense molecule is nucleic acid comprising a nucleotide sequence that is complementary to mRNA, or a DNA strand, that encodes protein, albeit not restricted to sequence having complementarity to the protein-encoding region. Preferred antisense molecules comprise RNA capable of hybridizing to mRNA encoding all or part of an LAR polypeptide of the RED protein superfamily, such as, for example, to prevent translation of said mRNA in a cell.

In the present context, a "ribozyme" is a synthetic RNA molecule which comprise one or two hybridizing arms, of about 5–20 contiguous nucleotides in length, capable of hybridizing to mRNA encoding an LAR polypeptide of the RED protein superfamily, and possessing an endoribonuclease activity that is capable of autocatalytically-cleaving said mRNA. A complete description of the function of ribozymes is presented by Haseloff and Gerlach (1988) and contained in International Patent Application No. WO89/05852. As with antisense molecules, ribozymes may target regions in the mRNA other than those of the protein-encoding region, such as, for example, in the untranslated region of an LAR gene.

The term "untranslated region" in this context means a region of a genomic gene or cDNA that is capable of being transcribed in a cell however not capable of being translated into an amino acid sequence of an LAR polypeptide of the RED protein superfamily. Accordingly, the term "untranslated region" includes nucleic acid comprising a nucleotide sequence derived from the 5'-end of mRNA to immediately preceding the final residue of the ATG translation start codon; nucleic acid comprising a nucleotide sequence derived from the second nucleotide residue of the final codon preceding the translation stop site to the 3'-end of mRNA; and any intron sequence that is cleaved from a primary mRNA transcript during mRNA processing.

The present invention further encompasses within its scope nucleic acid molecules comprising a first nucleotide sequence derived from mRNA, or a DNA strand, encoding an LAR polypeptide, and a second nucleotide sequence complementary to mRNA, or a DNA strand, encoding LAR, such as for example, in the form of a post-transcription gene silencing (PTGS) molecule, wherein the first and second sequences are linked in head-to-head or tail-to-tail configuration. As with antisense molecules or ribozymes, such molecules need not be derived exclusively from the open reading frame of an LAR gene. Preferred PTGS molecules will have a region of self-complementarity and be capable of forming a hairpin loop structure, such as those described in International Patent Application No. PCT/IB99/00606. Whilst not being bound by any theory or mode of action, a PTGS molecule has the potential to sequester sense LAR-encoding mRNA in a cell, such that single-stranded regions of the sequestered mRNA are rapidly degraded and/or a translationally-inactive complex is formed.

Preferred nucleic acid encoding an LAR polypeptide of the RED protein superfamily will be in the form of sense nucleic acid. In the present context, the term "sense nucleic acid" shall be taken to mean RNA or DNA comprising a nucleotide sequence derived from the strand of DNA or RNA that encodes a full-length LAR polypeptide of the RED protein superfamily, or a part thereof, including both coding and non-coding sequences. As will be known to those skilled in the art, sense nucleic acid may be used to for the purposes of ectopically expressing mRNA, or protein, in a cell, or alternatively, to down-regulate expression (e.g. co-suppression), or to identify or isolate an LAR gene, or to identify or isolate complementary sequences, such as, for example, antisense mRNA. As will be known to those skilled in the art, "co-suppression" is the reduction in expression of an endogenous gene that occurs when one or more copies of said gene, or one or more copies of a substantially similar gene, are introduced into the cell. As will be known to those skilled in the art, whilst the coding region of a gene is required to ectopically-express protein in a cell, the coding region and/or non-coding region of a gene may be useful for other applications referred to herein.

Sense nucleic acid molecules will preferably comprise the full-length open reading frame of an endogenous LAR gene, however may be less than full-length. It will be apparent from the definition of the term "LAR gene" provided herein above, that the present invention encompasses within its scope any nucleic acid fragment of the full-length open reading frame of an LAR gene, that is at least useful as a hybridization probe or amplification primer for isolating an LAR gene, or for modifying the level of expression of an endogenous LAR gene. In fact, the inventors have provided several fragments of the LAR gene that can be used in such procedures.

Preferred fragments of an LAR gene of the invention, for isolating or identifying homologous genes in the same or another species, are derived from the open reading frame. In the present context, an "open reading frame" is any nucleotide sequence encoding an amino acid sequence of an LAR polypeptide, and preferably, at least about 10 contiguous amino acids of an LAR polypeptide.

As will be known to those skilled in the art, where homologous LAR gene sequences are from divergent species to the species from which the fragment is derived, fragments of at least about 20 nucleotides in length from within the open reading frame of the LAR gene, more preferably at least about 30–50 nucleotides in length, and more preferably at least about 100 nucleotides in length, or 500 nucleotides in length, are preferred.

In the case of fragments for isolating or identifying an identical target LAR gene, or an LAR gene from a closely-related species, the fragment may be derived from any part of a known LAR gene, such as, for example, from the open reading frame, an untranslated region, or an intron, or promoter sequence.

In the present context, the term "promoter" means a nucleotide sequence comprising a transcriptional regulatory sequence derived from an LAR gene, such as, for example, the TATA box which is required for accurate transcription initiation, with or without a CCAAT box sequence and additional cis-acting regulatory elements (i.e. upstream activating sequences, enhancers and silencers) that may alter LAR gene expression in response to developmental and/or external stimuli, or in a tissue-specific manner.

Preferably, a nucleotide sequence that encodes an LAR polypeptide of the RED protein superfamily or a complementary nucleotide sequence thereto is selected from the group consisting of:
(i) a nucleotide sequence having at least about 40% identity overall to a SEQ ID NO: 28;
(ii) a nucleotide sequence that encodes an LAR polypeptide having at least about 40% identity overall to the amino acid sequence set forth in SEQ ID NO: 29;
(iii) the nucleotide sequence of (i) or (ii) comprising a sequence selected from the group consisting of SEQ ID NOs: 24, 25, and 26;
(iv) the nucleotide sequence of (i) or (ii) comprising a sequence encoding an amino acid sequence selected from the group consisting of SEQ ID NOs: 9–23, 27, and 29–31;
(v) a nucleotide sequence that hybridizes under at least low stringency conditions to at least about 20 contiguous nucleotides complementary to a sequence selected from the group consisting of SEQ ID NOs: 24–26, and 28; and
(vi) a nucleotide sequence that is complementary to any one of (i) to (v).

Preferably, the percentage identity of a nucleotide sequence to SEQ ID NO: 28 is at least about 50%, more preferably at least about 60%, even more preferably at least about 70%, and even more preferably, at least about 80%, and still even more preferably at least about 90%.

Similarly, it is preferred for the percentage identity of an LAR polypeptide to the amino acid sequence set forth in SEQ ID NO: 29, is at least about 40%, more preferably about 50%, even more preferably at least about 60%, and even more preferably at least about 70%, and still even more preferably at least about 80%.

Preferably, a fragment of a nucleotide sequence will comprise sequences that encode polypeptides having RED protein signature domains as described herein, which are sufficient for isolating genes encoding LAR.

For the purposes of defining the level of stringency in a hybridization to any one of the nucleotide sequences disclosed herein, a low stringency may comprise a hybridization and/or a wash carried out using a salt concentration equivalent to SSC buffer in the range of 2×SSC to 6×SSC buffer; a detergent concentration in the range of 0.1% (w/v) SDS to 1% (w/v) SDS; and a temperature in the range of between ambient temperature to about 42° C. Those skilled in the art will be aware that several different hybridization conditions may be employed. For example, Church buffer (Church and Gilbert, 1984) may be used at a temperature in the range of between ambient temperature to about 45° C.

Preferably, the stringency of hybridization is at least moderate stringency, even more preferably at high stringency. Generally, the stringency is increased by reducing tne concentration of SSC buffer, and/or increasing the concentration of SDS in the hybridization buffer or wash buffer and/or increasing the temperature at which the hybridization and/or wash are performed. Conditions for hybridizations and washes are well understood by one normally skilled in the art. For example, a moderate stringency may comprise a hybridization and/or wash carried out using a salt concentration in the range of between about 1×SSC buffer and 2×SSC buffer; a detergent concentration of up to about 0.1% (w/v) SDS; and a temperature in the range of about 45° C. to 55° C. Alternatively, Church buffer may be used at a temperature of about 55° C., to achieve a moderate stringency hybridization. A high stringency may comprise a hybridization and/or wash using a salt concentration in the range of between about 0.1×SSC buffer and about 1×SSC buffer; a detergent concentration of about 0.1% (w/v) SDS; and a temperature of about 55° C. to about 65° C., or alternatively, a Church Buffer at a temperature of at least 65° C. Variations of these conditions will be known to those skilled in the art.

Clarification of the parameters affecting hybridization between nucleic acid molecules, is provided by Ausubel et al. (1987).

Although the present inventors have successfully isolated the *D. uncinatum* LAR gene using oligonucleotide primers of only about 20 nucleotides in length, those skilled in the art will recognize that the specificity of hybridization increases using longer probes, or primers, to detect genes in standard hybridization and PCR protocols. Such approaches are facilitated by the provision herein of full-length cDNAs from a number of diverse species. For example, persons skilled in the art are readily capable of aligning the nucleotide sequences or amino acid sequences provided herein to identify conserved regions thereof, to facilitate the identification of sequences from other species or organisms. For example, the conserved RED protein signatures may facilitate the preparation of a hybridization probe, or primer, comprising at least about 30 nucleotides in length. Accordingly, preferred nucleotide sequences according to this embodiment of the invention will hybridize to at least about 30 contiguous nucleotides, more preferably at least about 50 contiguous nucleotides, even more preferably at least about 100 contiguous nucleotides, and still even more preferably at least about 500 contiguous nucleotides, derived from SEQ ID NO: 28 or a complementary sequence thereto.

In a particularly preferred embodiment of the invention, a nucleotide sequence encoding an LAR polypeptide will hybridize to a probe or primer selected from the group consisting of:
(i) a probe or primer comprising a nucleotide sequence selected from the group consisting of: SEQ ID NOs: 24, 25, and 26;
(ii) a probe or primer comprising a nucleotide sequence that encodes the amino acid sequence set forth in SEQ ID NO: 27 or 29; and
(iii) a probe or primer comprising a nucleotide sequence complementary to (i) or (ii).

In a particularly preferred embodiment, the nucleic acid of the invention comprises the sequence set forth in SEQ ID NO: 28 or is complementary thereto.

The present invention clearly encompasses within its scope those nucleic acid molecules from organisms other than those plants specifically described herein that encode LAR polypeptides of the RED protein superfamily, and have sequence homology to the exemplified sequences of the invention. Accordingly, in a further embodiment, the present invention provides an isolated nucleic acid molecule comprising a nucleotide sequence that encodes an LAR polypeptide of the RED protein superfamily or a fragment thereof, wherein said nucleic acid molecule is isolated by a process comprising:
(i) hybridizing a probe or primer comprising at least about 20 contiguous nucleotides of SEQ ID NO: 28 or a degenerate or complementary nucleotide sequence thereto, to nucleic acid of plants;
(v) detecting said hybridization;
(vi) isolating the hybridized nucleic acid; and
(vii) determining the amino acid sequence encoded by the hybridized nucleic acid or the function of said amino acid sequence so as to determine that the hybridized nucleic acid encodes said LAR.

The use of probes or primers encoding fragments of the amino acid sequence set forth in SEQ ID NO: 29 are also contemplated herein, the only requirement being that such probes or primers are capable of hybridizing to an LAR gene.

The related sequence being identified may be present in a gene library, such as, for example, a cDNA or genomic gene library.

The library may be any library capable of maintaining nucleic acid of eukaryotes, such as, for example, a BAC library, YAC library, cosmid library, bacteriophage library, genomic gene library, or a cDNA library. Methods for the production, maintenance, and screening of such libraries with nucleic acid probes or primers, or alternatively, with antibodies, are well known to those skilled in the art. The sequences of the library are usually in a recombinant form, such as, for example, a cDNA contained in a virus vector, bacteriophage vector, yeast vector, baculovirus vector, or bacterial vector. Furthermore, such vectors are generally maintained in appropriate cellular contents of virus hosts.

In particular, cDNA may be contacted, under at least low stringency hybridization conditions or equivalent, with a hybridization-effective amount of a probe or primer derived from the nucleotide sequence set forth in SEQ ID NO: 28, or a complementary sequence thereto, or alternatively, with a probe or primer comprising a sequence set forth in any one of SEQ ID NOs: 24, 25, or 26, or complementary to any one of said sequences, and the hybridization detected using a detection means.

In one embodiment, the detection means is a reporter molecule capable of giving an identifiable signal (e.g. a radioisotope such as $^{32}P$ or $^{35}S$ or a biotinylated molecule) covalently linked to the isolated nucleic acid molecule of the invention. Conventional nucleic acid hybridization reactions, such as, for example, those described by Ausubel et al., are encompassed by the use of such detection means.

In an alternative method, the detection means is any known format of the polymerase chain reaction (PCR). According to this method, degenerate pools of nucleic acid "primer molecules" of about 20–50 nucleotides in length are designed based upon any one or more of the nucleotide sequences disclosed herein, or a complementary sequence thereto. In one approach related sequences (i.e. the "template molecule") are hybridized to two of said primer molecules, such that a first primer hybridizes to a region on one strand of the double-stranded template molecule and a second primer hybridizes to the other strand of said template, wherein the first and second primers are not hybridized within the same or overlapping regions of the template molecule and wherein each primer is positioned in a 5'- to 3'-orientation relative to the position at which the other primer is hybridized on the opposite strand. Specific nucleic acid molecule copies of the template molecule are amplified enzymatically, in a polymerase chain reaction (PCR), a technique that is well known to one skilled in the art. McPherson et al (1991) describes several formats of PCR.

The primer molecules may comprise any naturally occurring nucleotide residue (i.e. adenine, cytidine, guanine, and thymidine) and/or comprise inosine or functional analogues or derivatives thereof, capable of being incorporated into a polynucleotide molecule. The nucleic acid primer molecules may also be contained in an aqueous mixture of other nucleic acid primer molecules or be in a substantially pure form.

Preferably, the sequence detected according to this embodiment originates from a plant as listed supra.

The present invention clearly extends to any gene constructs that comprise the LAR gene of the present invention, such as, for example, any expression gene constructs produced for expressing said LAR gene in a bacterial, insect, yeast, plant, fungal, or animal cell.

Accordingly, a further aspect of the present invention is directed to a gene construct comprising an isolated nucleic acid that encodes an LAR polypeptide of the RED protein superfamily or a fragment thereof or complementary nucleotide sequence thereto Those skilled in the art will also be aware that expression of an LAR gene, or a complementary sequence thereto, in a cell, requires said gene to be placed in operable connection with a promoter sequence. The choice of promoter for the present purpose may vary depending upon the level of expression required and/or the tissue, organ and species in which expression is to occur.

Placing a nucleic acid molecule under the regulatory control of a promoter sequence means positioning said molecule such that expression is controlled by the promoter sequence. A promoter is usually, but not necessarily, positioned upstream, or at the 5'-end, of the nucleic acid molecule it regulates. Furthermore, the regulatory elements comprising a promoter are usually positioned within 2 kb of the start site of transcription of the gene. In the construction of heterologous promoter/structural gene combinations, it is generally preferred to position the promoter at a distance from the gene transcription start site that is approximately the same as the distance between that promoter and the gene it controls in its natural setting (ire., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance can also occur.

Examples of promoters suitable for use in gene constructs of the present invention include promoters derived from the genes of viruses, yeast, moulds, bacteria, insects, birds, mammals and plants, preferably those capable of functioning in isolated yeast or plant cells. The promoter may regulate expression constitutively, or differentially, with respect to the tissue in which expression occurs. Alternatively, expression may be differential with respect to the developmental stage at which expression occurs, or in response to external stimuli such as physiological stresses, or temperature.

Examples of promoters useful for expression in plants include the CaMV 35S promoter, NOS promoter, octopine synthase (OCS) promoter, *Arabidopsis thaliana* SSU gene promoter, the meristem-specific promoter (meri1), napin seed-specific promoter, actin promoter sequence, sub-clover stunt virus promoters (International Patent Application No. PCT/AU95/00552), and the like. In addition to the specific promoters identified herein, cellular promoters for so-called housekeeping genes are useful. Promoters derived from genomic gene equivalents of the cDNAs described herein are particularly contemplated for regulating expression of LAR genes, or complementary sequences thereto, in plants. Inducible promoters, such as, for example, a heat shock-inducible promoter, heavy metal-inducible promoter (e.g. metallotheinin gene promoter), ethanol-inducible promoter, or stress-inducible promoter; may also be used to regulate expression of the introduced nucleic acid of the invention under specific environmental conditions.

For certain applications, it is preferable to express the LAR gene of the invention specifically, in particular tissues of a plant, such as, for example, to avoid any pleiotropic effects that may be associated with expressing said gene throughout the plant. As will be known to the skilled artisan, tissue-specific or cell-specific promoter sequences may be required for such applications. For expression in particular plant tissues, reference is made to the publicly available or readily available sources of promoter sequences known to those skilled in the art.

For expression in yeast or bacterial cells, it is preferred that the promoter is selected from the group consisting of: GAL1, GAL10, CYC1, CUP1, PGK1, ADH2, PHO5, PRB1, GUT1, SP013, ADH1, CMV, SV40, LACZ, T3, SP6, T5, and T7 promoter sequences.

The gene construct may further comprise a terminator sequence and be introduced into a suitable host cell where it is capable of being expressed to produce a recombinant dominant-negative polypeptide gene product or alternatively, a co-suppression molecule, a ribozyme, gene silencing or antisense molecule.

The term "terminator" refers to a DNA sequence at the end of a transcriptional unit which signals termination of transcription. Terminators are 3'-non-translated DNA sequences containing a polyadenylation signal, which facilitates the addition of poly(A) sequences to the 3'-end of a primary transcript.

Terminators active in cells derived from viruses, yeast, moulds, bacteria, insects, birds, mammals and plants are known and described in the literature. They may be isolated from bacteria, fungi, viruses, animals and/or plants.

Examples of terminators particularly suitable for use in the gene constructs of the present invention include the nopaline synthase (NOS) gene terminator of *Agrobacterium tumefaciens*, the terminator of the Cauliflower mosaic virus (CaMV) 35S gene, the zein gene terminator from *Zea mays*, the Rubisco small subunit (SSU) gene terminator sequences, subclover stunt virus (SCSV) gene sequence terminators (International Patent Application No. PCT/AU95/00552), and the terminator of the *Flaveria bidentis* malic enzyme gene meA3 (International Patent Application No. PCT/AU95/00552).

Those skilled in the art will be aware of additional promoter sequences and terminator sequences suitable for use in performing the invention. Such sequences may readily be used without any undue experimentation.

The gene constructs of the invention may further include an origin of replication sequence which is required for replication in a specific cell type, for example a bacterial cell, when said gene construct is required to be maintained as an episomal genetic element (e.g. plasmid or cosmid molecule) in said cell.

Preferred origins of replication for use in bacterial cells include, but are not limited to, the f1-ori and co/E1 origins of replication. The 2-micron origin of replication may be used in gene constructs for use in yeast cells.

The gene construct may further comprise a selectable marker gene or genes that are functional in a cell into which said gene construct is introduced. As used herein, the term "selectable marker gene" includes any gene which confers a phenotype on a cell in which it is expressed to facilitate the identification and/or selection of cells which are transfected or transformed with a gene construct of the invention or a derivative thereof.

Suitable selectable marker genes contemplated herein include the ampicillin resistance ($Amp^r$), tetracycline resistance gene ($Tc^r$), bacterial kanamycin resistance gene ($Kan^r$), phosphinothricin resistance gene, neomycin phosphotransferase gene (nptII), hygromycin resistance gene, β-glucuronidase (GUS) gene, chloramphenicol acetyltransferase (CAT) gene and luciferase gene, amongst others.

In a preferred embodiment of the invention, the gene construct is a binary gene construct, more preferably a binary gene construct comprising a selectable marker gene selected from the group consisting of: bar, nptII and spectinomycin resistance genes. Those skilled in the art will be aware of the chemical compounds to which such selectable marker genes confer resistance.

In an even more preferred embodiment, the binary construct comprises the *Streptomyces hygroscopicus* bar gene, placed operably in connection with the CaMV 35S promoter sequence. Still more preferably, the binary construct comprises the *Streptomyces hygroscopicus* bar gene, placed operably in connection with the CaMV 35S promoter sequence and upstream of the terminator sequence of the octopine synthase (ocs) gene.

A further aspect of the invention contemplates an isolated cell comprising a heterologous LAR gene, preferably wherein said LAR gene is present in said cell in an expressible format.

As used herein, the word "cell" shall be taken to include an isolated cell, or a cell contained within organized tissue, a plant organ, or whole plant.

Preferably the cell is a bacterial cell, such as, for example, *E. coli* or *A. tumefaciens*, or a plant cell, such as a legume, more particularly a fodder or forage legume such as *Medicago* spp. and *Trifolium* spp. Even more preferably, the cell is an *Agrobacterium tumefaciens* strain carrying a disarmed Ti plasmid, such as, for example, the *Agrobacterium tumefaciens* strain is designated AGL1 (Lazo et al., 1991). However, as will be understood by those skilled in the art, the isolated nucleic acid of the present invention may be introduced to any cell and maintained or replicated therein, for the purposes of generating probes or primers, or to produce recombinant LAR protein, or a peptide derivative thereof.

Accordingly, the present invention is not limited by the nature of the cell.

Those skilled in the art will be aware that whole plants may be regenerated from individual transformed cells. Accordingly, the present invention also extends to any plant material which comprises a gene construct according to any of the foregoing embodiments or expresses a sense, anti-sense, ribozyme, PTGS or co-suppression molecule, and to any cell, tissue, organ, plantlet or whole plant derived from said material.

A further aspect of the invention contemplates a transformed plant comprising a non-endogenous LAR gene or fragment thereof introduced into its genome, or a nucleotide sequence that is complementary to said LAR gene or said fragment, in an expressible format.

The term "endogenous" as used herein refers to the normal complement of a stated integer which occurs in an organism in its natural setting or native context (i.e. in the absence of any human intervention, in particular any genetic manipulation).

The term "non-endogenous" as used herein shall be taken to indicate that the stated integer is derived from a source which is different to the plant material, plant cell, tissue, organ, plantlet or whole plant into which it has been introduced. The term "non-endogenous" shall also be taken to include a situation where genetic material from a particular species is introduced, in any form, into an organism belonging to the same species as an addition to the normal complement of genetic material of that organism.

Preferably, the transformed plant of the invention further expresses a non-endogenous LAR polypeptide of the RED protein superfamily. This aspect of the invention clearly extends to any plant parts, or progeny plants, that are derived from the primary transformed plant.

Preferably, the plant material, plant cell, tissue, organ, plantlet or whole plant comprises or is derived from a fodder crop, companion plant, food crop, tree, shrub or ornamental plant as described herein, or a tissue, cell or organ culture of any of said plants or the seeds of any of said plants, in particular a legume, more particularly a fodder and forage legume such as *Medicago* spp. and *Trifolium* spp.

The present invention extends to the progeny and clonal derivatives of a plant according to any one of the embodiments described herein.

As will be known those skilled in the art, transformed plants are generally produced by introducing a gene construct, or vector, into a plant cell, by transformation or transfection means. The isolated nucleic acid molecule of the invention, especially the LAR gene of the invention, or a gene construct comprising same, is introduced into a cell using any known method for the transfection or transformation of a plant cell. Wherein a cell is transformed by the gene construct of the invention, a whole plant may be regenerated from a single transformed cell, using methods known to those skilled in the art.

By "transfect" is meant that the LAR gene or a PTGS molecule, antisense molecule, co-suppression molecule, or ribozyme comprising sequences derived from the LAR gene, is introduced into a cell without integration into the cell's genome. Alternatively, a gene construct comprising said gene, said molecule, or said ribozyme, placed operably under the control of a suitable promoter sequence, can be used.

By "transform" is meant the LAR gene or a PTGS molecule, antisense molecule, co-suppression molecule, or ribozyme comprising sequences derived from the LAR gene, is introduced into a cell and integrated into the genome of the cell. Alternatively, a gene construct comprising said gene, said molecule, or said ribozyme, placed operably under the control of a suitable promoter sequence, can be used.

Means for introducing recombinant DNA into plant cells or tissue include, but are not limited to, direct DNA uptake into protoplasts (Krens et al, 1982; Paszkowski et al, 1984), PEG-mediated uptake to protoplasts (Armstrong et al, 1990), electroporation (Fromm et al., 1985), microinjection of DNA (Crossway et al., 1986), microparticle bombardment of tissue explants or cells (Christou et al, 1988; Sanford et al., 1987; Finer and McMullen, 1990; Finer et al., 1992; Sanford et al., 1993; Karunaratne et al., 1996; and Abedinia et al., 1997), vacuum-infiltration of tissue with nucleic acid, and T-DNA-mediated transfer from *Agrobacterium* to the plant tissue (An et al.1985; Herrera-Estrella et al., 1983a; 1983b; 1985).

For example, transformed plants can be produced by the method of in planta transformation method using *Agrobacterium tumefaciens* (Bechtold et al., 1993; Clough et al., 1998), wherein *A. tumefaciens* is applied to the outside of the developing flower bud and the binary vector DNA is then introduced to the developing microspore and/or macrospore and/or the developing seed, so as to produce a transformed seed. Those skilled in the art will be aware that the selection of tissue for use in such a procedure may vary, however it is preferable generally to use plant material at the zygote formation stage for in planta transformation procedures.

A method for the efficient introduction of genetic material into *Trifolium repens* and regeneration of whole plants therefrom is also described in International Patent Application No. PCT/AU97/00529, Voisey et al (1994), or Larkin et al., (1996).

Alternatively, microparticle bombardment of cells or tissues may be used, particularly in cases where plant cells are not amenable to transformation mediated by *A. tumefaciens*. In such procedures, microparticle is propelled into a cell to produce a transformed cell. Any suitable ballistic cell transformation methodology and apparatus can be used in performing the present invention. Stomp et al. (U.S. Pat. No. 5,122,466) or Sanford and Wolf (U.S. Pat. No. 4,945,050) discloses exemplary apparatus and procedures. When using ballistic transformation procedures, the genetic construct may incorporate a plasmid capable of replicating in the cell to be transformed. Exemplary microparticles suitable for use in such systems include 1 to 5 micron gold spheres. The DNA construct may be deposited on the microparticle by any suitable technique, such as by precipitation.

A whole plant may he regenerated from the transformed or transfected cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristeriatic tissue (e.g., apical meristem, axillary buds, and root meristems), and induced meristem tissue (e.g., cotyledon meristem and hypocotyl meristem).

The term "organogenesis", as used herein means a process by which shoots and roots are developed sequentially from a meristematic center.

The term "embryogenesis", as used herein, means a process by which shoots and roots develop together in a concerted fashion (not sequentially), whether from somatic cells or gametes.

The generated transformed plants may be propagated by a variety of means, such as by clonal propagation or classical breeding techniques. For example, a first generation (or T1) transformed plant may be selfed to give homozygous second generation (or T2) transformant and the T2 plants further propagated through classical breeding techniques.

The generated transformed organisms contemplated herein may take a variety of forms. For example, they may be chimeras of transformed cells and non-transformed cells; clonal transformants (e.g., all cells transformed to contain the expression cassette), grafts of transformed and untransformed tissues (e.g., in plants, a transformed rootstock grafted to an untransformed scion).

The nucleic acid of the invention, and gene constructs comprising same, are particularly useful for modifying levels of condensed tannins in plants. In this respect, the isolated nucleic acid of the invention placed in either the sense or the antisense orientation relative to a suitable promoter sequence, wherein said orientation will depend upon the desired end-result for which the gene construct is intended.

Such plants may exhibit a range of desired traits including, but not limited to improved bloat-safety for animals grazing thereupon (i.e. less propensity to induce bloating when ingested), increased efficiency of protein utilization in ruminants with concomitant higher productivity, improved disease- or pest-resistance.

As used herein, "higher productivity" shall be taken to refer to increased production in any biological product or secondary metabolite of an animal species, in particular a livestock animal selected from the list comprising sheep, goats, alpaca, cattle, dairy cattle, amongst others, which is at least partly attributable to said animal being grazed upon or otherwise fed a plant comprising a gene construct of the present invention. Preferably, higher productivity includes increased milk yield, increased meat production or increased wool production.

Food plants comprising higher levels of condensed tannins, which have been produced using the gene constructs of the present invention, afford the benefit of having a longer shelf life than otherwise. Whilst not being bound by any theory or mode of action, the longer shelf life of such food plants is due to the antioxidant and antimicrobial properties of condensed tannins. These effects also provide for the development of new and improved health foods or other foodstuffs with improved anti-oxidant activities and free radical scavenging properties, which are useful in the treatment or prevention of a range of diseases including, but not limited to cancer, rheumatoid arthritis or other inflammatory diseases.

For example, the introduction of additional copies of an LAR gene, in the sense orientation, and under the control of a strong promoter, is useful for the production of plants, in particular fodder and forage legumes, which exhibit increased condensed tannin content or more rapid rates of condensed tannin biosynthesis. In this regard, the present inventors have produced LAR gene sequences capable of expressing a functional LAR enzyme (e.g. SEQ ID NO: 28) useful for such an application.

Alternatively, the production of plants with increased levels of condensed tannins is made possible by the introduction thereto of an LAR gene encoding an LAR enzyme having a low $K_m$ for 2,3-trans-3,4-cis-leucoanthocyanidin and/or NADPH; and/or a high $V_{max}$, compared to the enzyme product of the endogenous gene.

Alternatively, gene constructs comprising an LAR gene in the sense orientation may be used to complement the existing range of proanthocyanidin genes present in a plant, thereby altering the composition or timing of deposition of condensed tannins. In a preferred embodiment, the proanthocyanidin gene from one plant species is used to transform a plant of a different species, thereby introducing novel proanthocyanidin biosynthetic metabolism to the second-mentioned plant species.

In a related embodiment, a recombinant fusion LAR polypeptide may be produced containing the active site from one LAR enzyme fused to another LAR enzyme, wherein said fusion polypeptide exhibits novel catalytic properties compared to either parent polypeptide from which it is derived. Such fusion polypeptides may be produced by conventional recombinant DNA techniques known to those skilled in the art, either by introducing a recombinant DNA capable of expressing the entire fusion polypeptide into said plant or alternatively, by a gene-targeting approach in which recombination at the DNA level occurs in vivo and the resultant gene is capable of expressing a recombinant fusion polypeptide.

Furthermore, the gene constructs of the invention which express an active LAR polypeptide of the RED protein superfamily may be introduced into non-legume companion species which serve as companion plants for bloat-inducing fodder and forage legumes such as lucerne (alfalfa) or white clover. In this embodiment, when the levels of condensed tannins in the companion species are sufficiently high, the bloat-safe companion species counters the action of the bloat-inducing forage-legume when both crops are ingested by a grazing animal. Preferred companion plants include, but are not limited to several species of *Lolium*, in particular *L. perenne*.

In a further embodiment, the rate of condensed tannin deposition may be reduced leading to a reduction in the total tannin content of plants by transferring one or more antisense, ribozyme, PTGS, or co-suppression molecules into a plant using a suitable gene construct as a delivery system.

The benefits to be derived from reducing tannin content in plants are especially apparent in fodder crops such as, but not limited to *Onobrychis viciifolia, Onithopus pinnatus, Ornithpus compressus, Coronilla varia, Lotus corniculatus, Lotus pedunculatus, Lotus purshianus, Lotus angustissimus, Lotus tenuis, Lespediza stipulacea, Desmodium intortum, Desmodium uncinatum, Leucaena leococephala, Macrotyloma axillare, Stylosanthes gracilis, Trifolium dubium, Hordeum vulgare, Vitis vinifera, Calliandra* spp, *Arachis* spp, *Brachiaria* spp., *Codariocalyx* spp, *Gliricidia* spp, *Eryth-* rina spp, *Flemingia* spp, *Phyllodium* spp., *Tadehagi* spp. or *Dioclea* spp., amongst others, where improved palatability or digestibility of said crop is desired. Benefits derived from this approach are also particularly apparent, for example, in particular tropical fodder and forage legumes such as, but not limited to Desmodium ovafolium.

Benefits are also to be derived in the brewing industry, from reducing the levels of condensed tannins present in barley crops. In particular, the presence of condensed tannins is undesirable in barley seed as it produces hazes in the brewed product, which is currently removed at great cost by filtration means.

The present invention is further described in the following non-limiting Examples. The examples herein are provided for the purposes of exemplification only and should not be taken as an intention to limit the subject invention.

EXAMPLE 1

Assay of Leucoanthocyanidin Reductase (LAR) Enzyme Activity

Leucoanthocyanidin reductase (LAR) was assayed using the following methods. Radioactivity labeled substrate had to be prepared and purified using radio-HPLC.

1. Substrates

[4-$^3$H]-2,3-trans-3,4-cis-leucocyanidin (cis-3,4-LC) was prepared by acid epimerization of the [4-$^3$H]-2,3-trans-3,4-trans-leucocyanidin (i.e. trans-3,4-LC) formed by reduction of (+)-dihydroquercetin [i.e. (+)-DHQ] with sodium [$^3$H]-borohydride, modified from the method of Kristiansen (1986). A solution containing 6.6 µmol (+)-DHQ in 250 µl of dry ethanol was added to 6.6 µmol of solid sodium [$^3$H]-borohydride (500 mCi) and incubated at 20° C. for 2 hr.

The 3,4-cis-leucocyanidin was obtained by epimerization of the 3,4-trans-leucocyanidin following addition of 5 ml of 0.1% (v/v) acetic acid and incubation for 3–4 hr at 40° C. The epimerization was monitored using HPLC system III (see below) and was halted by freezing in liquid nitrogen and lyophilization. The pale-yellow product was dissolved in 0.2 ml of methanol and the 3,4-cis-leucocyanidin purified by HPLC system I (see below), lyophilized and stored as a methanol solution at −80° C. The specific activity of the purified [$^3$H]-3,4-cis-leucocyanidin was generally approximately 5 µCi nmol$^{-1}$. Over 95% of the total radioactivity was recovered as a single peak using HPLC system III, corresponding to 3,4-cis-leucocyanidin.

Similarly, 3,4-cis-leucopelargonidin was prepared by reducing dihydrokaempferol to 2,3-trans-3,4-trans-leucopelargonidin with sodium [$^3$H]-borohydride followed by acid epimerization. The acid epimerisation of 3,4-trans-leucopelargonidin was followed with HPLC system IV. The 3,4-cis-leucopelargonidin was purified with HPLC system I. LAR converts 3,4-cis-leucopelargonidin to afzelechin.

Similarly, 3,4-cis-leucodelphinidin was prepared by reducing dihydromyricetin to 2,3-trans-3,4-trans-leucodelphinidin with sodium [$^3$H]-borohydride. The acid epimerisation of 3,4-trans-leucodelphinidin was followed with HPLC system III. The 3,4-cis-leucodelphinidin was purified with HPLC system 1. LAR converts 3,4-cis-leucodelphinidin to gallocatechin.

2. High Pressure Liquid Chromatography (HPLC).

HPLC was performed at 35° C. and the effluent UV absorbency monitored at 280 nm.

Six HPLC-systems were used for the separation of flavonoids and enzyme measurement:

I. Isocratic elution on µBondapak phenyl column, 30 cm×3.9 mm (Waters Assoc.), using water at a flow rate of 2 ml min$^{-1}$;

II. Isocratic elution on Goldpak C-18, 5 cm×0.45 cm (Activon), using 2% (v/v) acetic acid, at a flow rate of 2 ml/min;

IIa. Isocratic elution on NovaPak C-18, 15 cm×0.45 cm (Waters Assoc.), using 2% (v/v) acetic acid, at a flow rate of 1 ml/min; 3,4-cis-leucocyanidin and catechin eluted at 3.1 and 5.8 min respectively;

III. Gradient elution on Goldpak C-18, 5 cm×0.45 cm (Activon), developed with a linear gradient from 100% (v/v) solvent A (2% (v/v) acetic acid) to 70% solvent A: 30% solvent B (methanol) [(v/v)] at a flow rate of 2 ml/min over 5 min, and maintained at 30% (v/v) solvent B, at a flow rate of 2 ml/min, for 2 min;

IV. Gradient elution on Goldpak C-18, 5 cm×0.45 cm (Activon), developed with a linear gradient from 0% (v/v) methanol in water to 30% (v/v) methanol in water, at a flow rate of 2 ml/min over 5 min, and maintained at 30% (v/v) methanol in water, at a flow rate of 2 ml/min, for 2 mins; or V. Gradient elution on PRP-1 Polystyrene—Divinyl benzene, 15 cm×0.45 cm (Hamilton), developed with a linear gradient from 100% (v/v) solvent A (2% (v/v) acetic acid) to 70% solvent A: 30% solvent B (methanol) [(v/v)] at a flow rate of 2 ml/min over 5 min, and maintained at 30% (v/v) solvent B, at a flow rate of 2 ml/min, for 2 min. 3,4-cis-leucodelphinidin and gallocatechin eluted at 2.5 and 4.4 min respectively.

Elution volumes for compounds with these systems are provided in Table 2.

TABLE 2

Elution Volumes for substrates

| Compound | HPLC I | HPLC II VQLAR | HPLC III VQDFR | HPLC IV VQDFRW |
|---|---|---|---|---|
| 3,4-cis-leucodelphinidin | 4.1 | — | 0.58 min | 1.18 min |
| 3,4-trans-leucodelphinidin | 6.8 | — | 1.05 | 2.37 |
| gallocatechin | — | — | 1.10 | — |
| 3,4-cis-leucocyanidin | 11.6 min | 1.5 | 1.20 | 2.76 |
| 3,4-trans-leucocyanidin | 23.5 | 3.1 | 2.45 | 3.57 |
| 3,4-cis-leucopelargonidin | 3.9* | — | 2.46 | 3.78 |
| catechin | 31.0 | 3.5 | 2.50 | — |
| dihydromyretin | — | — | 3.07 | 4.18 |
| 3,4-trans-leucopelargonidin | 6.9* | — | 3.23 | 4.37 |
| afzelechin | — | — | 3.50 | 4.58 |
| dihydroquercetin | — | — | 4.64 | 5.53 |
| dihydrokaempferol | — | — | 5.70 | 6.45 |

*Replace water with 5% MeOH

The 3,4-cis-flavandiol isomers were quantified following complete conversion to their respective flavon-4-ols with excess purified LAR enzyme and NADPH. The UV absorbance peak area was compared to known amounts of authentic standards. Radio-labelled compounds were detected and quantified using a Beckman 171 Radio-HLPC detector with a 300 µl solid scintillation cell (3H efficiency 10%).

3. Assay of Enzyme Activities

LAR was assayed essentially as described by Tanner and Kristiansen (1993). The standard assay contained in total volume of 100 µl assay buffer containing 10 mg glycerol, 10 µmol NaPi, 0.5µmol NADPH, 0.1 µmol DDT, all adjusted to pH7 with NaOH, 0.25 nmol [$^3$H]-3,4-cis-leucocyanidin (1 µCi), or other suitable flavan-3,4-diol substrate (Table 2), and enzyme extract. The assay was initiated by the addition of an appropriate amount of enzyme extract and incubated at 30° C. for 30 min. The incubation was terminated by extraction with 0.2 ml ethyl acetate containing 10 nmol of unlabelled catechin as carrier. The ethyl acetate extracts were dried under a stream of nitrogen at room temperature. The residue was dissolved in 100 µl of water and analyzed by radio-HPLC using system II (see above and Table 2). In each radio-chromatogram of the assay mixtures derived from the leaf extracts referred to herein, only the substrate, 3-4-cis-leucocyanidin, or the product, catechin were detected.

Similarly the reduction of 3,4-cis-leucopelargonidin was assayed as above and terminated by extraction with ethyl acetate containing 10 nmol of cold carrier afzelechin, and analysed using HPLC system IV (see above and Table 2).

Similarly the reduction of 3,4-cis-leucodelphinidin was assayed as above and terminated by extraction with ethyl acetate containing 10 nmol of cold carrier gallocatechin, followed by two additional extractions with ethyl acetate alone, and analysed using HPLC system V (see above).

EXAMPLE 2

Purification of Desmodium Leucoanthocyanidin Reductase (LAR)

Purification of *D. uncinatum* LAR was achieved using the steps described below. Purification of duplicate 100 g preparations of leaf material was carried out to the hydroxylapatite column stage, and then fractions containing LAR activity were pooled and carried forward as a single extract until LAR was purified to homogeneity.

Young unexpanded leaves from 100 g *Desmodium uncinatum* (cv Silverleaf) were harvested and stored at −80° C. When required, the leaf samples were warmed for about 30 min to bring their temperature from −80° C. to −20° C., and homogenized, in two batches, in a total volume of 200 ml of grinding buffer [50 mM Pi, 10% (w/v) glycerol, 1% (w/v) PEG6000, 1 mM Na$_2$EDTA, 25 mM Na ascorbate, 5 mM DTT, 20 mM mercapto-ethanol, 2 µg/ml leupeptin, 1 µg/ml pepstatin, 1 µg/ml E64, 0.1 mM PMSF] all adjusted to pH 8 at room temperature with NaOH. The homogenate was filtered through Miracloth, and centrifuged at 12,000 rpm in a GSA rotor for 30 min.

The crude supernatant was adjusted to pH 8. Thirty grams of solid PEG 6000 were added per 100 ml of supernatant, and the mixture centrifuged at 12,000 rpm in a GSA rotor for 30 min. The 30% (w/v) PEG supernatant was adjusted to pH 5.8, with acetic acid, and centrifuged at 12,000 rpm in a GSA rotor for 30 min. The pellet was resuspended in 20 ml of dye column buffer 1 [10 mM NaPi, 0.1% (w/v) Tween, 20% (w/v) glycerol, 1 mM NaEDTA, 5 mM DTT, 2 µg/ml leupeptin, 1 µg/ml pepstatin, all adjusted to pH 7 with NaOH] to which was added 1% (w/v) PEG6000.

The enzyme was purified by chromatography on a series of columns containing reactive cellulose dyes bound to Sepharose (Ashton, A. R. and Polya, G. M., 1978). The media was prepared as follows: The Sepharose was washed extensively with water, and 100 ml of packed gel suspended in 100 ml of water containing 1M NaCl. 1 g of the respective dye was added, with 2 g Na$_2$CO$_3$ and the contents gently agitated overnight at 70° C. The gel was then washed sequentially with water, 8M urea and finally 8M urea, 1M NaCl to remove all unbound dye.

The resuspended protein preparation was applied to a column of Separose CL 4B-Procion Yellow H3R (17×2.5 cm) at a flow rate of 2.5 ml/min and the second unbound protein peak collected.

The collected protein fraction was then applied to a column of Sepharose S200-Bayer 4 (2.5×16.5 cm) at a flow rate of 2 ml/min. The column was washed extensively with column buffer 1 until the A$_{280}$ of the effluent returned to zero. Bound protein was eluted from the column by applying a 400 ml linear salt gradient to 1M NaCl in dye column buffer 1 (pH 7). Fractions of 10 ml were collected.

Fractions containing LAR activity that eluted from the Bayer 4 column were pooled and concentrated to a final volume of 5 ml, by applying nitrogen over a YM10 membrane (Amicon). The concentrated protein was desalted into 7 ml of dye column buffer 2 [10 mM Pi, 0.01% (w/v) Tween 20, 20% (w/v) glycerol, 5 mM DTT, 2 µg/ml leupeptin, 1 µg/ml pepstatin adjusted to pH 7 with NaOH], by passing it through a PD10 column (Pharmacia).

The desalted LAR protein solution was applied to a column (0.9×8.5 cm) of Sepharose CL4B-Cibacron Orange F-R (Ciba-Geigy), at a flow rate of 1 ml/min. The column was washed with at least 70 ml dye column buffer 2, until the A280 of the effluent returned to zero. Bound enzyme was eluted by applying a 10 ml solution of 5 µM NADPH in dye column buffer 2. Fractions of 1 ml volume were collected.

Fractions containing LAR activity were applied to a 5 ml column of hydroxylapatite (BioRAD EconPak CHTII) at 0.5 ml/min. Fractions of 1.5 ml in dye column buffer 2 were collected.

Fractions with LAR activity were combined from two experiments and diluted to 60 ml volume using buffer 3 [10 mM Pi, 1 mM DTT, 0.01% (w/v) Tween 20 adjusted to pH 7 with NaOH], and then concentrated to a final volume of 2.5 ml by applying nitrogen over a YM10 membrane (Amicon). The concentrate was desalted into 3.5 ml of MonoQ buffer A [25 mM triethanolamine, 20% (w/v) glycerol, 0.01% (w/v) Tween 20, 1 mM DTT adjusted to pH 7 with HCl] by passing it through a PD10 column (Pharmacia).

The desalted concentrate was applied to a 1 ml MonoQ HR5×5 column (Pharmacia) at a flow rate of 1 ml/min. The bound enzyme was eluted with a linear salt gradient from MonoQ buffer A to MonoQ buffer B [250 mM NaCl, 25 mM triethanolamine, 20% (w/v) glycerol, 0.01% (w/v) Tween 20, 1 mM DTT adjusted to pH7 with HCl], developed over 20 min. Fractions of 1 ml volume were collected. Peak activity was found in fractions 17 and 18.

The two fractions containing peak LAR enzyme activity were pooled and diluted to 10 ml with MonQ buffer A, and then re-applied to the MonoQ HR5×5 column (Pharmacia). Bound enzyme was eluted with a gradient from MonoQ buffer A to 60% MonoQ buffer B, developed over 30 min. Fractions of 0.5 ml volume were collected. The flow rate used was 1 ml/min. Peak activity was found in fractions 55 and 56.

The fractions containing peak LAR enzyme activity were pooled and concentrated to 0.2 ml using an Ultrafree concentrator (Millipore), at 6,000 rpm.

Data showing the purification of *D. uncinatum* LAR are presented in Table 3.

TABLE 3

Purification of *D. uncinatum* LAR

| Fraction | Total Activity (nmol/min) [% Yield] | Protein (mg) | Specific Activity (nmol/min/mg protein) [fold purification] |
|---|---|---|---|
| 1. Crude extract | 660 | 3,660 | 0.18 [1] |
| 30% (w/v) PEG Supernatant | 610 | 1,040 | 0.58 |
| 2. Resuspended pellet | 440 | 658 | 0.68 |
| 3. Procion Yellow H3R | 250 | 518 | 0.49 |
| 4. Bayer 4 | 270 | 13.8 | 19 |
| 5. Cibacron Orange F-R | 67 | ND | ND |
| Hydroxylapatite | 80 | ND | ND |
| 6. MonoQ (1) | 35 | ND | ND |

TABLE 3-continued

Purification of *D. uncinatum* LAR

| Fraction | Total Activity (nmol/min) [% Yield] | Protein (mg) | Specific Activity (nmol/min/mg protein) [fold purification] |
|---|---|---|---|
| 7. MonoQ (2) | 20 [3.0%] | 0.0023 | 8,700 [48,500] |

Figure 5:
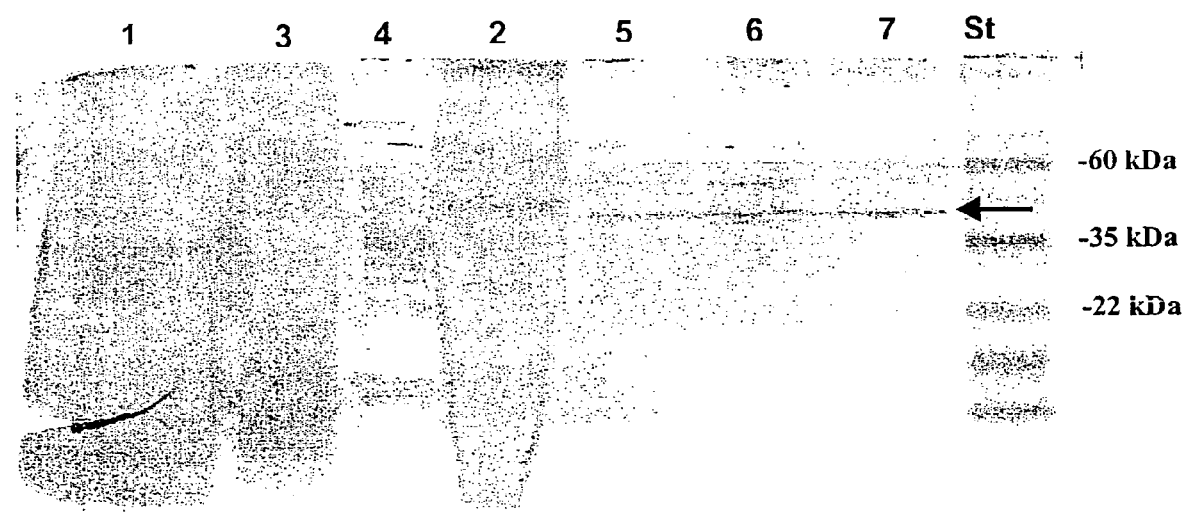
FIG. 5 is a copy of a photographic representation of a silver-stained SDS/polyacrylamide gel of the successive purification stages of LAR protein from *D. uncinatum*. Lanes numbers refer to the numbers given in column 1 of Table 3, showing successive stages of LAR purification. The lanes have been loaded with protein containing equal LAR activity. St—pre-stained molecular weight standard proteins (Gibco BRL); The arrow indicates the position of the 48 kDa LAR polypeptides consisting of at least two isoforms having different isoelectric points. The purification was obtained with the protocol given in Example 14.
Figure 6:
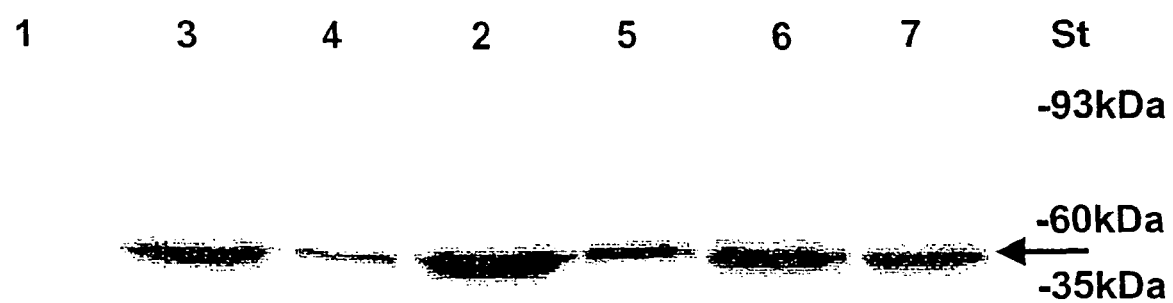
FIG. 6 is a copy of a photographic representation of a nitrocellulose membrane having a duplicate of the protein profile shown in FIG. 5 transferred thereon, and probed with purified antibodies to the C2 peptide as described in Example 11. The arrow indicates the position of the 48 kDa LAR polypeptides consisting of at least two isoforms having different isoelectric points.

ND, not determined
Numbers in column 1 correspond to lanes in the western blot in Example 11 (see FIGS. 4 and 5).

EXAMPLE 3

Amino Acid Sequence Analyses of Purified *Desmodium* LAR Peptide Fragments

1. Internal Amino Acid Sequences

Purified LAR protein was applied to a 12% (w/v) SDS/polyacrylamide gel that was subsequently stained with Coomassie G-250 (FIG. 1). Briefly 110 µl of the final protein concentrate was precipitated with 4 volumes of acetone at 70° C. for 30 min, cooled and centrifuged at 13,000 rpm in an Eppendorf centrifuge, and the pellet and dissolved in 20 µl of SDS buffer (Laemmli, 1970) and heated for 90 sec in a boiling water bath. The SDS protein solution was subjected to electrophoresis at 200V for 40 min as described by Laemmli (1970). The gel was stained with colloidal Coomassie Blue G250 (0.1% w/v) in 40% MeOH, 10% acetic acid for 30 min and washed extensively with MilliQ water overnight.

The amount of protein was determined by calibration against known 1 µg protein standards, comprising bovine serum albumin, ovalbumin, and soybean trypsin inhibitor proteins. Molecular weights were determined using a 10 kD protein ladder (GibcoBRL).

A dominant protein band in the LAR lane at 48 kD (FIG. 1) was excised for the determination of internal amino acid sequence. The protein band was excised, dried and digested with trypsin for 16 hr at 37 C and the resultant peptides extracted and purified with a C18 Zip-Tip (Millipore) and analyzed by ESI-TOF MS/MS using a Micromass Q-TOF MS equipped with a nanospray source. Data were acquired over the m/z range of 400–1800 Da to select peptides for MS/MS analysis. After peptides were selected, the MS was switched to MS/MS mode and data collected over the m/z range 50–2000 Da with variable collision energy settings.

The amino acid sequences of the following internal LAR peptides were thus obtained:

| | | |
|---|---|---|
| LAR_48_b | F[L/I]PSEFGHDVDR | (SEQ ID NO:16) |
| LAR_48b2_a | AYF[L/I]D | (SEQ ID NO:17) |
| LAR_48b2_d | EYE[L/I]DVV[L/I]S[L/I]VGGAR | (SEQ ID NO:18) |
| LAR_48_e | T[L/I]VVGGTGF[I/L]GQF[I/L]TK | (SEQ ID NO:19) |
| LAR_48_c | [L/I]GFGYPTF[L/I][L/I]VR | (SEQ ID NO:20) |
| LAR_48_a | [L/I] [L/I]DQ[L/I]T[L/I] [L/I]EA[L/I]K | (SEQ ID NO:21) |

2. N-terminal Amino Acid Sequence Determination

Figure 2:
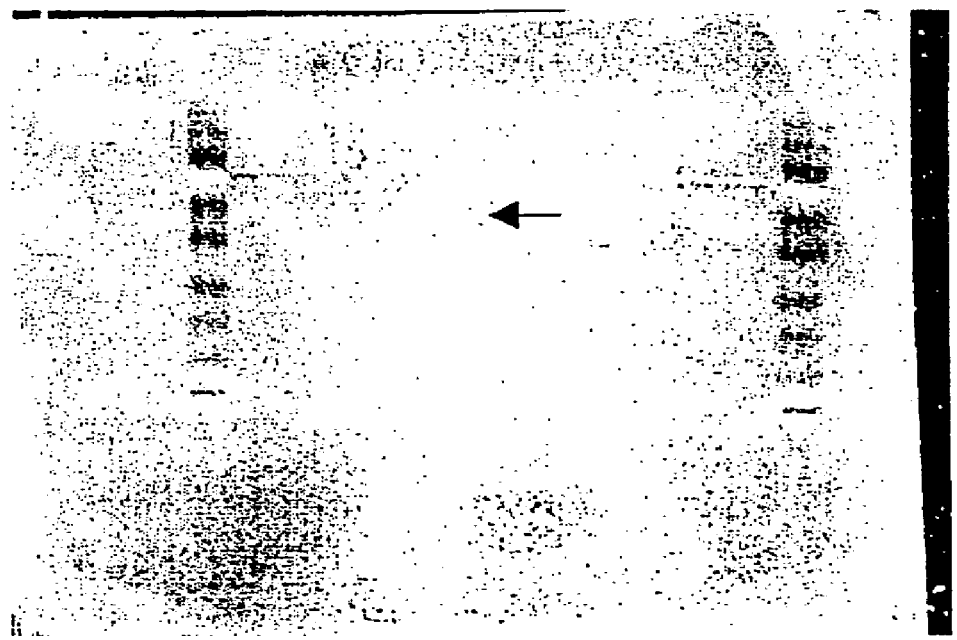
FIG. 2 is a copy of a photographic representation of a PVDF membrane having a duplicate of the protein profile of FIG. 1 transferred thereon, and stained with Ruby Blot (Bio-Rad). Lane 1, molecular weight standard proteins comprising a 10 kDa molecular weight ladder (Gibco BRL); Lanes 2 and 6, prestained protein standards (Gibco) added as a control for protein transfer; Lanes 3 and 5, 1 μg each of bovine serum albumin, ovalbumin, and soybean trypsin inhibitor proteins; and Lane 4, purified LAR protein. The arrow indicates the position of the 48 kDa LAR polypeptides that were excised from the membrane for N-terminal amino acid sequence determination.

Final enzyme concentrate (55 µl) was precipitated with 4 volumes acetone at −20° C. for 30 min, centrifuged at 13,000 rpm in an Eppendorf centrifuge. The pellet was retained, and dissolved in 20 µl SDS buffer (Laemmli, 1970). Resuspended protein was then heated for 90 sec in a boiling water bath. The SDS protein solution was subjected to electrophoresis as described supra, however the unstained gel was soaked for 5 min in CAPS buffer [10% (v/v) Methanol; 2.21 g/l CAPS/NaOH at pH 11]. The gel was blotted onto a Problot PVDF membrane (Applied Biosystems) in Bio-RAD wet blotter at 70 V for 70 min in CAPS buffer. The membrane was stained in Ruby Blot (Bio-Rad), and washed in MilliQ water (FIG. 2). The dominant 48 kDa LAR band (FIG. 2) was excised, and subjected to Edman degradation in an Applied Biosystems 494 Procise Protein Sequencing System.

One clear major N-terminal sequence of about 4 pmol was obtained:

Thr Val Ser Gly Ala Ile Pro Ser Met Thr Lys Asn Arg Thr Leu Val Val Gly Gly Thr Gly Phe Ile Gly Gln Phe Ile Thr (SEQ ID NO: 22).

There was evidence of microheterogeneity at positions 3, 13, 15, and 16 of the amino acid sequence obtained, suggesting the existence of at least two isoforms. In particular, there were minor occurrences of Glu at position 3, Gln at position 13, Val at position 15, and Gln at position 16 of the N-terminal sequence. Additionally, amino acid position 1 of the N-terminal sequence had minor occurrences of Gly, Ser, Asp, Arg, and Gln. This heterogeneity is reflected in the following N-terminal sequence (SEQ ID NO: 23):

```
Xaa Val Xaa Gly Ala Ile Pro Ser Met Thr Lys Asn Xaa Thr Xaa Xaa
1               5                   10                  15

Val Gly Gly Thr Gly Phe Ile Gly Gln Phe Ile Thr
            20                  25
``` wherein Xaa at position 1 is Thr, Gly, Ser, Asp, Arg or Gln; Xaa at position 3 is Ser or Glu; Xaa at position 13 is Gln or Arg; Xaa at position 15 is Leu or Val; and Xaa at position 16 is Val or Gln.

EXAMPLE 4

Two-dimensional Gel Electrophoresis of Purified *Desmodium* LAR

The purified LAR enzyme concentrate obtained in Example 2 (5 μl) was added to 195 μl of 8M urea, 2% (w/v) CHAPS, 0.5% (w/v) Resolyte pH 4-7 (BDH), 70 mM DTT, and 0.02% (w/v) bromophenol blue, and allowed to soak into an 11 cm pH 4-7 Dry-Strip (Pharmacia) containing an immobilized pH gradient. Isoelectric focussing was carried out by gradually increasing the voltage from 300V to 1,500 V over 6 hr and then at 1,500 V overnight. A second dimension was carried out on a 12–18% gradient SDS/polyacrylamide gel (Pharmacia), electrophoresed at a constant current of 20 mA for a total of 1,100 VHr. The gel was fixed and stained with silver according to manufacturers instructions (Pharmacia).

Figure 3:
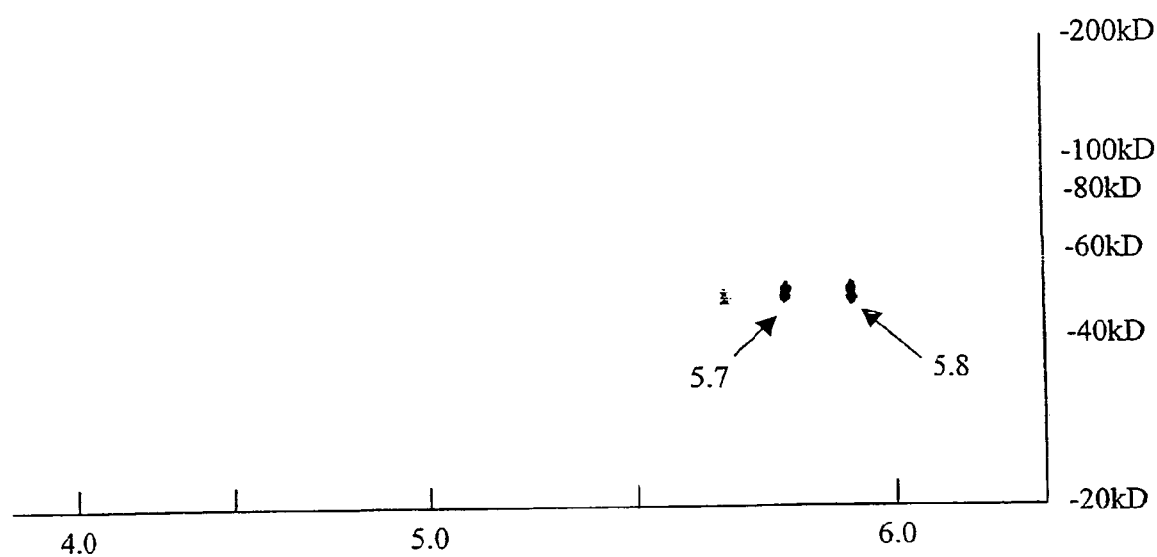
FIG. 3 is a copy of a photographic representation of a silver-stained two-dimensional gel of the purified LAR protein from *D. uncinatum*. The first dimension consisted of isoelectric focussing of purified LAR protein using Resolyte 4-7 (BDH). The second dimension consisted of SDS-PAGE. The pH gradient is indicated by the x-axis. The ordinate shows molecular weight (kDa) of the proteins. Arrows indicate the positions of at least two dominant isoforms of the LAR protein, having pi values of about 5.7 and about 5.8, and a molecular weight of about 48 kDa as estimated by SDS/PAGE.

Two dominant spots, having pi values of about 5.7 and 5.8, and an estimated molecular weight of 48 kDa (FIG. 3). These protein spots may be two isoforms of LAR, as suggested by the N terminal sequence data supra.

EXAMPLE 5

Amplification of LAR Gene Fragments

Blast analysis of peptides LAR 48A, LAR 48C and LAR 48E indicated that they were all related to the RED protein superfamily and predicted to be arranged in the order: N-terminus, LAR 48E, LAR 48C and LAR 48A, C-terminus.

Two pools of degenerate oligonucleotide primers were designed, based upon the amino acid sequences of the peptides LAR 48C and LAR 48A derived from the isolated *D. uncinatum* LAR enzyme. The pools of degenerate oligonucleotides were synthesized on a Applied Biosystems oligonucleotide synthesizer.

The nucleotide sequences of the primers are shown below:

Forward primer (oligo 20° C.): based on peptide: LAR 48C
5'-GGITT(C/T)GGITA(C/T)CCIACITT(T/C)-3' (SEQ ID NO: 24); and Reverse primer (Oligo A$_{rev}$30 mer): based on peptide LAR 48A
5'-(T/C)TTIAIIGC(C/T)TCIAIIAIIGTIAI(T/C)TG(G/A)TCA-3' (SEQ ID NO: 25).

cDNA was prepared from young leaves of *Desmodium uncinatum* (cv Silverleaf). A 230 bp product was amplified using 40 pmol of each primer, 20 pmol of dNTPs, 50 ng cDNA, 1.5 unit Taq polymerase (Boehringer-Mannheim), in a 20 μl PCR reaction containing standard Taq buffer, according to manufacturer's instructions. The specified cycling parameters used were:

(i) a hot start at 94° C.;
(ii) an initial cycle comprising an incubation at 94° C. for 2 min., followed by 41° C. for 10 sec, followed by 72° C. for 25 seconds;
(iii) 35 cycles each comprising 94° C. for 10 sec., followed by 41° C. for 10 sec., followed by 72° C. for 25 sec.; and
(iv) one cycle comprising 94° C. for 10 sec., followed by 41° C. for 10 sec., followed by 72° C. for 5 min.

The amplified DNA product was analyzed on a 1% (w/v) agarose gel, excised, and cloned into a pGEMT vector system (Promega). The nucleotide sequence of the amplified DNA (SEQ ID NO: 26) is set out below. Analysis of the six possible reading frames of SEQ ID NO: 26 reveals that only one reading frame encoded an amino acid sequence having homology to the isolated *D. uncinatum* LAR polypeptide. This predicted sequence contained peptide sequence LAR_48b2_d (SEQ ID NO:18). The derived LAR sequence encoded by the amplified DNA (SEQ ID NO: 27) is shown.

```
ggg ttc ggt tat ccg acg ttt ttg ctc gta agg cca gga cct gtc tca    48
Gly Phe Gly Tyr Pro Thr Phe Leu Leu Val Arg Pro Gly Pro Val Ser
1               5                   10                  15 cct tcc aag gct gtc att atc aaa acc ttt caa gac aaa ggt gct aag    96
Pro Ser Lys Ala Val Ile Ile Lys Thr Phe Gln Asp Lys Gly Ala Lys
                20                  25                  30 gtt atc tat ggc gta att aat gac aag gaa tgc atg gag aag att ttg   144
Val Ile Tyr Gly Val Ile Asn Asp Lys Glu Cys Met Glu Lys Ile Leu
            35                  40                  45 aag gag tac gag att gat gtc gtc att tct ctt gta gga ggc gca cga   192
Lys Glu Tyr Glu Ile Asp Val Val Ile Ser Leu Val Gly Gly Ala Arg
        50                  55                  60 cta ttg gac cag ctc acc ctc ctc gag gcc ctc aaa                    228
```

```
                                    -continued
Leu Leu Asp Gln Leu Thr Leu Leu Glu Ala Leu Lys
 65                  70                  75
```

EXAMPLE 6

Cloning a Full-length cDNA Encoding *D. uncinatum* LAR

A cDNA library was prepared using mRNA derived from young leaves of *Desmodium uncinatum* (cv Silverleaf), and screened using the amplified DNA fragment (SEQ ID NO: 27) as a hybridization probe under standard conditions.

Briefly, *D. uncinatum* mRNA was purified from total RNA derived from newly emerged leaves using a Promega PolyATract system essentially according to the manufacturer's instructions. First strand cDNA employed oligonucleotide d(T) primers. Second-strand synthesis was achieved using art-recognized procedures. The cDNA was directionally inserted between the EcoRI and XhoI sites of the bacteriophage vector λ Uni-ZAP XR (Stratagene, USA) according to the supplier's instructions. Approximately $3 \times 10^6$ bacteriophage were plated and screened. Ten positive clones were plaque-purified.

The nucleotide sequence of the hybridized cDNA clone was determined, (SEQ ID NO: 28) and is set out below. The derived LAR sequence encoded by the isolated cDNA (SEQ ID NO: 29) is shown. This protein has a predicted pI of 5.94, and a predicted molecular mass of 42665. The other clones were essentially identical but differed in length at the 5' and 3' ends.

```
gcctcaactc actttgtgt gatacgctcc aagcaaaagc tagctaagaa caagaaaata   60
tacatagaaa agcaagatcc gaggttgttg gaaaaaataa attgagaaag aagaagaaaa  120 t atg acg gta tcg ggt gca att cct tca atg acc aag aac cga act ttg  169
  Met Thr Val Ser Gly Ala Ile Pro Ser Met Thr Lys Asn Arg Thr Leu
   1               5                  10                  15 gtg gtc gga gga act ggg ttc ata ggt cag ttc ata act aag gca agt    217
Val Val Gly Gly Thr Gly Phe Ile Gly Gln Phe Ile Thr Lys Ala Ser
             20                  25                  30 ctt ggc ttt ggg tac cct acc ttt ttg ctc gta agg cca gga cct gtc    265
Leu Gly Phe Gly Tyr Pro Thr Phe Leu Leu Val Arg Pro Gly Pro Val
         35                  40                  45 tca cct tcc aag gct gtc att atc aaa acc ttt caa gac aaa ggt gct    313
Ser Pro Ser Lys Ala Val Ile Ile Lys Thr Phe Gln Asp Lys Gly Ala
     50                  55                  60 aag gtt atc tat ggt gta att aat gac aag gaa tgc atg gag aag att    361
Lys Val Ile Tyr Gly Val Ile Asn Asp Lys Glu Cys Met Glu Lys Ile
 65                  70                  75                  80 ttg aag gag tac gag att gat gtc gtc att tct ctt gta gga ggc gca    409
Leu Lys Glu Tyr Glu Ile Asp Val Val Ile Ser Leu Val Gly Gly Ala
                 85                  90                  95 cga cta ttg gat cag ctt acc ttg ttg gag gcc ata aaa tct gtg aag    457
Arg Leu Leu Asp Gln Leu Thr Leu Leu Glu Ala Ile Lys Ser Val Lys
            100                 105                 110 act atc aag agg ttt ctg cct tca gag ttt ggg cac gat gtg gat agg    505
Thr Ile Lys Arg Phe Leu Pro Ser Glu Phe Gly His Asp Val Asp Arg
        115                 120                 125 aca gat cct gta gag cca gga ttg aca atg tac aaa gag aag cgt ttg    553
Thr Asp Pro Val Glu Pro Gly Leu Thr Met Tyr Lys Glu Lys Arg Leu
    130                 135                 140 gtt agg cgt gct gtt gag gaa tat ggg att cct ttc acc aac att tgc    601
Val Arg Arg Ala Val Glu Glu Tyr Gly Ile Pro Phe Thr Asn Ile Cys
145                 150                 155                 160 tgc aac tcc att gct tct tgg cct tat tat gac aat tgt cac cct tcc    649
Cys Asn Ser Ile Ala Ser Trp Pro Tyr Tyr Asp Asn Cys His Pro Ser
                165                 170                 175 cag gtc cct cca ccc atg gat cag ttt caa atc tat ggt gat ggc aac    697
Gln Val Pro Pro Pro Met Asp Gln Phe Gln Ile Tyr Gly Asp Gly Asn
            180                 185                 190 acc aaa gct tac ttc att gat ggc aat gat att gga aag ttc aca atg    745
Thr Lys Ala Tyr Phe Ile Asp Gly Asn Asp Ile Gly Lys Phe Thr Met
        195                 200                 205
```

```
aag acc att gat gat atc aga aca ctg aac aaa aat gtt cat ttt cga    793
Lys Thr Ile Asp Asp Ile Arg Thr Leu Asn Lys Asn Val His Phe Arg
    210                 215                 220 ccc tcg agc aac tgt tat tcc atc aat gaa ctt gct tct tta tgg gaa    823
Pro Ser Ser Asn Cys Tyr Ser Ile Asn Glu Leu Ala Ser Leu Trp Glu
225                 230                 235                 240 aag aaa att gga cgt aca ctt ccc aga ttc acc gta aca gcg gat aaa    889
Lys Lys Ile Gly Arg Thr Leu Pro Arg Phe Thr Val Thr Ala Asp Lys
                245                 250                 255 ctt ctt gct cat gct gca gaa aat att ata cca gaa agt att gta tca    937
Leu Leu Ala His Ala Ala Glu Asn Ile Ile Pro Glu Ser Ile Val Ser
            260                 265                 270 tcg ttc acc cat gat att ttc atc aac ggt tgc caa gtt aac ttc agc    985
Ser Phe Thr His Asp Ile Phe Ile Asn Gly Cys Gln Val Asn Phe Ser
        275                 280                 285 ata gat gaa cat agt gat gtt gag att gac aca ctc tat cca gat gaa   1033
Ile Asp Glu His Ser Asp Val Glu Ile Asp Thr Leu Tyr Pro Asp Glu
    290                 295                 300 aaa ttt cga tcc ttg gac gat tgc tat gag gac ttt gtt ccc atg gtc   1081
Lys Phe Arg Ser Leu Asp Asp Cys Tyr Glu Asp Phe Val Pro Met Val
305                 310                 315                 320 cat gac aag att cat gca gga aaa agt gga gaa att aaa att aaa gat   1129
His Asp Lys Ile His Ala Gly Lys Ser Gly Glu Ile Lys Ile Lys Asp
                325                 330                 335 gga aag ccc ttg gta cag acc gga aca att gaa gaa att aat aag gac   1177
Gly Lys Pro Leu Val Gln Thr Gly Thr Ile Glu Glu Ile Asn Lys Asp
            340                 345                 350 ata aag act ttg gta gag aca caa cca aat gaa gaa att aaa aag gat   1225
Ile Lys Thr Leu Val Glu Thr Gln Pro Asn Glu Glu Ile Lys Lys Asp
        355                 360                 365 atg aag gct ttg gta gag gca gtg cca att tca gct atg ggc           1267
Met Lys Ala Leu Val Glu Ala Val Pro Ile Ser Ala Met Gly
    370                 375                 380
```

EXAMPLE 7

LAR is a Member of the RED Protein Superfamily

A simple Blast search of the Swissprot database with the N-terminal amino acid sequence of LAR suggests closest homology of LAR to an *Arabidopsis thaliana* P3 isoflavone reductase protein, which is a member of the Reductase-Epimerase-Dehydrogenase (RED) protein superfamily. The RED protein superfamily includes various isoflavone reductases (IFR), phenylcoumaran benzylic ether reductases, and pinoresinol-lariciresinol reductases.

A multiple sequence alignment using DIAGLIN 2.1 (Burkhard Morgenstein, 1999) confirms the classification of the *D. uncinatum* LAR protein in the RED superfamily with other members of the RED superfamily (FIG. 4).

EXAMPLE 8

Transformation of White Clover with LAR Gene Sequences

1. Seed

Transformation experiments are carried out with the white clover cultivars Haifa, Kopu, Irrigation, and Waverley. The transgenic plants used in the study with the auxin-responsive promoter:GUS fusion are all in cv. Haifa.

2. Vector Plasmids and Agrobacterium Strains

The binary transformation plasmid pBS288, which contains a unique EcoRI restriction site for the insertion of LAR genetic sequences, between the SCSV Sc4 promoter and Sc5 terminator sequences, in addition to the selectable marker expression cassette ScI-nptII-Sc3, between *Agrobacterium* left and right border sequences, is used in transformation experiments to modify proanthocyanidin levels in plants.

Alternatively, the binary transformation plasmid pJJ430 may be used. Plasmid pJJ430 contains the 749 bp EcoRI-NcoI promoter and 5' untranslated sequence of the soybean GH3 gene (Hagen et al., 1991) translationally coupled to the GUS coding sequence (Jefferson et al., 1987) and the pea vicilin 3' sequence. This plasmid was constructed as follows. The NcoI site of pQ20 (a gift from Dr Diana Quiggin, CSIRO Division of Plant Industry, Canberra, Australia) containing the GUS initiator methionine, was used to fuse the GH3 gene promoter to the GUS reporter gene sequence. A 2.85 kb EcoRI fragment containing the GH3 promoter GUS fusion and the 3' vicilin sequence was cloned from the pQ20 derivative into the EcoRI site of pTAB10 (Khan et al., 1994; Tabe et al., 1995) to generate pJJ430. This vector also contains the bar selectable marker gene from *Streptomyces hygroscopicus* encoding phosphinothricin acetyl transferase (De Block et al., 1987; Jones et al., 1992), placed operably under the control of the CaMV 35S promoter sequence (Pietrzak et al., 1986) and connected to the octopine synthase (ocs) terminator sequence (Jones et al., 1992). When expressed, the bar gene confers resistance to phosphinothricin (PPT) or the commercial herbicide preparations bialophos or Basta.

Vectors which facilitate the use of kanamycin as a selection agent are identical to those described in all other essential respects, however they comprise the nptII gene flanked by the nos promoter and nos 3' sequences (described by An et al., 1985) or alternatively, in the case of the pBS288 expression vector employ the sub-clover stunt virus Sc1 promoter and Sc3 terminator sequences to express the nptII gene in plants.

A vector which facilitates the use spectinomycin as a selection agent carries the aadA gene flanked by the CaMV 35S promoter and ocs3' from SLJ6B1 (Jones etal., 1992).

All binary plasmids are introduced into plant tissues using the supervirulent *Agrobacterium tumefaciens* strain AGL1 which carries a disarmed Ti plasmid (Lazo et al., 1991).

3. White Clover Transformation

White clover seed are surface sterilized by soaking in 70% (v/v) ethanol for 3 min, 30% (v/v) bleach solution (final 1:5% (w/v) available chlorine) for 40 min, 70% ethanol again for 3 min followed by 6 washes in sterile distilled water over 1 h. These seeds are allowed to imbibe overnight in the dark at 15° C. for 17 hr. The seeds are dissected under a binocular microscope to separate the imbibed cotyledons. Cotyledons are cut from the hypocotyl and epicotyl such that a small portion of the stalk was included, but not the cotyledonary node joining it to the hypocotyl. The cotyledons are collected into MG broth (Garfinkle, 1980) in a Petri dish.

The *Agrobacterium tumefaciens* culture is grown at 27° C. for 20–24 hr in MG broth, to a cell density of about $3-5 \times 10^9$ cells per ml. The cotyledons are transferred to the *Agrobacterium* suspension in a shallow layer and gently agitated for 40 min. Following this incubation, the cotyledons are transferred onto sterile filter paper to absorb excess suspension. The cotyledons and adhering bacteria are co-cultivated at 24° C. in the light for 3 days on agar medium B5PB. This medium contains the basal salts, vitamins and sugars of B5 (Gamborg et al., 1968) with 12 nM picloram, 2.2 µM BAP and 0.7 (w/v) % agar.

After 3 days, the cotyledons are collected, washed several times with sterile water, blotted with filter paper and transferred to B5PB containing 300 µg/ml Timentin (Beecham Res. Labs.; a 30:1 (w/w) mixture of sodium ticarcillin and potassium clavulanate) and 5 µg/ml of PPT. After 3 weeks, cotyledons with green shoot initials are transferred to B5PB medium containing Timentin and PPT and cultured for a further 3 weeks. Green shoots are then transferred to the RIB medium. RIB medium contains the basal salts and organics of L2 (Phillips and Collins, 1984) plus 1.2 µM IBA. If the shoots are already large, the RIB medium lacks PPT, but if the shoots are still small the RIB medium contains 5 µg/ml PPT to safeguard against non-transgenic escape.

Although there are often multiple shoots, only one green plantlet is chosen from each cotyledon to ensure all regenerants are from independent transformation events. After forming roots within 2 or 3 weeks, plantlets are transferred to soil, but only after confirmation of their transformed status. In most cases this initial confirmation is by assay for the relevant resistance gene expression or alternatively, by determining the presence of the resistance gene in plantlets.

4. Results

The cotyledons at the time of dissection are 0.5–1 mm long. Following the 3 day cocultivation with Agrobacterium the cotyledons have swollen to 3–5 times their initial volume. Following the first 3 weeks selection, the cotyledons are about 10 times their initial volume and green initials are emerging from the cut end. PPT selection is stringent, turning the cotyledons yellow or brown, and suppressing any substantial growth from untransformed tissues. In the case of spectinomycin, the selection does not result in a noticeable suppression of growth, but all the untransformed growth is bleached white allowing easy recognition of the green transformed shoots.

Transgenic plants can be transferred to soil within 9 weeks of the Agrobacterium co-cultivation. If a third period of selection is employed, which is advisable when using kanamycin selection, the total length of time to soil is about 12 weeks.

EXAMPLE 9

Inhibition of Condensed Tannin Production in Transgenic *Lotus corniculatus* Plants One example of transgenic plants in which condensed tannin production is inhibited is provided by the expression of an antisense LAR gene construct therein. Antisense technology can be used to target expression of an endogenous proanthocyanidin gene(s), such as the LAR gene, to reduce the amount of condensed tannin produced by plants which, in the absence of any human intervention, produce high levels of condensed tannins in their leaves.

In the present example, the antisense gene constructs containing fragments of the LAR cDNA clone set forth in SEQ ID No: 28, cloned, in the antisense orientation, into the unique EcoRI site of pBS288, are introduced into *L. corniculatus* as described in the preceding example.

Genetically-transformed *Lotus corniculatus* plants are produced which produce much lower levels of condensed tannins in their leaves than isogenic, non-transformed lines.

For the present purpose, the antisense LAR gene is expressed under control of the ScSV Sc4 promoter, however other promoters, such as the CaMV 35S promoter sequence may also be used.

Wherein the pBS288 vector is employed, transgenic plants which are resistant to kanamycin are selected for further analysis.

In one approach, transgenic plants are analyzed by northern blot hybridization for expression of the antisense LAR gene or fragment thereof using a radioactively-labeled "sense" riboprobe to avoid detection of endogenous LAR mRNAs.

The level of LAR enzyme activity in the leaves of transgenic plants expressing the antisense LAR gene is measured by the assay described in Example 1. A range of expression levels is detected, with reductions in the level of LAR ranging from 10% to 95%, preferably 30% to 95%, more preferably 50% to 95% and even more preferably 70% to 95%, including 95% to 99% or 100%, compared to isogenic, non-transformed control lines.

The level of condensed tannins is also measured in lines which express the antisense gene construct, essentially according to Terrill et al (1992a) and Li et al (1996). The condensed tannin content of transformed plants is reduced by at least 10%, preferably by at least 30% and more preferably by at least 50%, compared to isogenic, non-transformed control plants.

The phenotype of the transgenic plants thus produced varies considerably, depending upon the level of inhibition of expression of the endogenous LAR gene. Results indicate that it is possible to manipulate the levels of condensed tannins in the leaves of plants using antisense constructs which target expression of the LAR gene.

EXAMPLE 10

Expression of D. uncinatum LAR in Transgenic Trifolium repens Plants

Two strategies are employed to express LAR in *Trifolium repens* plants.

In the first strategy, the ScSV Sc4 promoter sequence is operably connected to a full-length *D. uncinatum* LAR cDNA. This is achievable by cloning the full-length cDNA in the sense orientation between the ScSV Sc4 promoter and the ScSV Sc5 terminator sequences of plasmid pBS288.

In the second strategy, a genomic LAR gene, either with its own promoter and terminator sequences or with promoter and terminator sequences derived from other genes, is cloned into a binary plasmid vector such as pBS288.

For *Agrobacterium*-mediated tissue transformation, binary plasmid constructs discussed supra are transformed into *Agrobacterium tumefaciens* strain AGL1 or other suitable strain.

The recombinant DNA constructs are then introduced into a transformation receptor plant, essentially as described in Example 8.

A suitable receptor plant, for example, is *Trifolium repens*, in particular a green-leafed variety or a mutant of same which has red leaves. Red-leafed white clover plants produce ample anthocyanin and leucoanthocyanidin but do not produce catechin. The red-leafed plant therefore has an ample supply of substrates which can be diverted into catechin or condensed tannin biosynthesis via the provision of an additional LAR gene.

Alternatively, the transformation receptor plant may be lucerne, a tropical legume or other fodder or forage legume.

The transgenic plants thus produced exhibit a range of phenotypes, partly because of position effects, transgene copy number and variable levels of expression of the LAR transgene.

In particular, transgenic, red-leafed white clover expressing the LAR gene produce significantly more catechin than non-transgenic white clover plants.

LAR enzyme activity in the transgenic plants and isogenic untransformed control plants is determined as described in Example 1. In general, the level of condensed tannin deposition and rates of condensed tannin biosynthesis in the transgenic plants are significantly greater than for untransformed control plants.

Transgenic plants are also analyzed by northern blot hybridization for expression of the sense LAR gene using a radioactively-labeled "antisense" riboprobe to detect LAR mRNAs. The steady-state level of LAR mRNA in transformed lines is at least 2-fold that observed in isogenic non-transformed controls, at the $p<0.01$ significance level. In some transgenic lines, however, the level of LAR gene expression is at least 5- to 10-fold the level observed in non-transformed plants.

Levels of condensed tannins in transformed plants are also significantly higher than in control plants, indicating that it is possible to genetically manipulate the level of condensed tannins in plants by increasing expression of LAR.

EXAMPLE 11

Production of Antibodies to LAR

Antibodies were prepared which were capable of binding to LAR, using immunogenic fragments of the purified LAR enzyme (Example 2) or a recombinant LAR protein or recombinant LAR fusion protein as an antigen.

In one example, antibodies are against synthetic peptides, referred to as C1 and C2, comprising the sequence of amino acids corresponding to SEQ ID NOs: 30 or 31, respectively. Eight copies of the peptide were coupled through a terminal cysteine to a reactive chloro-acetylated octavalent lysine core to produce a multi-antigenic peptide (MAPS, Tam 1994).

```
C1 peptide:  HDKIHAGKSGEIKIKDGK    (SEQ ID NO:30)

C2 peptide:  NKDIKTLVETQPNEEIKKDMK (SEQ ID NO:31)
```

The MAPS were used to immunize 3 months-old New Zealand White rabbits.

Pre-immune sera were collected prior to the primary immunization. The rabbits were given boost immunizations at various intervals within the following 10 weeks. Sera were collected and the IgG fractions purified by Protein G columns as described the manufacturer's instructions (Pharmacia, Uppsala).

Figure 11:
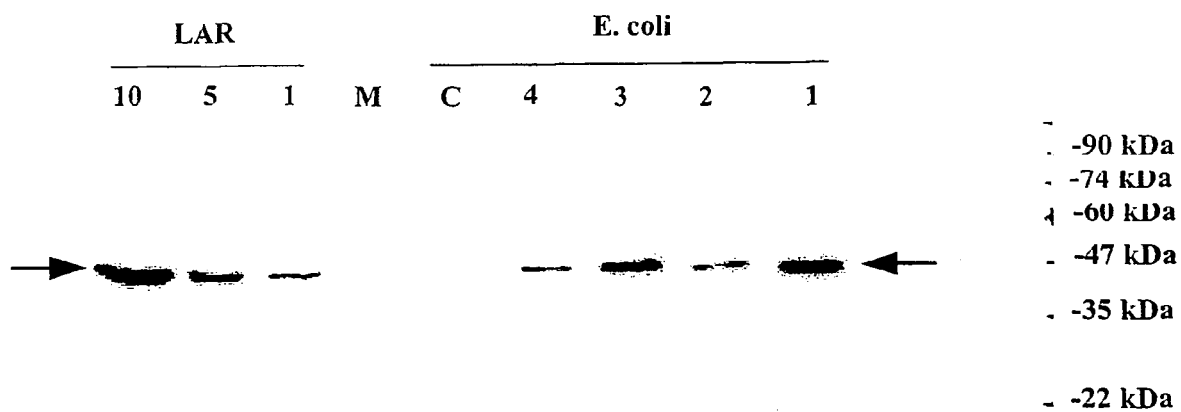
FIG. 11 is a copy of a photographic representation of a nitrocellulose membrane after Western blot analysis as described in Example 11. Proteins were extracted from the indicated plant or bacterial extracts; LAR—either 10, 5, or 1 ul of crude *Desmodium* extract, isolated as in Example 2; M—Gibco prestained molecular weight markers; *E. coli*—extracts of *E. coli* following induction as described in Example 12, C=bacterial control lacking the pET vector or independent bacterial clones 4, 3, 2, 1 carrying the pET LAR382 construct. The blot was probed with purified antibodies to the C2 peptide as described in Example 11. The arrows indicate the position of the 48 kDa LAR polypeptides present in both plant and bacterial extract.

Pre-immune antibodies and immune antibodies were tested for immunoreactivity to *D. uncinatum* LAR enzyme in leaf cell extracts or LAR fusion proteins by Western Blot analysis. The LAR proteins were separated on a 10% (w/v) SDS/polyacrylamide gel and transferred to PVDF membranes. The blots were probed with the purified antibodies followed by horseradish peroxidase linked goat anti-rabbit antibodies (Amersham, England). Blots were developed using a chemiluminescence substrate as described by the manufacturer's instructions (DuPont NEN). Immune antibodies raised against LAR recognise both the endogenous and the bacterially-expressed LAR proteins (see FIG. 11).

Furthermore, western blots indicate that immune sera, but not pre-immune sera are capable of binding at high titer to a synthetic peptide comprising the amino acid sequence set forth in SEQ ID No: 30 or 31. Moreover, the immune sera are also capable of immunoprecipitating LAR enzyme activity from plant cell extracts.

EXAMPLE 12

Expression of LAR in E. coli and Purification of Recombinant LAR Protein

1. Construction of LAR Expression Vectors

The *D. uncinatum* cDNA encoding the LAR protein (SEQ ID NO: 29) was used to recombinantly-express LAR, using the bacterial expression constructs pET3a (Novagen) and pQE30 (Qiagen).

The complete amino acid coding sequence of the LAR cDNA was introduced into the BamHI site of the pET3a expression vector to express the LAR382 polypeptide containing the 14 amino acid N-terminal T7 Tag. The resultant expression construct was then introduced into *E. coli* strain Rosetta(DE3) RARE/pLysS. Induction of gene expression resulted in high-level expression of a fusion protein comprising T7-Tag and LAR polypeptides.

A truncated form of LAR comprising amino acids 1–317 was also introduced into the BamHI and HindIII sites of pQE30 expression vector to express the LAR317 polypeptide containing the 10 amino acid N-terminal RGS-6×His epitope. The resultant expression construct was then introduced into E. coli strain XL1 Blue.

Induction of gene expression resulted in high level expression of a fusion protein comprising the RGS-6×His epitope tag and the truncated LAR317 polypeptide.

2. Expression and Affinity Purification of Recombinant LAR Fusion Polypeptides

Expression of LAR under control of the T5 promoter in the pQE30 vector is carried out as recommended by the supplier (Qiagen). Bacteria with the clone produce a protein, after 120 min induction with IPTG (isopropyl β-D-thiogalactopyranoside).

To express LAR under the control of the T5 promoter in pQE-LAR, bacterial colonies transformed with PQE-LAR are selected and cultured overnight at 37° C. in 3 ml LB growth medium [1% (w/v) tryptone, 0.5% (w/v) yeast extract, 1% (w/v) NaCl] supplemented with ampicillin (100 μg/ml) and kanamycin (25 μg/ml). Flasks containing 1 L of LB growth medium and ampicillin (50 μg/ml), either with or without glucose, and a 1:50 inoculum of overnight cultures are shaken at 37° C. After 30 mins, the P5 promoter of the expression construct pQE-30-LAR is induced using IPTG at a final concentration of 2 mM and cultures are incubated for a further for 3–5 hours. Cells are harvested by centrifugation.

To purify the recombinant LAR-polyHis fusion protein, 2 ml of a 50% slurry of Ni-NTA resin (Qiagen) are first equilibrated with PBS. The bacterial cells expressing the polyhistidine-LAR fusion protein are recovered by centrifugation at 4000 g for 10 min and the pellet sonicated in 2.5% (v/v) Zwittergent (Sigma, product No T7763). The sonicate is mixed with the Ni-NTA slurry for 30 min. Unbound proteins are removed from the supernatant fraction following centrifugation at 800 g. Recombinant LAR is eluted from the Ni-NTA slurry with 1 bed volume of 50 mM imidazole. Multiple eluates are collected to maximize yield.

3. Protein Assays

Protein concentrations are estimated by the Bradford dye assay (Biorad) using bovine gamma globulin as standard.

EXAMPLE 13

Enzyme Activity of Recombinant LAR Protein

Figure 12:
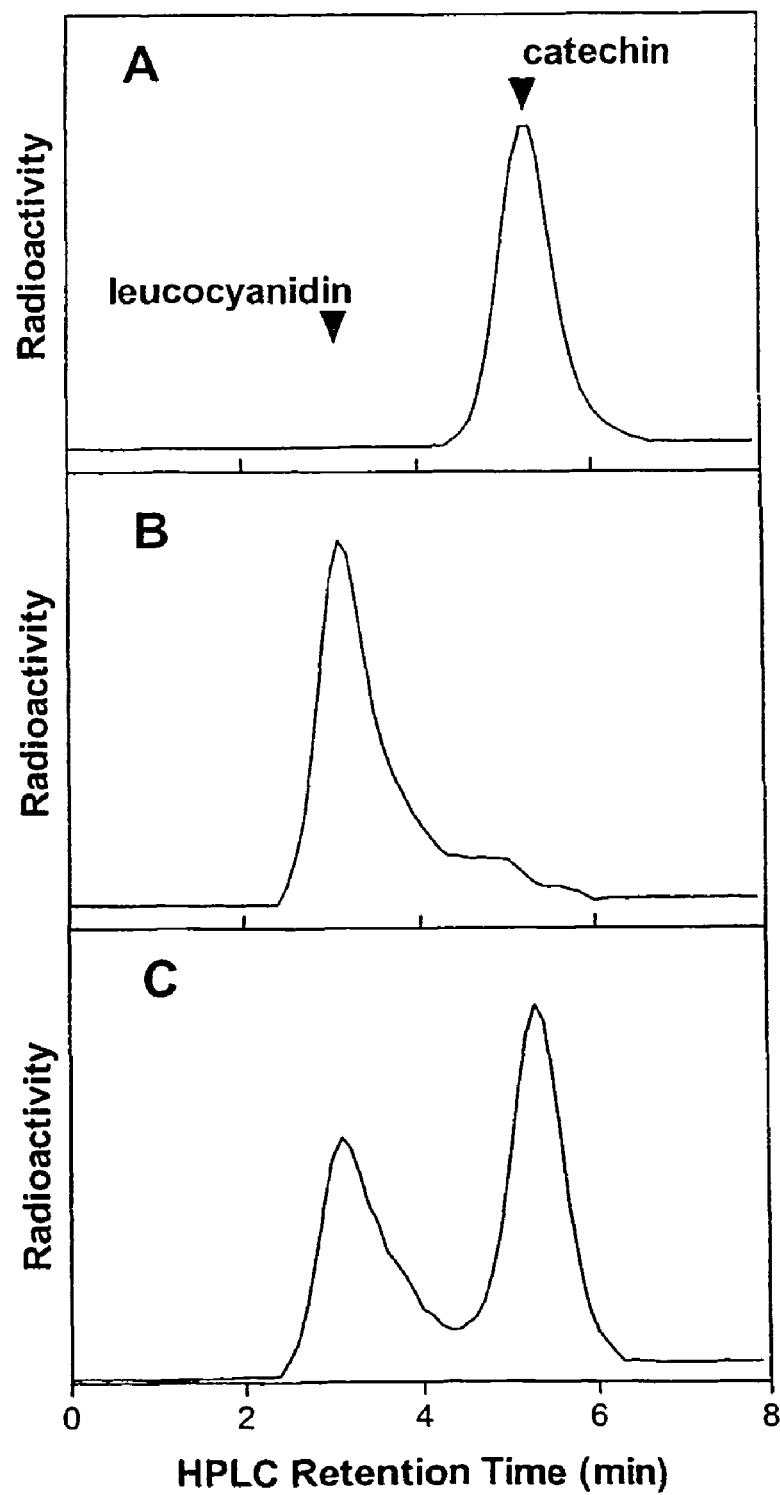
FIG. 12 is a copy of three radio-HPLC chromatograms which show the induction of LAR activity in *E. coli* transformed with the full length expression construct as described in Example 13. Extracts of *E. coli*, transformed with pET LAR382 have produced LAR activity sufficient to convert all of the leucocyanidin substrate into catechin (panel A) when assayed as in Example 1 using HPLC system IIa. Extracts of control bacteria did not have any LAR activity (panel B). The catechin produced by pET LAR382 co-migrated with radio-catechin produced from authentic LAR enzyme purified from *Desmodium* (panel C). Radio-catechin co-eluted with authentic catechin.
Figure 13:
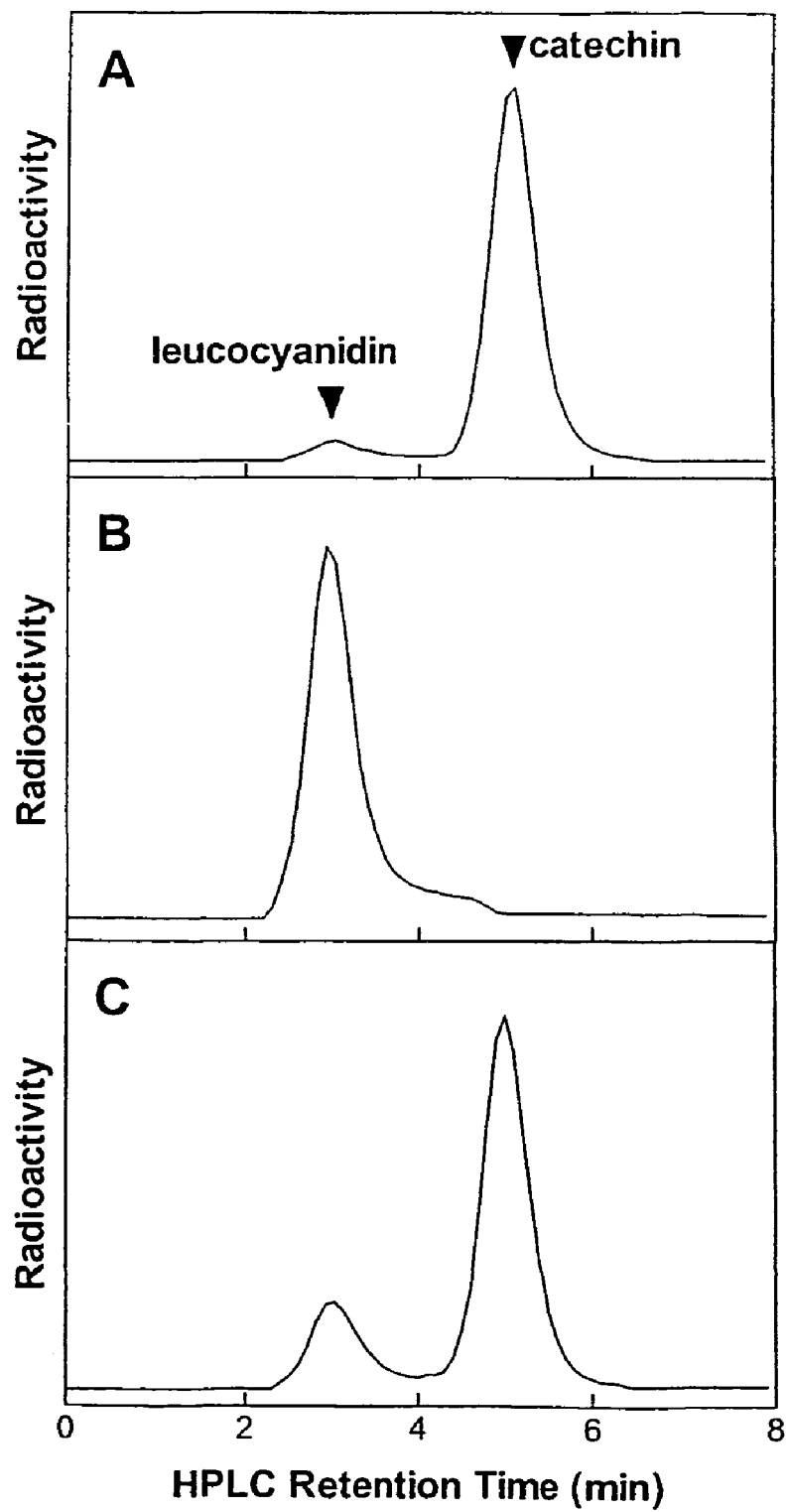
FIG. 13 is a copy of three radio-HPLC chromatograms which show the induction of LAR activity in *E. coli* transformed with the truncated expression construct as described in Example 13. Extracts of *E. coli*, transformed with pET LAR317 have produced LAR activity sufficient to convert all of the leucocyanidin substrate into catechin (panel A) when assayed as in Example 1 using HPLC system IIa. Extracts of control bacteria did not have any LAR activity (panel B). The catechin produced by pET LAR317 co-migrated with radio-catechin produced from authentic LAR enzyme purified from *Desmodium* (panel C). Radio-catechin co-eluted with authentic catechin.

Expression of the full length recombinant LAR382 protein, or the truncated form LAR317, was induced as described in the preceding Example. Bacterial protein extracts were assayed for LAR enzyme activity, essentially as described in Example 1. The recombinant LAR382 protein, and the truncated recombinant protein LAR317 catalysed the reduction of [4-$^3$H]-2,3-trans-3,4-cis-leucocyanidin similar to the activity of the naturally-occurring LAR enzyme in enzyme extracts prepared from leaf tissue (see FIGS. 12 and 13).

EXAMPLE 14

Immuno-precipitation of D. uncinatum LAR

LAR was partially purified about 2,300-fold from young leaves of Desmodium uncinatum by chromatography on a series of dye-ligand affinity columns essentially as described in Example 2, except that LAR was eluted from the Sepharose CL4B- Cibacron Orange F-R column, by applying a 40 ml linear NADP gradient to 0.5 mM NADP in dye column buffer 2. Fractions of 2.5 ml volume were collected.

Fractions containing LAR activity were pooled and stored frozen at −20 C for up to one month without loss of enzyme activity, thawed and applied to a 5 ml column of cholic acid-Sepharose (Sigma) at 2 ml/min. The column was washed with a buffer containing 10 mM phosphate, 20% (w/v) glycerol, 1 mM DTT all adjusted to pH7 and bound enzyme eluted by applying a 50 ml linear salt gradient to 125 mM NaCl. Fractions of 2 ml were collected. Chromatography on cholic acid was carried out at room temperature.

Fractions with LAR activity were combined and then concentrated to a final volume of 1 ml by applying nitrogen over a YM10 membrane (Amicon). The concentrate was mixed with an equal volume of glycerol and stored at −20 C The final yield of enzyme activity was 8.7% and purification was 2,360 fold. This gave an enzyme preparation in which the LAR enzyme activity was stable for up to one year and suitable for immuno-precipitation experiments.

Duplicate 0.5 μl aliquots of the LAR enzyme as purified above were incubated with 0.5 μl aliquots of crude rabbit antisera raised against either the C1 or C2 peptides diluted with 8.5 μl of a phosphate buffered saline (PBS) buffer containing 0.1% (w/v) Tween 20, 0.1 mM DTT and a protease inhibitor cocktail consisting of 0.1 mM Na$_2$ EDTA, 2 μg/ml leupeptin, 1 μg/ml pepstatin, and 1 μg/ml E64. Control incubations were carried out with either no antiserum (No antibody control) or similar additions of pre-immune serum (Preimmune) from the corresponding rabbits. After 30 min at 4C, a 50 μl aliquot of a 10% (w/v) suspension of killed S. aureus cells (Sigma) were added to all tubes and the antibodies removed by centrifugation. Protein blots indicated that all the rabbit antibodies had been removed from the supernatants by this treatment. The remaining supernatant was assayed for the presence of the LAR enzyme.

With antisera added at a final dilution of about ½₀× (Table 4) only antisera to C2 gave significant (50%) immunoprecipitation of LAR activity compared to either the preimmune or no addition controls.

A repeat incubation with a 10-fold higher concentrations of antiserum and killed S. aureus cells (Table 5) showed antisera to both C1 and C2 removed all of the LAR activity from solution.

TABLE 4

Effect of LAR antiserum at approximately ½₀ × final dilution on LAR activity (Mean + standard deviation as % no addition control)

| Antibody | Preimmune | Second bleed |
|----------|-----------|--------------|
| C1 | 80.7 + 17.2% | 66.5 + 3.8% |
| C2 | 85.2 + 7.2% | 43.8 + 6.5% |

TABLE 5

Effect of LAR antiserum at approximately ½ × final dilution on LAR activity (Mean + standard deviation as % no addition control)

| Antibody | Preimmune | Second bleed |
|---|---|---|
| C1 | 123 + 7.6% | 0 |
| C2 | 70.4 + 9.6% | 0 |

It is significant that the pre-immune and no addition controls from both experiments gave similar LAR activities. This confirms that the depletion of LAR activity from the supernatant was due to specific anti-C1 or anti-C2 antibodies and not non-specific protein adsorption or inhibition by the serum proteins or S. aureus cells.

High concentrations of pre- or post-immune antisera to both peptides did not inhibit LAR activity. Duplicate aliquots of LAR were incubated as above with either preimmune or second bleed antisera against either the C1, or C2 peptides respectively. After 10 min at 4 C this was added to the substrates and the LAR activity assayed for 30 min at 30 C as in Example 1.

Figure 7:
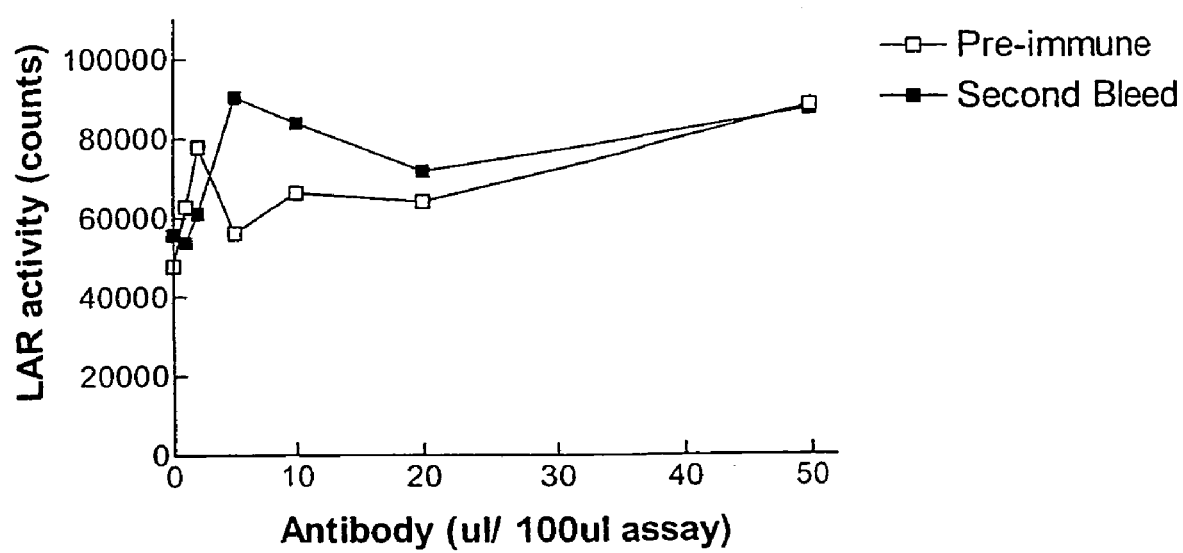
FIG. 7 is a copy of a graph showing the activity of purified LAR following incubation for 30 minutes at 4 C with the indicated volume of antiserum either from the pre-immune or second bleed anti-C1 antiserum.
Figure 8:
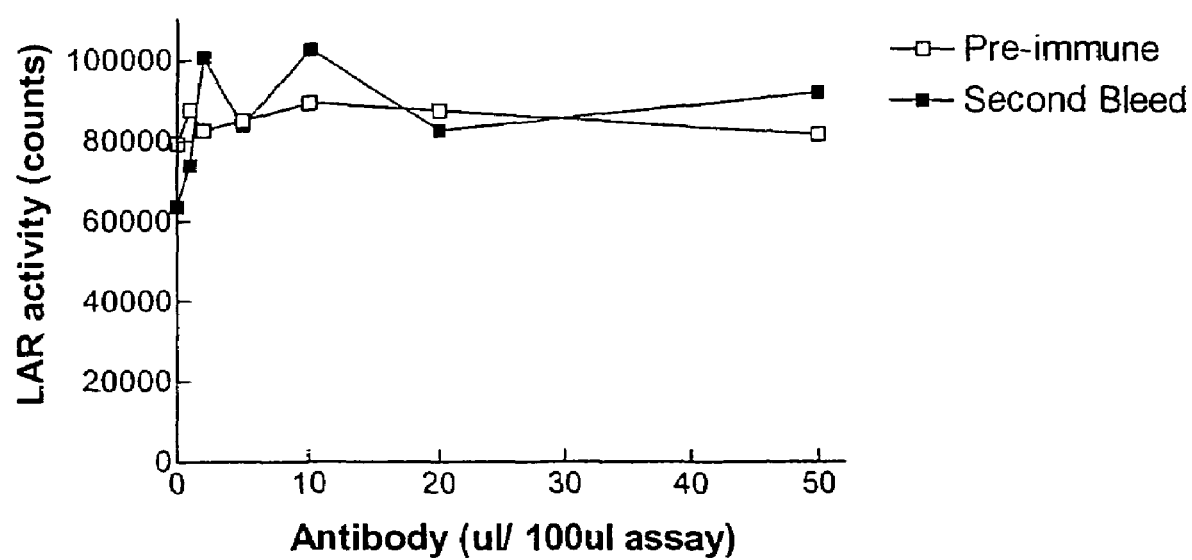
FIG. 8 is a copy of a graph showing the activity of purified LAR following incubation for 30 minutes at 4 C. with the indicated volume of antiserum either from the pre-immune or second bleed anti-C2 antiserum.

Incubation with antisera to either C1 (FIG. 7), or C2 (FIG. 8) at final dilutions up to ½× did not inhibit LAR activity significantly.

This confirms that the depletion of LAR activity from the supernatant in immuno-precipitation experiments above was due to anti-C1 or -C2 antibodies and not non-specific adsorption or inhibition by the serum proteins used for the immuno-precipitation.

EXAMPLE 15

Gel Filtration of *D. uncinatum* LAR in the Presence of Purified Immunoglobulins Additional antibody evidence was obtained which showed a specific interaction between purified immunoglobulins and LAR.

LAR was partially purified about 25,000-fold from young leaves of *Desmodium uncinatum* by chromatography on a series of dye-ligand affinity columns essentially as described in Example 2, except the chromatography on the hydroxyl apatite column was omitted, and only one batch of 100 g was processed. The final purification (25,000 fold) and yield (1.3%) were similar to that obtained in the experiment detailed in Example 2.

Aliquots of 10 μl (containing 70 ng of protein) of LAR purified as above were incubated at 4 C with 100 μl of IgG (containing 300 μg protein) purified either from C1 or C2 pre- or post-immune antisera by Protein G chromatography as in Example 11, and 140 μl of a buffer containing 20 mM NaPi, 20% (w/v) glycerol, 200 mM NaCl, 0.01% (w/v) Tween 20, and 0.1 mM DTT all adjusted to pH 7. After 30 minutes, 200 μl of the above mixture was injected onto a Superdex S200 column (Pharmacia) eluted at 0.5 ml/min with a buffer containing 20 mM NaPi, 20% (w/v) glycerol, 200 mM NaCl, 0.01% (w/v) Tween 20, and 0.1 mM DTT all adjusted to pH 7. Fractions of 0.2 ml were collected and assayed for LAR activity as described in Example 1 (see FIGS. 9 and 10).

Figure 9:
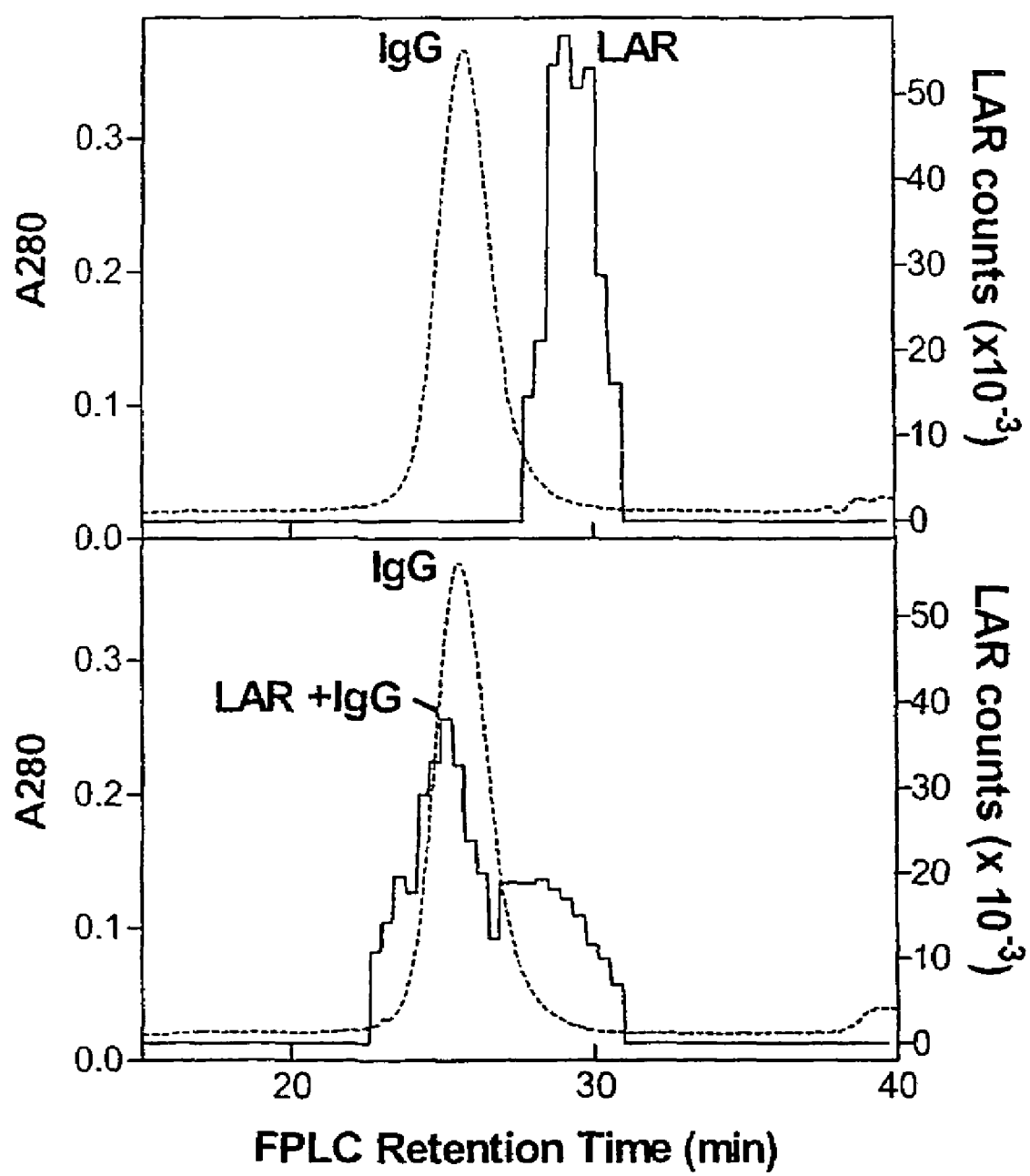
FIG. 9 is a copy of a chromatogram showing the effect on the apparent molecular weight of purified LAR after incubating with purified antibodies. LAR was partially purified to approximately 2,500 fold from *Desmodium* leaves as in Example 15 When the LAR preparation was mixed with IgG purified from C1 pre-immune antisera (upper panel), LAR activity migrated on a Superdex 200 gel filtration column (Pharmacia) as expected for a protein of molecular weight about 50,000 D (solid line). The bulk protein shown by A280 (dotted line) migrated. as a protein of 150,000 Da as expected for IgG. However when LAR was mixed with IgG purified from C1-second bleed antiserum (lower panel), most of the LAR activity migrated as a protein of molecular weight 200,000 Da, the size predicted for the combination of an IgG molecule and the LAR enzyme.
Figure 10:
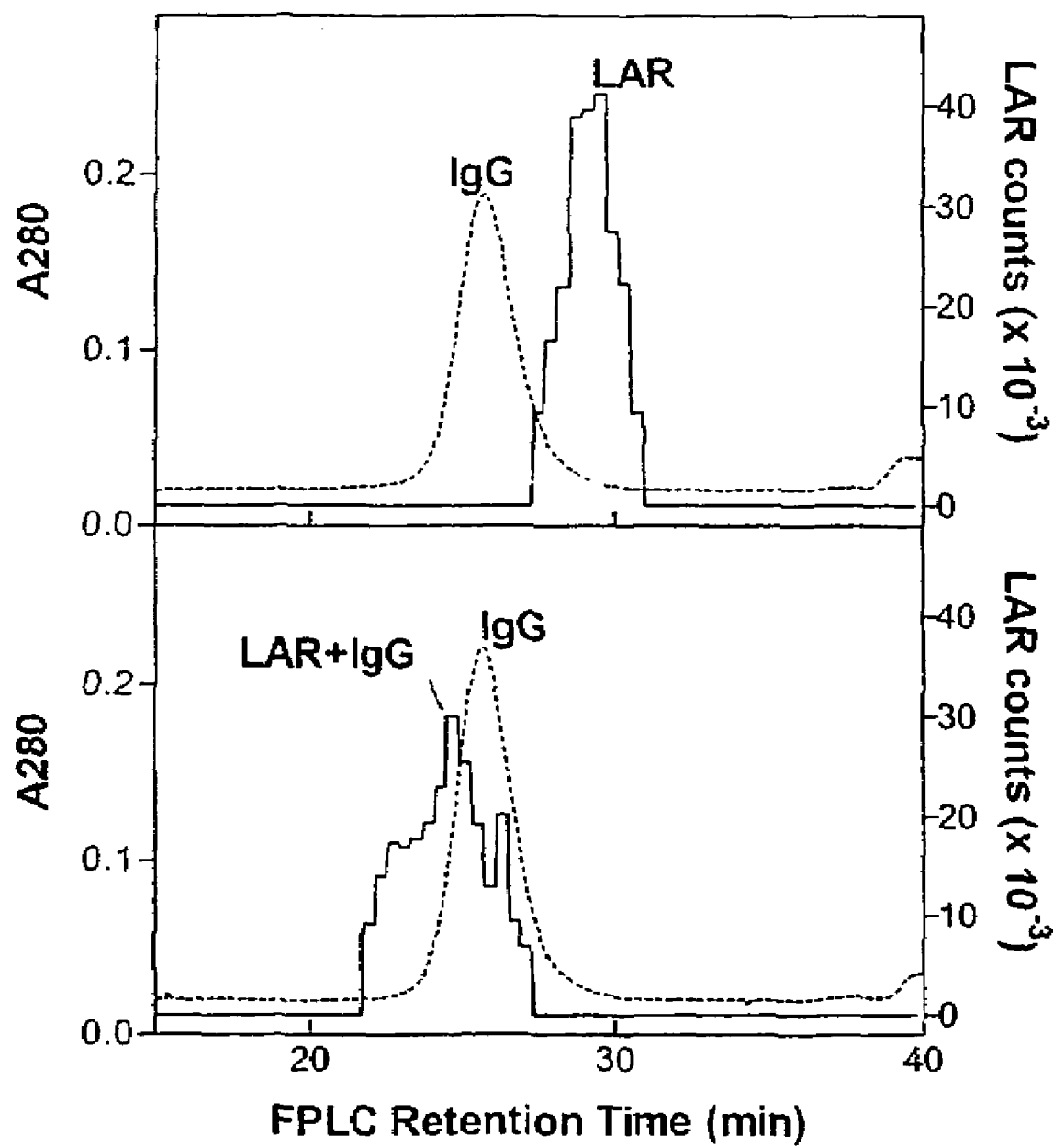
FIG. 10 is a copy of a chromatogram showing the effect on the apparent molecular weight of purified LAR after incubating with purified antibodies. LAR was partially purified to approximately 2,500 fold from *Desmodium* leaves as in Example 15. When the LAR preparation was mixed with IgG purified from C2 pre-immune antisera (upper panel) as in Example 11, LAR activity migrated on a Superdex 200 gel filtration column (Pharmacia) as expected for a protein of molecular weight about 50,000 D (solid line). The bulk protein shown by A280 (doted line) migrated as a protein of 150,000 Da as expected for IgG. However when LAR was mixed with IgG purified from C2-second bleed antiserum (lower panel), all the LAR activity migrated as a protein of molecular weight 200,000 Da, the size predicted for the combination of an IgG molecule and the LAR enzyme

In the presence of preimmune-IgG, LAR activity migrated as expected for a protein of molecular weight 50,000 Da, however in the presence of IgG purified from post-immune antisera, LAR activity migrated as a protein of molecular weight 200,000 Da, the size predicted for the combination of an IgG molecule and the LAR enzyme (FIG. 9 & 10).

This indicates a specific protein-protein interaction between the post-immune antibodies and the enzyme.

REFERENCES

Altschul, S. F., et al. (1997), "Gapped BLAST and PSI-BLAST: a new generation of protein database search programs", *Nucleic Acids Res.* 25, 3389–3402

An, G., et al. (1985) New cloning vehicles for transformation of higher plants. *EMBO J.* 4, 277–84.

Ashton, A. R. and Polya, G. M. (1978). The specific interaction of Cibacron and related dyes with cyclic nucleotide phophodiesterase and lactate dehydrogenase. *Biochem. J.*, 175, 501–506.

Ausubel, F. M., et al. (1987) Current Protocols in Molecular Biology, Wiley Interscience (ISBN 047140338).

Barry T N, and Reid C S W (1985) Nutritional effects attributable to condensed tannins, cyanogenic glycosides and oestrogenic compounds in New Zealand forages. In Forage Legumes for Energy-Efficient Animal Production. Eds Barnes R F, Ball P R, Brougham R W, Martin G C, Minson D J. pp 251–259. USDA, ARS, Washington D.C.

Bartels, D., et al. (1991). An ABA and GA modulated gene expressed in the barley embryo encodes an aldose reductase related protein. *The EMBO J.* 10, 1037–1043.

Bateman, A., et al. (2000) The Pfam contribution to the annual NAR database issue. *Nucl. Acids Res.* 28, 263–266.

Bird C R, et al. (1991) Using Antisense RNA to Study Gene Function—Inhibition of Carotenoid Biosynthesis in Transgenic Tomatoes. *Bio/Technology* 9, 635–639.

Braxnley P, et al. (1992) Biochemical Characterization of Transgenic Tomato Plants in Which Carotenoid Synthesis Has Been Inhibited Through the Expression of Antisense RNA to pTOM5. *Plant Journal* 2, 343–349.

Bruce, N. C., et al. (1994). Bacterial morphine dehydrogenase further defines a distinct superfamily of oxidoreductases with diverse functional activities. *Biochem J.* 299, 805–811.

Burkhard Morgenstern (1999) DIALIGN 2: Improvement of the segment-to-segment approach to multiple sequence alignment. *Bioinformatics* 15, 211–218.

Cole et al. (1985) In Monoclonal antibodies in cancer therapy, Alan R. Bliss Inc., pp 77–96.

De Block, M., et a. (1987) Engineering herbicide resistance in plants by expression of a detoxifying enzyme. *EMBO J.* 6, 2513–8.

Devic, M., et al. (1999) The BANYULS gene encodes a DFR-like protein and is a marker of early seed coat development *The Plant J.* 19, 387–398.

Fujiwara T, et al. (1992) Seed-specific repression of gus activity in tobacco plants by antisense RNA. *Plant Mol. Biol.* 20, 1059–1069.

Gamborg, O. J. and Eveleigh, D. E. (1968) Culture methods and glucanases in suspension cultures of wheat and barley. *Can. J. Biochem.* 46, 417–43.

Garfinkle (1980) *Agrobacterium tumefaciens* mutants affected in crown gall tumorigenesis and octopine catabolism. *J. Bacteriol.* 144, 732–43.

Hagen, G., et al. (1984) Auxin-induced expression of the soybean GH3 promoter in transgenic tobacco plants. *Plant Mol. Biol.* 17, 567–79.

Haseloff, J., and Gerlach, W. L. (1988) *Nature* 334, 586–594

Huse et a. (1989) *Science* 246, 1275–1281.

Jefferson, R. A., et al. (1987) GUS fusions: beta-glucuronidase as a sensitive and versatile gene fusion marker in higher plants. *The EMBO J.* 6, 3901–7.

Jende-Strid, B. (1978) Mutation frequencies obtained after sodium azide treatments in different barley varieties. *Barley Genetics Newsletter* 8, 55–57.

Jende-Strid, B. (1984) Coordinator's report: Anthocyanin genes. *Barley Genetics Newsletter* 14, 76–79

Jones, J. D. G., et al. (1992) Effective vectors for transformation, expression of heterologous genes, and assaying transposon excision in transgenic plant. *Transgenic Res.* 1, 285–97.

Khan, M. R. I., et al. (1994) *Agrobactenum*-mediated transformation of subterranean clover (*Trifolium subterranean* L.). *Plant Physiol.* 105, 81–8.

Klickstein, L. B. (1991) In: Current Protocols in Molecular Biology, Ausubel et al (eds.), Greene Publishing Associates and Wiley lnterscience Publishers, Chapter 5.

Kohler and Milstein (1975) Nature 256, 495–499

Kozbor et a. (1983) Immunol. *Today* 4, 72.

Kristiansen K N (1986) Conversion of (+)-dihydroquercetin to (+)2,3-trans-3,4-cis-leucocyanidin and (+)-catechin with an enzyme extract from maturing grains of barley. *Carlsberg Res. Comm.* 51, 51–60.

Laemmli U. K. (1970) *Nature* 227, 680.

Larkin P J, et al., (1996). Transgenic White Clover. Studies with the auxin responsive promoter, GH3, in root gravitropism and lateral root development. *Transgenic Res.* 5, 325–335.

Lazo, G. R., et al. (1991) A transformation-competent *Arabidopsis* genomic library in *Agrobacterium*. *Bio/Technology* 9, 963–967.

Lee J., et al. (1995). Sulphur amino acid metabolism and protein synthesis in young sheep fed ryegrass pasture and two lotus cultivars containing condensed tannins. *Aust. J. Agric. Res.* 46, 1587–1600.

Li Y -G, et al. (1996) The DMACA-HCl protocol and the threshold proanthocyanidin content for bloat safety in forage legumes. *J. Sci. Food Agric.* 70, 89–101.

Liang and Pardee (1992) *Nature* 257, 967–970.

Lyttleton (1971) (1971) NZ *J. Agric. Res.* 14, 101–107.

McNabb W. C., et al. (1993). The effect of condensed tannins in *Lotus pedunculatus* on the digestion and metabolism of methionine, cysteine, and inorganic sulphur in sheep. *Brit. J. Nutrition* 70, 647–661.

McPherson, M. J., et al. (1991) PCR A Practical Approach. IRL Press, Oxford University Press, Oxford, United Kingdom.

Niezen J. H., et al. (1995). Growth and gastrointestinal nematode parasitism in lambs grazing either lucerne (*Medicago sativa*) or Sulla (*Hedysarum coronarium*) which contains condensed tannins. *J. Agric. Sci.* 125, 281–289.

Phillips, G. C. and Collins, G. B. (1984) Red clover and other forage legumes. In Sharp, W. R., Evans, D. A., Ammirato, P. V. and Yamada, Y., eds., *Handbook of Plant Cell Culture Vol. 2 Crop Species*, pp. 169–210. New York: Macmillan Publishing.

Pietrzak, M., et al. (1986) Expression in plants of two bacterial antibiotic resistance genes after protoplast transformation with a new plant expression vector. *Nucl. Acids Res.* 14, 5857–68.

Sanger F, et al. (1977) DNA sequencing with chain terminating inhibitors. *Proc Natl. Acad. Sci* (USA) 74, 5463–5466.

Scopes, R. K. (1994) In: Protein purification: Principles and Practice (third edition). Springer Verlag, New York.

Tabe, L. M., et al. (1995). A biotechnological approach to improving the nutritive value of alfalfa. *J. Animal Science* 73, 2752–2759.

Tam, J. P. (1984). Immunisation with peptide-carrier complexes: traditional and multiple-antigen peptide systems. In Peptide Antigens, A Practical Approach. Ed Wisdom G. B., pp83–116. IRL Press, Oxford, UK.

Tanner G J, and Kristiansen K N (1993) Synthesis of 3,4-cis-[H3]1eucocyanidin and enzymatic reduction to catechin. *Anal. Biochem.* 209, 274–277.

Tanner G J, et al. (1995). Proanthocyanidins (condensed tannin) destabilise plant protein foams in a dose dependent manner. *Aust J Agric Res* 46, 1101–1109.

Terrill T H, et al. (1992a) Determination of extractable and bound condensed tannin concentrations in forage plants, protein concentrate meals and cereal grains. *J Sci Food Agric* 58, 321–329.

Terrill T. H., et al. (1992b) The effect of condensed tannins upon body growth, wool growth and rumen metabolism in sheep grazing Sulla (*Hedysarum coronarium*) and perennial pasture. *J. Agric. Sci.* 119, 265–273.

Thompson, J. D., et al. (1994) *Nucl. Acids Res.* 22, 4673–4680.

Voisey, C. R., et al. (1994) Agrobacterium-mediated transformation of white clover using direct shoot organogenesis. *Plant Cell Rep* 13, 309–314.

Wang Y., et al. (1994) The effects of condensed tannin in *Lotus corniculatus* upon nutrient metabolism and upon body and wool growth in grazing sheep. Proc. 1994 NZAPS Conference.

Welle, R., etal. (1991). Induced plant responses to pathogen attack. Analysis and heterologous expression of the key enzyme in the biosynthesis of phytoalexins in soybean (Glycine max L. Merr. cv. Harosoy 63). *Eur. J. Biochem.* 196, 423–430.

The invention claimed is:

1. An isolated nucleic acid molecule comprising nucleotides in a sequence encoding a leucoanthocyanidin reductase (LAR) polypeptide of the reductase-epimerase-dehydrogenase (RED) protein superfamily, or a full complement of the nucleic acid molecule, wherein the polypeptide comprises amino acids having a sequence set forth in SEQ ID NO: 29.

2. An isolated nucleic acid molecule according to claim 1, in the form of RNA, or DNA, or a mixed polymer comprising RNA and DNA.

3. An isolated nucleic acid molecule according to claim 1, which comprises (i) the nucleotide sequence set forth in SEQ ID NO: 28; or (ii) the nucleotide sequence that is complementary to the sequence of (i) above.

4. The isolated nucleic acid molecule of claim 1, further comprising a promoter sequence in operable connection with said isolated nucleic acid molecule.

5. The isolated nucleic acid molecule of claim 4, further comprising a terminator sequence, and an origin of replication.

6. An isolated or recombinant leucoanthocyanidin reductase (LAR) polypeptide of the reductase-epimerase-dehydrogenase (RED) protein superfamily encoded by the isolated nucleic acid molecule of claim 1.

7. The isolated polypeptide of claim 6, which is substantially free of conspecific proteins.

8. A plant or a bacterial cell comprising a heterologous nucleic acid molecule in an expressible format, wherein the nucleic acid molecule encodes a leucoanthocyanidin reductase (LAR) polypeptide of the reductase-epimerase-dehydrogenase (RED) protein superfamily, or a full complement of the nucleic acid molecule, wherein the polypeptide comprises amino acids having a sequence set forth in SEQ ID NO: 29.

9. The cell of claim 8, which is a bacterial cell.

10. The cell of claim 9, which is an *Agrobacterium tumefaciens* cell.

11. The cell of claim 8, which is a plant cell.

12. The cell of claim 11, wherein the plant cell is the cell of a legume.

13. The cell of claim 12, which is contained within a plant organ or a whole plant.

14. The cell of claim 13, wherein the plant is a fodder or forage legume.

15. The cell of claim 14, wherein the legume is a species of *Medicago* or *Trifolium*.

16. A plant comprising a non-endogenous nucleic acid molecule in expressible format, wherein the non-endogenous nucleic acid molecule comprises nucleotides in a sequence encoding a polypeptide comprising amino acids having a sequence set forth in SEQ ID NO: 29; and wherein the nucleic acid molecule has been introduced into the genome of the plant or the genome of a progenitor of the plant.

17. The plant according to claim 16, wherein the nucleic acid molecule has been introduced into the genome of the plant or progenitor of the plant by transformation.

18. The plant according to claim 16, which is a legume.

19. The plant of claim 18, wherein the legume is a fodder or forage legume.

20. The plant of claim 18, wherein the legume is a species of *Medicago* or *Trifolium*.

21. A method of enhancing the expression of an LAR polypeptide of the RED protein superfamily in a plant, comprising introducing to the genome of said plant a non-endogenous nucleic acid molecule according to claim 1 in an expressible format.

* * * * *